United States Patent [19]

Aberg et al.

[11] Patent Number: 5,879,907
[45] Date of Patent: Mar. 9, 1999

[54] ARTIFICIAL GENE CODING FOR AUTHENTIC HUMAN SERUM ALBUMIN, USE THEREOF AND METHOD

[75] Inventors: Bertil Aberg; András Simoncsits, both of Stockholm, Sweden; Miklós Kálmán, Szeged, Hungary; Imre Cserpán, Szeged, Hungary; György Bajszár, Szeged, Hungary

[73] Assignees: Skandigen AB, Stockholm, Sweden; MTA Szegedi Biológiai Központja, Szeged; Vepex Contractor Ltd., Budapest, both of Hungary

[21] Appl. No.: 884,274

[22] Filed: May 13, 1992

Related U.S. Application Data

[63] Continuation of Ser. No. 466,417, May 1, 1990, abandoned.

[30] Foreign Application Priority Data

Sep. 14, 1987 [SE] Sweden ................................. 8703539
Sep. 13, 1988 [WO] WIPO ..................... PCT/SE88/00470

[51] Int. Cl.$^6$ ............................. C12N 15/81; C07H 21/04
[52] U.S. Cl. ................ 435/69.1; 435/172.3; 435/252.33; 435/254.2; 435/254.21; 435/320.1; 536/23.1; 536/23.5
[58] Field of Search ................................. 435/69.1, 69.2, 435/69.4, 172.1, 172.2, 172.3, 69.6, 320.1, 252.3, 252.33, 254.2, 254.21; 536/27, 28, 23.1, 23.5; 530/350, 351, 387, 362, 363, 385, 386, 388, 389

[56] References Cited

U.S. PATENT DOCUMENTS

| | | | |
|---|---|---|---|
| 4,695,623 | 9/1987 | Stabinsky | 530/351 |
| 5,013,652 | 5/1991 | Strausberg et al. | 435/69.2 |

FOREIGN PATENT DOCUMENTS

| | | |
|---|---|---|
| 079 739 | 5/1983 | European Pat. Off. . |
| 123 544 | 10/1984 | European Pat. Off. . |
| 0 182 383 | 5/1986 | European Pat. Off. . |
| 0206733 | 12/1986 | European Pat. Off. ........ C12N 15/00 |
| 206 733A | 12/1986 | European Pat. Off. . |
| 2 105 343 | 3/1983 | United Kingdom . |
| WO 83/04053 | 11/1983 | WIPO . |
| WO 87/07144 | 12/1987 | WIPO . |

OTHER PUBLICATIONS

Sharp, P.M. et al., "Codon usage in yeast: cluster analysis clearly differentiates and lowly expressed genes," *Nucleic Acids Research*, vol. 14, No. 13 (1986), pp. 5125–5143.

Bennetzen, J.L. and Hall, B.P., "Codon Selection in Yeast," *Journal of Biological Chemistry*, vol. 257, No. 6 (Mar. 25, 1982), pp. 3026–3031.

*Primary Examiner*—John L. LeGuyader
*Attorney, Agent, or Firm*—Bacon & Thomas

[57] ABSTRACT

A structural gene coding for authentic human serum albumin, —optionally supplemented by an upstream triplet coding for methionine and optionally extended by a synthetic prepro$^x$-leader-coding sequence—, wherein the codons of the nucleotide sequence have been selected with regard to a non-human host, e.g. yeast, chosen for expression of authentic human serum albumin, is disclosed.

Additionally there is disclosed a method of producing said gene.

There are also disclosed a recombinant DNA molecule comprising said strucural gene inserted into a vector, and a host transformed with said recombinant DNA molecule.

Furthermore there are disclosed a method of producing authentic human serum albumin, an authentic human serum albumin resulting from said method, and a pharmaceutical composition comprising said resulting human serum albumin.

10 Claims, 12 Drawing Sheets

ARTIFICIAL GENE CODING FOR AUTHENTIC HUMAN SERUM ALBUMIN, USE THEREOF AND METHOD

This application is a Continuation of application Ser. No. 07/466,417, filed May 1, 1990, now abandoned, which is a 371 of PCT/SE88/00470, filed Sep. 13, 1998.

The present invention is directed to a structural gene coding for authentic human serum albumin—optionally supplemented by an upstream triplet coding for methionine and optionally extended by a synthetic prepro$^x$-leader-coding sequence—, to a recombinant DNA molecule comprising said gene inserted into a vector, to a host transformed with said DNA molecule, to a method of producing authentic human serum albumin, to an authentic human serum albumin and to a pharmaceutical composition comprising authentic human serum albumin. The invention is additionally directed to a method of producing a structural gene coding for authentic human serum albumin.

BACKGROUND

Serum albumin is the major protein component of serum in higher species. Its role is in maintaining osmotic balance and it is involved in the binding and transport of sparingly soluble metabolic products from one tissue to another, especially in the transport of free fatty acids. Human serum albumin is used in therapy for the treatment of hypovolemia, shock and hypoalbuminemia. It is also used as an additive in perfusion liquid for extracorporeal circulation. Furthermore, human serum albumin is frequently used as experimental antigen.

Human serum albumin is composed of a single long polypeptide chain comprising nearly 600 amino acid residues. The amino acid sequence thereof is published. (See e.g. [Lawn R. M., et. al., Nucleic Acids Research, Vol. 9, No. 22 (1981) pp. 6103–6113)]. Commercial human serum albumin is prepared from human plasma. The availability of human plasma is limited.

Careful heat treatment of the product prepared from human plasma must be effected to avoid potential contamination of the product by hepatitis B virus and HIV virus.

Since one of the characteristics of HIV virus is to frequently change its antigenic structure, there are no guarantees that it will not develop heat resistant variants.

Obviously, there is a need for artificial authentic human serum albumin that can be produced in unlimited quantities.

PRIOR ART

Several attempts to produce products corresponding to mature human serum albumin by using recombinant DNA techniques have been made and published i.a. in the following patent applications.

EP-A-0 073 646 (Genentech Inc), EP-A-0 079 739 (The Upjohn Co.), EP-A-0 091 527 (President and Fellows of Harvard College), and EP-A-0 198 745 (Genetica).

All of the above mentioned patent applications have started from isolation of mRNA from human liver, and this mRNA has been used to prepare double-stranded cDNA (or fragments thereof). Consequently the codon usage in the cDNAs is by nature optimized for human expression.

It is considered in the art that human codon usage is not ideal for non-human expression.

Prior to the present invention there have not been produced such large DNA sequences as needed for authentic human serum albumin (structural gene=1761 bp) in which the codons are optimized for non-human expression.

In EP-A-0 182 383 (Vepex Contractor Ltd., and MTA Szegedi Biologiai Központja) is disclosed a process for the production of oligo- and polydeoxyribonucleotides by synthesizing the complementary strand of a single-stranded DNA piece enzymatically. This technique has been partly used in the method of producing a structural gene coding for authentic human serum albumin (HSA) according to the present invention, but it was combined with a new technique of joining a few large fragments of the gene.

DESCRIPTION OF THE INVENTION

The main object of this invention is to produce authentic human serum albumin with the aid of an artificial structural gene having a nucleotide sequence wherein the codons are optimized for non-human expression.

To realize this object it was first necessary to design an artificial structural gene and to invent a method of producing said gene.

Design of the artificial structural gene

It was decided to choose codons especially suited for yeast expression as an useful example of non-human expression.

The codons were selected from yeast codons for highly expressed yeast proteins (Bennetzen, J. L. and Hall, B. D. (1982) J. Biol. Chem. 257, 3026–3031, and Sharp, P. M., Tuohy, T. M. F. and Mosurski, K. R. (1986) Nucleic Acids Res. 14, 5125–5143).

In the first instance, the codons most frequently used by yeast were selected, but where appropriate the second or third codon was used.

The reasons for choosing the second or third codons were a) to avoid the appearance of such restriction sites which are to be used during the assembly of the gene, b) to create one unique cleavage site for a specific enzyme, and c) to eliminate 8-base pairs long or longer palindromes within such parts of the gene which are to be chemically synthesized and cloned; to avoid possible internal loops or secondary structural formations within the individual synthetic oligonucleotides.

Artificial structural gene coding for authentic HSA

In one aspect of the invention there is provided a structural gene coding for authentic human serum albumin. Said gene is characterized by a nucleotide sequence wherein the codons have been selected with regard to a non-human host chosen for expression of authentic human serum albumin, whereby the selection of the codons has been effected so that, in the first instance, the codons most frequently used by the chosen non-human host were selected, and in the second instance, the codons used by the chosen non-human host in the second or third place were selected, to avoid the appearance of such restriction sites which are to be used during the assembly of the gene, to create one unique cleavage site for a specific enzyme, and to eliminate 8-base-pairs long or longer palindromes within such parts of the gene which are to be chemically synthesized and cloned.

In a variant of this aspect of the invention there is provided a structural gene coding for authentic human serum albumin plus an initial extra methionine. In this variant of the gene the nucleotide sequence starts with a triplet coding for methionine and the rest of the nucleotide sequence codes for human serum albumin as above. When this gene is expressed there is produced either authentic human serum albumin or a methionyl derivative thereof, depending on the expression system used.

In an other variant of this aspect of the invention there is provided a structural gene coding for authentic human serum albumin, extended by an upstream nucleotide sequence in which the codons have been selected with regard to a non-human host and which codes for the amino acid sequence Met-Lys-Trp-Val-Thr-Phe-Ile-Ser-Leu-Leu-Phe-Leu-Phe-
-Ser-Ser-Ala-Tyr-Ser-Arg-Gly-Val-Phe-Lys-Arg A "structural gene" is a DNA sequence which codes for a specific peptide or protein through its template or messenger RNA, and includes stop codon(s).

A "functional gene" comprises, in addition to a structural gene, flanking sequences. Such flanking sequences comprise regulatory regions, such as a promoter sequence and a transcriptional terminator sequence. The flanking regions should be optimized for the specific vectors and hosts used for the expression (and production) of the peptide or protein encoded by the structural gene.

In a preferred embodiment of the invention, the structural gene coding for authentic HSA has a nucleotide sequence wherein the codons are selected with regard to yeast expression of authentic HSA. Even though only codons selected with regard to yeast expression are exemplified in the present specification, the teachings given herein will enable a man skilled in the art to design and construct a structural gene coding for authentic HSA wherein the nucleotide sequence has codons selected with regard to another non-human host, such as a bacterial host or a plant host.

The expression "authentic human serum albumin" has been used in this specification and claims to define an artificially produced protein of non-human origin having an amino acid sequence which corresponds to the amino acid sequence of native mature human serum albumin.

Recombinant DNA molecule

In an other aspect of the invention there is provided a recombinant DNA molecule comprising a structural gene according to the invention inserted into a vector.

The recombinant DNA molecule thus comprises a vector into which is inserted a functional gene (including a structural gene according to the invention) wherein the flanking sequences are adapted for the vector, and the host to be used.

Commonly used vectors are plasmids from bacteria, especially *E. coli*, and bacteriophages, e.g. lambda phage.

Specific examples of this aspect of the invention are disclosed in the part of this specification describing preferred embodiments of the invention.

Transformed host

In still another aspect of the invention there is provided a host transformed with a recombinant DNA molecule according to the invention.

Even though the codons of the nucleotide sequence in the structural gene (in a preferred embodiment of the invention) are selected with regard to a yeast host, yeast strains are not the only hosts which can be used. The structural gene designed for yeast expression may also be suited for bacterial or plant expression. Thus the host can be a yeast cell, e.g. *Saccharomyces cerevisiae*, a bacterial cell, such as *E. coli* or *Bacillus subtilis*, or a cell of a plant, such as bean plants, pea plants or tobacco plants.

Method of producing the artificial structural gene

In a further aspect of the invention there is provided a method of producing a structural gene coding for authentic human serum albumin. Said method comprises the following steps, a) designing the nucleotide sequence coding for authentic human serum albumin by selecting codons with regard to a non-human host chosen for expression of authentic human serum albumin, whereby the selection of the codons is effected so that in the first instance, codons most frequently used by the chosen non-human host are selected, and in the second instance, codons used by the chosen non-human host in the second or third place are selected, to avoid the appearance of such restriction sites which are used during the assembly of the gene, to create one unique cleavage site between a 5'-fragment and the rest of the whole gene, and to eliminate 8-base-pairs long or longer palindromes within oligonucleotide subunits of fragments to be cloned, b) dividing the designed nucleotide sequence into a 5'-fragment to be chemically synthesized and a few fragments to be cloned so that joining points between said few fragments will be at suitably located G-C dinucleotide sequences, c) modifying said designed few fragments of b) by supplementing the designed nucleotide sequences thereof with an extra nucleotide sequence GGTAC at the 5'-terminus, except for the fragment to be joined to the 5'-fragment of b), and further dividing said few fragments into subunits having a 3'-nucleotide G, which subunits in turn are individually supplemented with an extra nucleotide sequence GGCC;

d) individually chemically synthesizing the modified supplemented subunits of c) in single-stranded form in per se known manner, and chemically synthesizing the 5' fragment of b) in double-stranded form in per se known manner;

e) consecutively cloning the synthesized subunits of d) starting from the 5'-terminus of the modified supplemented few fragments of c) into a few individual recombinant vectors in per se known manner, with the aid of adapters and enzymatical filling-in reaction, to form cloned double-stranded fragments of the gene, which correspond to the modified supplemented few fragments of c), f) assembling the cloned double-stranded fragments of e) by cleaving the few recombinant vectors of e), in pairs, with the enzyme KpnI and the enzyme ApaI, respectively, —one at the created 5'-terminal KpnI restriction site, and the other at the created 3' terminal ApaI restriction site, —to form sticky ends which are made blunt ends by a single-strand-specific enzyme in per se known manner—leaving an end-nucleotide C and an end-nucleotide G, respectively—followed by cleavage with another restriction enzyme having a cleavage site which is unique in both of the recombinant vectors of the pair in question, to form on the one hand a linear vector containing a cloned fragment of the gene and, on the other hand, a cleaved-off fragment of the gene, which two last-mentioned fragments are, in per se known manner, enzymatically joined at the blunt ends—a dinucleotide G-C which is included in the nucleotide sequence of the gene, being formed at the joining point—to obtain a recombinant vector which finally includes all the few designed fragments of b) in double-stranded form, and g) supplementing the recombinant vector obtained in f) with the chemically synthesized 5' fragment of d) to form the whole structural gene coding for authentic human serum albumin.

The designed structural gene, having 1761 nucleotides coding for authentic mature human serum albumin having 585 amino acid residues, was in a preferred embodiment divided into five large fragments. The first fragment was synthesized double stranded in per se known manner, and the second to fifth fragments were produced according to the technique disclosed in EP-A-0 182 383, whereby a single strand is chemically synthesized and the complementary strand is enzymatically synthesized.

The expression "a unique cleavage site" means that the cleavage site is characteristic of a specific enzyme and that it does not occur anywhere else in the fragments to be joined.

The technique of joining two fragments having selected end-nucleotides was also used later in the intermediate plasmid constructions leading to the yeast expression vector.

The details of the method of the invention are described in connection with the preferred embodiments of the invention.

Method of production authentic HSA

In yet another aspect of the invention there is provided a method of producing authentic human serum albumin by propagating a host transformed with a vector comprising a recombinant DNA sequence under expression and optionally secretion conditions and isolating the expressed and optionally secreted protein product. The characteristic features of this method are a) that a host transformed with a vector comprising a structural gene according to the invention is utilized, and b) that authentic human serum albumin or optionally the methionyl derivative thereof is isolated.

In a preferred embodiment of this aspect of the invention the host used is *Saccharomyces cerevisiae* transformed with a shuttle vector (*E. coli*—yeast) comprising a structural gene coding for authentic human serum albumin, said gene being composed of a nucleotide sequence wherein the codons have been selected with regard to a yeast host.

Authentic HSA

In still another aspect of the invention there is provided authentic human serum albumin resulting from the method of producing the same according to the invention. This authentic HSA can be used for all applications instead of native mature HSA.

Pharmaceutical composition

In an additional aspect of the invention there is provided a pharmaceutical composition comprising authentic human serum albumin according to the invention in admixture with a pharmaceutically acceptable carrier and/or diluent. Suitable carriers and/or diluents are those used for native HSA, such as saline solution, and reference is made to e.g. US Pharmacopoeia for guidance. The same also applies to conventional additives, such as preservatives, pH regulators, buffers etc which may optionally be included.

DESCRIPTION OF PREFERRED EMBODIMENTS AND EXPERIMENTAL DETAILS

Short Description of the Drawings

The drawings relate to plasmid constructions and to a fluorograph. Specifically, FIG. 1 shows the physical map of the coliplasmid pGB1.

Figure 1:
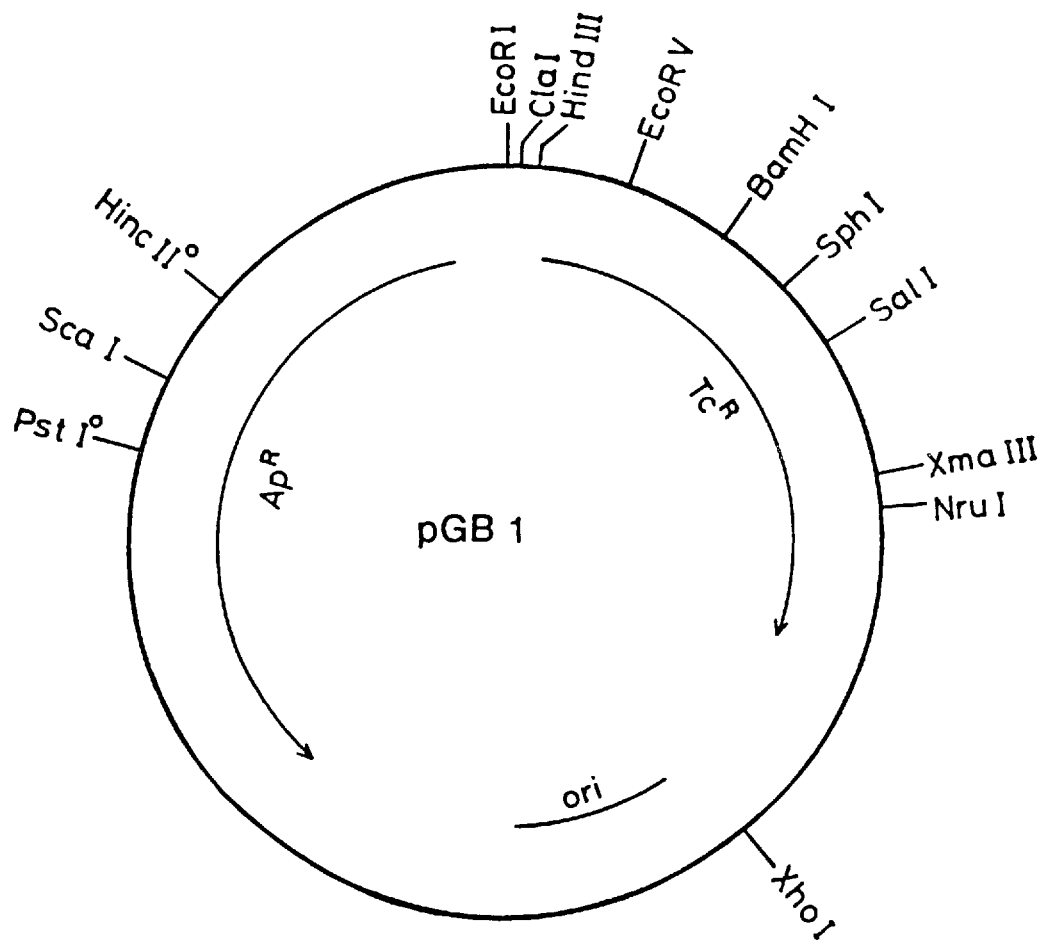

Scheme 1 - Map of the artificial HSA gene

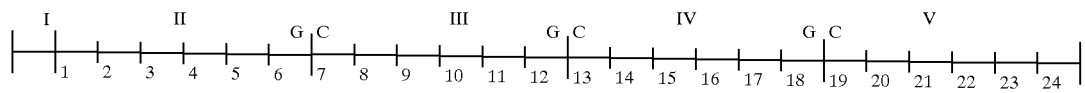

Roman numerals: large HSA fragments: HSA I, II, III, IV, V. Arabic numerals: synthetic oligodeoxyribonucleotides HSA 1, 2, 3 . . . 24, each containing an extra GGCC sequence at their 3'-terminus. This extra sequence does not show up in the HSA sequence. HSA 7, 13 and 19 oligonucleotides also contain an extra GGTAC sequence at their 5'-terminus, which does not show up in the final HSA sequence.

When an oligonucleotide (HSA 1) is ligated with the adapter molecule, it will be called, e.g. HSA 1+A (see Scheme 2).

When HSA 1+A is cloned into the commonly used *E. coli* vector pUC19 [Yannisch-Perron C., Vieira, J. and Messing, J. Gene 33, 103–119, (1985)] the plasmid obtained is called pHSA 1.

When HSA 2+A is cloned into the above obtained pHSA 1, the resulting plasmid is called pHSA (1-2).

Subsequent clonings will result in pHSA (1-6), which plasmid contains the HSA II large fragment cloned in pUC19, and it can be called pHSA II.

Similarly, HSA III, HSA IV and HSA V large fragments are obtained from oligonucleotides 7–12, 13–18 and 19–24, respectively, resulting in pHSA III, pHSA IV and pHSA V plasmids.

When HSA II and HSA III large fragments are joined in pUC19 vector, the resulting plasmid can be called pHSA (1-12) or rather pHSA (II-III).

Similarly, when HSA IV and HSA V large fragments are joined in pUC19 vector, the resulting plasmid can be called pHSA (13-24) or rather pHSA (IV-V).

When pHSA (II-III) and pHSA (IV-V) are joined, they will result in pHSA (II-V) in which nearly the whole coding region of HSA (from 13–585 amino acids of mature—without N-terminal Met) is cloned.

When pHSA (II-V) is supplemented with HSA I fragment in pUC19, the resulting plasmid will be named pHSA.

HSA I fragment was synthesized as a partial duplex in two forms. (Scheme 4).

Accordingly, two versions of pHSA, namely pHSA No 1 and pHSA No 2 are obtained (Scheme 5).

From pHSA No 2, Met-HSA coding gene can be obtained (as a fragment with blunt-end and with SacI end, Scheme 6).

From pHSA No 1, mature HSA coding gene can be obtained (as a fragment with blunt-end and with SacI end, Scheme 7).

Either Met-HSA or mature HSA coding DNA region can be cloned into pPT2HK$_1$ *E. coli* vector containing the PHO5 yeast promoter+signal sequence coding region and the His3 yeast transcription terminator. (To obtain pPT2/HSA). The promoter-signal sequence—HSA gene—terminator cassette will be incorporated into a self-replicating yeast vector pBY200 for HSA expression.

Scheme 2 - Example of the ligation of an oligonucleotide with adapter molecule

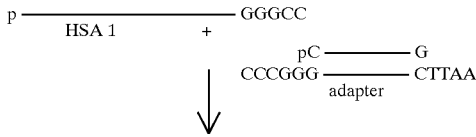

-continued

Scheme 2 - Example of the ligation of an oligonucleotide with adapter molecule

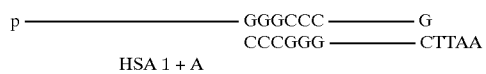

The HSA 1 oligonucleotide and the upper strand of the adapter are 5'-phosphorylated, while the adapter lower strand is not.

Scheme 3 - Adapters used during HSA cloning

```
ApaI                                          EcoRI    Adapter 1
      CGGACGGCGACGGCGACGGCGACCG
CCCGGGCCTGCCGCTGCCGCTGCCGCTGGCTTAA ApaI                                          EcoRI    Adapter 2
      CGAGTATGCGACAGCTGG
CCCGGGCTCATACGCTGTCGACCTTAA ApaI          SacI           EcoRI            Adapter 3
       CTGGAGCTCAGTCTG
CCGGGACCTCGAGTCAGACTTAA
```

Adapter 1 was used to facilitate cloning of most of the HSA oligonucleotides

Adapter 2 was used for HSA 16, 17 and 18 oligonucleotides

Adapter 3 was used to replace Adapter 1 downstream of the HSA gene, in order to introduce a SacI site necessary to clone the HSA gene into the *E. coli* vector pPT2HK$_1$ containing the yeast promoter and terminator regions.

Scheme 4 - HSA I fragments

```
       PstI                                                        Sau3AI
          Asp Ala His Lys Ser Glu Val Ala His Arg Phe Lys
          GACGCTCACAAGTCTGAAGTCGCTCACAGATTCAAG
No 1   ACGTCTGCGAGTGTTCAGACTTCAGCGAGTGTCTAAGTTCCTAG

PstI    BclI   Met Asp Ala His Lys Ser Glu Val Ala His Arg Phe Lys   Sau3AI
              GTGATCATGGACGCTCACAAGTCTGAAGTCGCTCACAGATTCAAG
No 2   ACGTCACTAGTACCTGCGAGTGTTCAGACTTCAGCGAGTGTCTAAGTTCCTAG
```

Scheme 5
Cloning the complete HSA gene versions into pUCl9
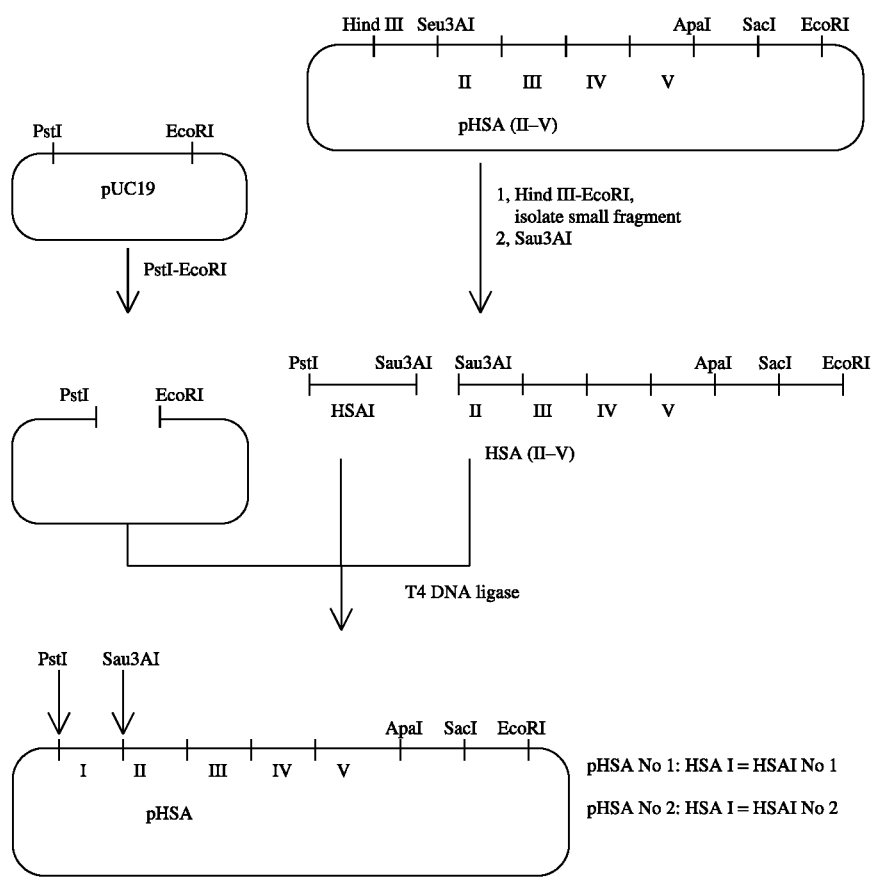
Scheme 6
Obtaining Met-HSA coding DNA piece from pHSA No 2
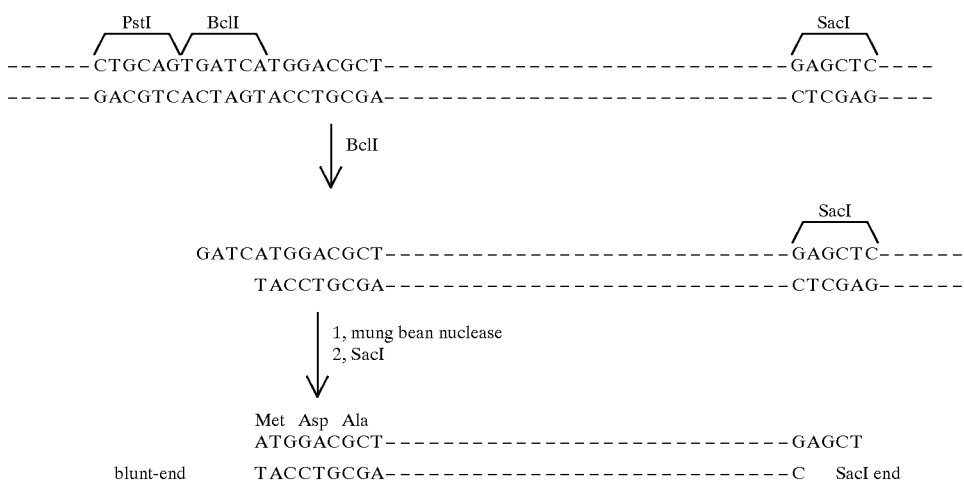
Note: To obtain the Met-HSA coding region an <u>unique</u> restriction site was introduced into HSAI (then into pSHA), namely BclI recognition sequence into HSAI (then into pSHA resulting in pSHA No 2 version).

Scheme 7
obtaining mature HSA coding DNA from pHSA No 1

```
     PstI                                              SacI
-----CTGCAGACGCT---------------------------GAGCTC-----
-----GACGTCTGCGA---------------------------CTCGAG-----
          │ PstI
          ▼

SacI
          GACGCT---------------------------GAGCTC-----
     ACGTCTGCGA---------------------------CTCGAG-----
          │ 1. Klenow polymerase + dNTP
          │ 2. SacI
          ▼
          Asp Ala
          GACGCT---------------------------GAGCT
blunt-end CTGCGA---------------------------C        SacI end
```

Scheme 8
Designed DNA sequence to code for mature HSA

1/1

ASP ALA HIS LYS SER GLU VAL ALA HIS ARG PHE LYS ASP LEU GLY GLU GLU ASN PHE

GAC GCT CAC AAG TCT GAA GTC GCT CAC AGA TTC AAG GAT CTA GGT GAA GAA AAC TTC
                                                         ↳ HSA1

20/58

LYS ALA LEU VAL LEU ILE ALA PHE ALA GLN TYR LEU GLN GLN CYS PRO PHE GLU ASP HIS

AAG GCT TTG GTT TTG ATT GCT TTC GCT CAA TAC TTG CAA CAA TGT CCA TTC GAA GAC CAC
                                                                        ↳ HSA2

40/118

VAL LYS LEU VAL ASN GLU VAL THR GLU PHE ALA LYS THR CYS VAL ALA ASP GLU SER ALA

GTC AAG TTG GTC AAC GAA GTT ACT GAA TTT GCT AAG ACC TGT GTT GCT GAC GAA TCT GCT

60/178

GLU ASN CYS ASP LYS SER LEU HIS THR LEU PHE GLY ASP LYS LEU CYS THR VAL ALA THR

GAA AAC TGT GAC AAG TCC TTG CAC ACT TTG TTC GGT GAC AAG TTG TGT ACT GTT GCT ACT
         ↳ HSA3

80/238

LEU ARG GLU THR TYR GLY GLU MET ALA ASP CYS CYS ALA LYS GLN GLU PRO GLU ARG ASN

TTG AGA GAA ACT TAC GGT GAA ATG GCT GAC TGT TGT GCT AAA CAG GAA CCA GAA AGA AAC
                        ↳ HSA4

100/298

GLU CYS PHE LEU GLN HIS LYS ASP ASP ASN PRO ASN LEU PRO ARG LEU VAL ARG PRO GLU

GAA TGT TTC TTA CAA CAC AAG GAC GAC AAC CCA AAC TTG CCA AGA TTG GTT AGA CCA GAA
                           ↳ HSA5

-continued
Scheme 8
Designed DNA sequence to code for mature HSA

120/358

VAL ASP VAL MET CYS THR ALA PHE HIS ASP ASN GLU GLU THR PHE LEU LYS LYS TYR LEU

GTC GAC GTT ATG TGT ACT GCT TTC CAC GAC AAC GAA GAG ACT TTC TTG AAG AAG TAC TTG
↳ HSA6

140/418

TYR GLU ILE ALA ARG ARG HIS PRO TYR PHE TYR ALA PRO GLU LEU LEU PHE PHE ALA LYS

TAC GAA ATC GCC AGA AGA CAC CCA TAC TTC TAC GCT CCA GAA TTG TTG TTC TTC GCT AAG
↳ HSA7

160/478

ARG TYR LYS ALA ALA PHE THR GLU CYS CYS GLN ALA ALA ASP LYS ALA ALA CYS LEU LEU

AGA TAC AAG GCT GCT TTC ACT GAA TGT TGT CAA GCT GCC GAC AAG GCT GCT TGT TTG TTG

180/538

PRO LYS LEU ASP GLU LEU ARG ASP GLU GLY LYS ALA SER SER ALA LYS GLN ARG LEU LYS

CCA AAG TTG GAC GAA TTG AGA GAC GAA GGT AAG GCT TCT TCC GCT AAG CAA AGA TTG AAG
↳ HSA8

200/598

CYS ALA SER LEU GLN LYS PHE GLY GLU ARG ALA PHE LYS ALA TRP ALA VAL ALA ARG LEU

TGT GCT TCC TTG CAA AAG TTC GGT GAA AGA GCC TTC AAG GCC TGG GCT GTT GCT AGA TTG
↳ HSA9

220/658

SER GLN ARG PHE PRO LYS ALA GLU PHE ALA GLU VAL SER LYS LEU VAL THR ASP LEU THR

TCT CAA AGA TTC CCA AAG GCT GAA TTT GCT GAA GTT TCT AAG TTG GTT ACT GAC TTG ACT
↳ HSA10

240/718

LYS VAL HIS THR GLU CYS CYS HIS GLY ASP LEU LEU GLU CYS ALA ASP ASP ARG ALA ASP

AAG GTT CAC ACT GAA TGT TGT CAC GGT GAC TTG TTG GAA TGT GCT GAC GAC AGA GCT GAC
↳ HSA11

260/778

LEU ALA LYS TYR ILE CYS GLU ASN GLN ASP SER ILE SER SER LYS LEU LYS GLU CYS CYS

TTG GCT AAG TAT ATC TGT GAA AAC CAA GAC TCT ATC TCT TCT AAG TTG AAG GAA TGT TGT

HSA12

280/838

GLU LYS PRO LEU LEU GLU LYS SER HIS CYS ILE ALA GLU VAL GLU ASN ASP GLU MET PRO

GAA AAG CCA TTG TTG GAA AAG TCT CAC TGT ATC GCT GAA GTT GAA AAC GAC GAA ATG CCA

HSA13

300/898

-continued
Scheme 8
Designed DNA sequence to code for mature HSA

ALA ASP LEU PRO SER LEU ALA ALA ASP PHE VAL GLU SER LYS ASP VAL CYS LYS ASN TYR

GCT GAC TTG CCA TCT TTG GCT GCT GAC TTC GTT GAA TCT AAG GAC GTT TGT AAG AAC TAC

320/958

ALA GLU ALA LYS ASP VAL PHE LEU GLY MET PHE LEU TYR GLU TYR ALA ARG ARG HIS PRO

GCT GAA GCT AAG GAC GTT TTC TTG GGT ATG TTC TTG TAC GAA TAC GCT AGA AGA CAC CCA
↳ HSA14

340/1018

ASP TYR SER VAL VAL LEU LEU LEU ARG LEU ALA LYS THR TYR GLU THR THR LEU GLU LYS

GAC TAC TCC GTT GTT TTG TTG TTG AGA TTG GCT AAG ACT TAC GAA ACT ACT TTG GAA AAG
↳ HSA15

360/1078

CYS CYS ALA ALA ALA ASP PRO HIS GLU CYS TYR ALA LYS VAL PHE ASP GLU PHE LYS PRO

TGT TGT GCT GCT GCT GAC CCA CAC GAA TGT TAC GCT AAG GTT TTC GAC GAA TTT AAG CCA
↳ HSA16

380/1138

LEU VAL GLU GLU PRO GLN ASN LEU ILE LYS GLN ASN CYS GLU LEU PHE LYS GLN LEU GLY

TTG GTT GAA GAA CCA CAA AAC TTG ATT AAG CAA AAC TGT GAA TTG TTC AAG CAA TTG GGT
↳ HSA17

400/1198

GLU TYR LYS PHE GLN ASN ALA LEU LEU VAL ARG TYR THR LYS LYS VAL PRO GLN VAL SER

GAA TAC AAG TTC CAA AAC GCT TTG TTG GTT AGA TAC ACT AAG AAG GTT CCA CAA GTC TCC

420/1258

THR PRO THR LEU VAL GLU VAL SER ARG ASN LEU GLY LYS VAL GLY SER LYS CYS CYS LYS

ACT CCA ACT TTG GTT GAA GTC TCT AGA AAC TTG GGT AAG GTT GGT TCT AAG TGT TGT AAG
↳ HSA18

440/1318

HIS PRO GLU ALA LYS ARG MET PRO CYS ALA GLU ASP TYR LEU SER VAL VAL LEU ASN GLN

CAC CCA GAA GCT AAG AGA ATG CCA TGT GCT GAA GAC TAC TTG TCT GTT GTT TTG AAC CAA
↳ HSA19

460/1378

LEU CYS VAL LEU HIS GLU LYS THR PRO VAL SER ASP ARG VAL THR LYS CYS CYS THR GLU

TTA TGT GTT TTG CAC GAA AAG ACT CCA GTT TCT GAC AGA GTT ACT AAG TGT TGT ACT GAA
↳ HSA20

480/1438

SER LEU VAL ASN ARG ARG PRO CYS PHE SER ALA LEU GLU VAL ASP GLU THR TYR VAL PRO

-continued
Scheme 8
Designed DNA sequence to code for mature HSA

TCT TTG GTT AAC AGA AGA CCA TGT TTC TCT GCC TTG GAA GTT GAC GAA ACT TAC GTC CCA
↳ HSA21

500/1498

LYS GLU PHE ASN ALA GLU THR PHE THR PHE HIS ALA ASP ILE CYS THR LEU SER GLU LYS

AAG GAA TTT AAC GCT GAA ACT TTC ACT TTC CAC GCC GAC ATC TGT ACC TTG TCC GAA AAG
↳ HSA22

520/1558

GLU ARG GLN ILE LYS LYS GLN THR ALA LEU VAL GLU LEU VAL LYS HIS LYS PRO LYS ALA

GAA AGA CAA ATC AAG AAG CAA ACT GCT TTG GTT GAA TTG GTT AAG CAC AAG CCA AAG GCT
↳ HSA23

540/1618

THR LYS GLU GLN LEU LYS ALA VAL MET ASP ASP PHE ALA ALA PHE VAL GLU LYS CYS CYS

ACT AAG GAA CAA TTG AAG GCT GTT ATG GAC GAC TTC GCT GCT TTC GTT GAA AAG TGT TGT

560/1678

LYS ALA ASP ASP LYS GLU THR CYS PHE ALA GLU GLU GLY LYS LYS LEU VAL ALA ALA SER

AAG GCT GAC GAC AAG GAA ACT TGT TTC GCT GAA GAA GGT AAG AAG TTG GTT GCT GCT TCT
↳ HSA24

580/1738

GLN ALA ALA LEU GLY LEU ... ...

CAA GCT GCT TTG GGT TTG TAA TAG

Note: The positions of the single-stranded, chemically synthesized oligodeoxyribonucleotides-as starting materials for the whole assembly-are shown in this sequence with arrows (e.g. ↳ HSA 1, HSA 2 . . . ) Note also that all HSA oligonucleotides were prepared with an extra GGCC 3'-terminal sequence and in addition, with an extra GGTAC 5'-terminal sequence in case of HSA 7, HSA 13 and HSA 19 oligonucleotides.

Scheme 9
Chemically synthesized HSA oligonucleotides comprising HSA II, III, IV and V large fragments Number of fragments: 24

| HSA oligo-nucleotide number | length | Position in mature HSA-coding sequence | Sequence |
|---|---|---|---|
| HSA 1 | 76 | 41–112 | TAGGTGAAGAAAACTTCAAGGCTTTTGGTTTTGATTGCTTTCGCTCAATACTTGCAACAATGTCCATTCGAAGGGCC |
| HSA 2 | 77 | 113–185 | ACCACGTCAAGTTGGTCAACGAAGTTACTGAATTTGCTAAGACCCTGTGTTGCTGACGAATCTGCTGAAAACTGGGCC |
| HSA 3 | 75 | 186–256 | TGACAAGTCCTTGCACACTTTGTTCGGTGACAAGTTGTGTACTGTTGCTACTTTGAGAGAAACTTACGGTGGGCC |
| HSA 4 | 70 | 257–322 | AAATGGCTGACTGTTGTGCTAAACAGGAACCAGAAAAGAACGAATGTTTCTTACAACAAGGACGGGCC |
| HSA 5 | 76 | 323–394 | ACAACCCAAACTTGCCAAGATTGGTTAGACCAGAAGTCGACGTTATGTGTACTGCTTTCCACGACAACGAAGGGCC |
| HSA 6 | 82 | 395–472 | AGACTTTCTTGAAGAAGTACTTGTACGAAATCGCCCAGAAGACACCCATACTTCTACGCTCCAGAATTGTTGTTCTTCGGGCC |
| HSA 7 | 74 | 473–537 | GGTACCTAAGAGATACAAGGCTGCTTTCACTGAATGTTGTCAAGCTGCCGACAAGGCTTGTGTTTGTTGGGCC |
| HSA 8 | 76 | 538–609 | CCAAAGTTGGACGAATTGAGAGACGAAGGTAAGGCTTCTTCCGCTAAGCAAAGATTGAAGTGTGCTTCCTTGGGCC |

-continued

Scheme 9
Chemically synthesized HSA oligonucleotides comprising HSA II, III, IV and V large fragments Number of fragments: 24

| HSA oligonucleotide number | length | Position in mature HSA-coding sequence | Sequence |
|---|---|---|---|
| HSA 9 | 74 | 610–679 | CAAAAGTTCGGTGAAAGAGCCTTCAAGGCCTGGGCTGTTGCTAGATTGTCTCAAAGATTCCCAAAGGCTGGGCC |
| HSA 10 | 75 | 680–750 | AATTTGCTGAAGTTTCTAAGTTGGTTACTGACTTGACTAAGGTTCACACTGAATGTGTCACGGTGACTTGGGCC |
| HSA 11 | 76 | 751–822 | TTGGAATGTGCTGACAGAGCTGACTTGGCTAAGTATATCTGTGAAAACCAAGACTCTATCTCTTCTAAGGGCC |
| HSA 12 | 76 | 823–894 | TTGAAGGAATGTGTGAAAAGCCATTGTTGGAAAAGTCTCACTGTATCGCTGAAGTTGAAAACGACGAAATGGGCC |
| HSA 13 | 79 | 895–964 | GGTACCCAGCTGACTTGCCATCTTTGGCTGTGAATCTAAGGACGTTTCGTTGAATCTAAGGACGTTTGTAAGAACTACGCTGAAGGGCC |
| HSA 14 | 81 | 965–1041 | CTAAGGACGTTTTCTTGGGTATGTTCTTGTACGAATACGCTAGAAGACACCCAGACTACTCCGTTGTTTGTTGTTGGGCC |
| HSA 15 | 79 | 1042–1116 | AGATTGGCTAAGACTTTACGAAAACTACTTTGGAAAAGTGTTGTGCTGCTGACCCACACGAATGTTACGCTAAGGGCC |
| HSA 16 | 76 | 1117–1188 | GTTTTCGACGAATTTAAGCCATTGGTTGAAGAACCACAAAACTTGATTAAGCAAAACTGTGAATTGTTCAAGGGCC |

-continued

Scheme 9
Chemically synthesized HSA oligonucleotides comprising HSA II, III, IV and V large fragments Number of fragments: 24

| HSA oligo-nucleo-tide number | length | Position in mature HSA-coding sequence | Sequence |
|---|---|---|---|
| HSA 17 | 85 | 1189–1269 | CAATTGGGTGAATACAAGTTCCAAAACGCTTTGTTGGTTAGATACACTAAGAAGTTCCACAAGTCTCCACTCCAACTTT GGGCC |
| HSA 18 | 73 | 1270–1338 | GTTGAAGTCTCTAGAAACTTGGGTAAGGTTGGTTCTAAGTGTGTAAGCACCCAGAAGCTAAGAGAATGGGCC |
| HSA 19 | 69 | 1339–1398 | GGTACCCATGCTGAAGACTACTGTGTCTGTTGTTTTGAACCAATTATGTGTTTTGCACGAAAAGGGCC |
| HSA 20 | 74 | 1399–1468 | ACTCCAGTTTCTGACAGAGTTACTAAGTGTTGTACTGAATCTTTGGTTAACAGAAGACCATGTTTCTCTGGGCC |
| HSA 21 | 77 | 1469–1541 | CCTTGGAAGTTGACGAAACTTACGTCCCAAAGGAATTTAACGCTGAAACTTTCACTTTCCACGCCGACATCTGGGCC |
| HSA 22 | 77 | 1542–1614 | TACCCTTGTCCGAAAAGGAAACAATTGAAGGCTGTTATGGACGACTTCGTTGAATTGGTTAAGCACAAGCCAAAGGGCC |
| HSA 23 | 77 | 1615–1687 | GCTACTAAGGAACAATTGAAGGCTGTTATGGACGACTTCGCTTTCGTTGAAAAGTGTTGTAAGGCTGACGGGCC |
| HSA 24 | 78 | 1688–1761 | ACAAGGAAACTTGTTTCGCTGAAGAAGGTAAGAAGTTGGTTGCTGCTTCTCAAGCTGCTTTGGGTTTGTAATAG GGCC |

Chemically synthesized HSA oligonucleotides. Lengths are given together with the 3'-terminal extra GGCC and with the 5'-terminal extra GGTAC (for HSA 7, 13 and 19) sequences.

Synthetic primers used to sequence parts of the HSA gene

When HSA oligonucleotides were cloned into pUC19 vector, (or another HSA nucleotide cloned into a previously obtained PHSA vector), a sequencing primer GTAACGC-CAGGGTTTTCCCAGT synthesized previously and named as pKO primer I (A. Simoncsits, M. Kálmán, I. Cserpán and C. Kari, Nucleic Acids Res. Symp. Ser. No 14, 1984, 321–322) was used to check the sequence of the clones obtained. This primer is located between nucleotide positions 348–369 of the published pUC19 sequence [Yanisch-Perron, C., Vieira, J. and Messing, J. Gene, 33 (1985) 103–119], and used to sequence all of the individually cloned HSA oligonucleotides (all 24).

When HSA II and HSA III large fragments were joined, the joining point was checked by a synthetic primer GCAGCCTTGTCGGCAGCTTG, which is complementary to the HSA gene sequence between nucleotide positions 508–527 (for mature HSA).

HSA IV and HSA V junction was checked by using CGTGCAAAACACATAATTGG primer which is complementary to HSA gene sequence between positions 1374–1393. Junction of HSA III and IV large fragments in PHSA (II-V) was checked by using HSA 10 oligonucleotide itself as a sequencing primer.

When the HSA gene synthesis is completed in pUC19 vector the whole HSA coding region was sequenced using plasmid template and 10 different sequencing primers. Further confirmation of the HSA coding sequence was obtained when it was replaced from the pUC19 vector into M13mp19 vector (Yanisch-Perron, C. etc) and sequencing was performed on single-stranded phage DNA template using the same 10 primers.

Synthetic primers to check the whole HSA coding region either in pUC19 or in M13mp19

| primer name | nucleotide position in the HSA coding region |
| --- | --- |
| pKO primer I | outside of HSA, in the lacZ part of pUC19 |
| pHSA primer 1 | 1587–1603 |
| pHSA primer 2 | 1398–1414 |
| pHSA primer 3 | 1195–1211 |
| pHSA primer 4 | 988–1007 |
| pHSA primer 5 | 795–809 |
| pHSA primer 6 | 582–597 |
| pHSA primer 7 | 382–398 |
| pHSA primer 8 | 178–192 |
| pHSA primer 9 | 66–85 |

The last primer (primer 9) was also used to check the junction of the HSA (mature or Met-form) and the yeast PHO5 promoter-signal sequence when the HSA gene was replaced from pUC19 into pPT2HK$_1$

| MATERIALS AND METHODS | |
| --- | --- |
| Enzymes | Source |
| ApaI | Boehringer |
| EcoRI | New England Biolabs (NEB) |
| Klenow polymerase | Boehringer |
| T4 DNA ligase | NEB |
| KpnI | NEB |
| SacI | NEB |
| BamHI | Boehringer |
| XbaI | NEB |
| mung bean nuclease | Pharmacia |
| Hind III | NEB |
| Sau3AI | NEB |
| BalI | NEB |
| PstI | NEB |
| XhoI | Boehringer |
| T4 polynucleotide kinase | Boehringer |
| T1 RNase | Calbiochem |
| Proteinase K | Merck |
| BclI | NEB |
| SalI | NEB |
| Helicase | REACTIFS IBF |
| Glucuronidase | Boehringer |

Isotopes
$\gamma$-$^{32}$P-ATP (<5000 Ci/mmol)
$\alpha$-$^{32}$P-dATP (800 Ci/mmol)
$\alpha$-$^{35}$S-dATP (~1200 (Ci/mmol) were from Amersham
$^{35}$S-methionine (~800 Ci/mmol) were from Amersham Chemical Synthesis of Oligodeoxyribonucleotides Either the phosphate-triester method was used with the help of a manual DNA bench synthesizer (Omnifit), using monomer or/and dimer building blocks (Sproat B. S. et al 1983, Tetrahedron Letters 24, 5771), or the phosphoramidite method using an automatic Gene Assembler (Pharmacia) according to the manufacturers Manual. Chemicals were obtained either from Cruachem (phosphate-triester chemistry) or from Pharmacia (phosphoramidite chemistry).

5'-phosphorylation of the synthetic oligodeoxyribonucleotides

Enzymatic phosphorylation was performed by using T4 polynucleotide kinase and ATP. Depending on the specific requirements, this reaction was performed with either radioactive or non-radioactive ATP.

a) Phosphorylation with $\gamma$-$^{32}$P-ATP of high specific activity

This procedure was used for HSA oligonucleotides to obtain hybridization probes or for 5'-labeling of the sequencing primers when the sequencing reactions were carried out on plasmid DNA template. 10 pmol oligonucleotide was dissolved in $\gamma$-$^{32}$P-ATP (7 µl, ~5000 Ci/mmol, 10 mCi/ml) 250 mM Tris-HCl pH 7.5–50 mM MgCl$_2$ (2 µl) and 100 mM DTT (1 µl). 0.5 µl T4 polynucleotide kinase (10 U/µl) was added and the mixture was kept at 37° C. for 30 min followed by heat treatment (100° C., 3 min) to inactivate the enzyme. The solution was diluted according to the further use with either hybridization buffer or with sterile water. The excess of non-reacted $\gamma$-$^{32}$P-ATP was not removed.

b) Phosphorylation with $\gamma$-$^{32}$P-ATP of low specific activity

This procedure was employed to label the HSA oligonucleotides before their ligation with adapters.

50 pmol oligonucleotide and 100 pmol $\gamma$-$^{32}$P-ATP (200 Ci/mmol) were dissolved in 10 µl reaction volume containing 50 mM Tris-HCl pH 7.5, 10 mM MgCl$_2$ and 10 mM DTT, and 1 µl T4 polynucleotide kinase (10 U/µl) was added. After standing at 37° C. for 1 hr, the mixture was heat treated at 100° C. for 3 min.

c) Phosphorylation with non-radioactive ATP

This procedure was applied to: upper strand of adapter 1 and adapter 2, as well as for both strands of other adapter-like molecules like adapter 3 and HSA I fragment oligonucleotides.

Phosphorylation of the upper strand of adapter 1 and adapter 2 oligonucleotides was performed on large scale as follows.

2.2 nmol of oligonucleotide and 20 nmol ATP were dissolved in 100 µl reaction volume containing 50 mM Tris-HCl, pH 7.5, 10 mM $MgCl_2$, 10 mM DTT and 10 units of T4 polynucleotide kinase. Reaction was performed at 37° C. for 1 hr followed by heat treatment at 100° C. for 3 min.

Other non-radioactive phosphorylations were carried out essentially as it was described for the low specific activity phosphorylation on 50 pmol oligonucleotide scale but no radioactively labeled $\gamma$-$^{32}$P-ATP was added to the reaction mixture.

Ligation of HSA Oligonucleotides with Adapter
(General Procedure)

25 pmol of 5'-$^{32}$P-phosphorylated HSA oligonucleotide was mixed with 75 pmol of 5'-phosphorylated upper strand adapter oligonucleotide and with 75 pmol of non-phosphorylated lower strand adapter oligonucleotide in 50 $\mu$l reaction volume containing 50 mM Tris-HCl, pH 7.5, 10 mM $MgCl_2$, 10 mM DTT, 1 mM ATP. The mixture cooled to 15° C. and approx. 0.2 $\mu$l (approx. 80 units) of T4 DNA ligase was added. Reaction was performed at 15° C. for 4–16 hrs. 50 $\mu$l of 1M NaCl and 1 $\mu$l of yeast carrier tRNA (10 $\mu$g/$\mu$l) was added and the oligonucleotides were precipitated with 300 $\mu$l ethanol in liquid nitrogen bath for 2 min. The mixture was centrifuged at 12 000 rpm for 5 min, the pellet was dried and dissolved in 10 $\mu$l of gel loading buffer containing 80% formamide, 10 mM EDTA, 0.05% xylene cyanole and 0.05% bromophenol blue. Separation of the ligated HSA oligonucleotide from the non-ligated one (and from the adapter) was achieved by applying the above solution onto a 10% acrylamide gel containing no urea. Gel electrophoresis was carried out at 400 V for 3–5 hrs using 100 mM TBE as gel and running buffer (100 mM Tris, 100 mM boric acid, 2 mM EDTA, pH 8.3). After radioautography of the gel (2–10 min) 2 major radioactive bands were located, of which the lower band corresponded to the non-ligated HSA oligonucleotide while the upper band corresponded to the adapter-ligated HSA oligonucleotide. The gel piece corresponding to the latter was cut out and soaked in 50 mM NaCl (300 $\mu$l) at 37° C. for 10–16 hrs. The supernatant was treated twice with phenol (saturated with 50 mM Tris-HCl, pH 8.0, 300 $\mu$l) and the oligonucleotide-adapter adduct was precipitated after addition of 30 $\mu$l 3M NaOAc, pH 5.2, 1 $\mu$l yeast carrier tRNA (10 $\mu$g/$\mu$l) and 750 $\mu$l ethanol.

The pellet was washed with ethanol, dried and dissolved in 10 $\mu$l of sterile water, and an aliquot is counted (in a Packard liquid scintillation counter) to estimate the yield of the ligation reaction. The yield, based on the starting material $^{32}$P-phosphate HSA oligonucleotide, varied between 20–50% (isolated yield).

21 of the 24 HSA oligonucleotides were ligated with adapter 1. The exceptions are HSA 16, 17 and 18 oligonucleotides, which were ligated with adapter 2. (For HSA 16, this new adapter was obviously necessary, but perhaps it was not a better choice for HSA 17 and 18. Anyway, these three oligonucleotides were ligated at the same time with adapter 2).

Bacterial strains

Most of the HSA containing plasmid transformations and propagations were performed using JM101 E. coli(Messing, J. Crea, R. and Seeburg, P. H., Nucleic Acids Res. 9, (1981), 304–321). This strain has the following genotype: supE, thi, $\Delta$(lac-proAB), [F'. traD36, proAB, lacI$^q$Z$\Delta$M15].

A dam E. coli strain (GM2) (Morinus, M. G. and Morris, N. R. (1973) J. Bact. 114, 1143–1150) was used for plasmid propagation before BclI enzyme manipulation was required.

During pBY2/HSA No 1 and pBY2/HSA No 2 constructions an E. coli (K12) strain JF1754 strain (hsd R hsdM$^+$ lac gal met leu B his B) was used as host, references: Storms, R. K., McNeil, J. B., Khanendekar, P. S., An, G., Parker, J. and Friesen, J. D. (1979), J. Bacteriol. 140, 73–82; Kiss. G. B., Amin. A. A. and Perlman, R. E. (1981) Molecular and Cellular Biology, 1, 535–543.

The leu B and his B mutations of JF1754 can be complemented with the corresponding yeast genes (leu 2 and his 3, respectively), reference: Struhl, K. and Davis, R. W. (1980) J. Mol. Biol. 136, 309–332.

Yeast strain

AH220 [a, trp 1, leu 2-3, 2-112, his 3-11, 3-15, pho 5, pho 3] laboratory haploid strain was obtained from A. Hinnen, CIBA-CEIGY AG, Biotechnology Department, Basel, Switzerland.

E. Coli Transformation with Plasmid and Phage
Vectors

This was performed essentially as described by Hanahan, D. (in DNA Cloning, Vol I. Edited by Glover, D. M., IRC Press Limited 1985, pp 109–135) using frozen competent cells prepared according to Protocol 3 of this article.

Yeast transformation

Yeast spheroplasts prepared by helicase treatment of AH220 were transformed according to Hinnen et al (Hinnen, A., Hicks, J. B. and Fink, G. R. (1978) Proc. Natl. Acad. Sci: USA, 75, 1929–1933).

Plasmid preparation

We used the slightly modified version of the rapid alkaline extraction procedure (Birnboim, H. C. and Doly, J. (1979) Nucleic Acids Res., 7, 1513–1523) Minipreps:

Single colony was inoculated into 3 ml of LB-medium (Maniatis, T. Fritsch., E. F. and Sambrook, J. (1982) Molecular Cloning, Cold Spring Harbor Laboratory, N.Y. p 440) containing 100 $\mu$g/ml ampicillin and the culture was shaken at 37° C. for 10–18 hrs. Cells were harvested by centrifugation and resuspended in 100 $\mu$l of solution I (50 mM glucose, 25 mM Tris-HCl pH 8.0, 10 mM EDTA) and left at room temperature for 5 min. 200 $\mu$l of freshly prepared solution II (0.2N NaOH, 1% SDS) was added and the solution was briefly vortexed, then put on ice for 5 min. Ice-cold solution III (150 $\mu$l, 3M potassium acetate-2M acetic acid) was added and the mixture was briefly vortexed, then put on ice for 15 min. The mixture was centrifuged at 12000 rpm for 5 min and 400 $\mu$l of the supernatant was pipetted into a fresh tube. 800 $\mu$l of ethanol was added and the mixture was left to stand for 5 min, then spun at 12000 rpm for 2 min. The pellet was redissolved in 400 $\mu$l of 100 mM Tris-HCl, pH 8.0–50 mM NaOAc, pH 6.5, and 1 ml of 95% ethanol was added. After standing at −20° C. for 30 min, the mixture was spun at 12000 rpm for 2 min. The pellet was dried and dissolved in 100 $\mu$l of 10 mM Tris-HCl, pH 8.0–1 mM EDTA solution containing 0.5 U of $T_1$RNase, and the solution was kept at 37° C. for 30 min, then extracted with 100 $\mu$l of phenol saturated with 50 mM Tris-HCl, pH 8.0. The aqueous phase was taken (approx 90 $\mu$l), 10 $\mu$l of 3M sodium acetate pH 5.2 was added followed by 260 $\mu$l of 95% ethanol and quick cooling of the mixture in liquid nitrogen bath. After centrifugation (12 000 rpm, 3 min) the pellet was redissolved in 200 $\mu$l of 0.3M NaOAc, pH 5.2 and 500 $\mu$l of 95% EtOH was added to precipitate the nucleic acid as above (quick chilling in liquid nitrogen bath followed by centrifugation). The pellet was washed with 1 ml of 95% EtOH, dried and dissolved in 30 $\mu$l of sterile water.

The yield of the plasmid DNA was estimated as 3–5 $\mu$g. For agarose gel electrophoresis and restriction analysis, 1–2 $\mu$l of the above solution was used, while 3 $\mu$l was used for sequencing reactions. When the above obtained plasmid was used for further cloning experiment 20 µl solution was taken for the linearisation with one or usually with two enzymes followed by linear vector isolation.

Restriction Enzyme Cleavage of Plasmid DNA

All the analytical restriction analyses were performed according to the manufacturers recommendations except for that BSA was always omitted from the reaction buffers.

When a particular plasmid is cleaved on preparative scale with one or more enzymes simultaneously or sequentially reaction conditions are always given.

pUC19 cleavage with two different restriction enzymes

Generally, the first HSA oligonucleotides of the large HSA fragments (II, III, IV and V) are cloned into pUC19 vector cleaved with two different enzymes. According to this original plan, only HSA 1, HSA 7, HSA 13 and HSA 19 oligonucleotides, ligated previously with an adapter (adapter 1) are cloned into pUC19. During the gene assembly work, however, it turned out to be more advantageous (or quicker) to clone two more HSA oligonucleotides, namely HSA 4 and HSA 17, into pUC19 rater than into the corresponding intermediate pHSA vectors.

a) pUC19 cleavage with PstI and EcoRI

2 µg of pUC19 was treated in 100 µl of high salt buffer (100 mM NaCl, 50 mM Tris-HCl, pH 7.5, 10 mM $MgCl_2$, 1 mM DTT) with 20 units of PstI and 20 units of EcoRI at 37° C. for 4 hrs. DNA was ethanol precipitated by adding 5 µl of 3M sodium acetate, pH 5.2 and 300 µl of ethanol, chilling the mixture for 2 min in liquid nitrogen bath followed by centrifugation at 12000 rpm for 3 min. The pellet was dried and dissolved in 60 µl of 4% Ficoll 400, 0.05% bromophenol blue and the linear vector was isolated after separation by electrophoresis on a 0.5% agarose gel in 40 mM Tris-acetate, 2 mM EDTA buffer (TAE buffer) followed by electroelution, phenol extraction and ethanol precipitation promoted by adding 10 µg of yeast carrier tRNA [Maniatis, T., Fritsch, E. F. and Sambrook, J. Molecular Cloning, Cold Spring Harbor Laboratory (1982) pp. 164–166]. The pellet obtained was dissolved in 10 µl of sterile water and the concentration of the linear vector was estimated by minigel method (ibid., pp. 468–469).

This vector was used for cloning: HSA 1 b) pUC19 cleavage with BamHI and EcoRI

2 µg of pUC19 was treated in 100 µl of high salt buffer with 20 units of BamHI and 20 units of EcoRI as above, and the isolation of the linear vector was performed essentially in the same way as described above. This vector was used for cloning: HSA 13, HSA 17.

c) pUC19 cleavage with XbaI and EcoRI

This was done using 20 units of XbaI and 20 units of EcoRI for 2 µg of pUC19 essentially as described above.

XbaI-EcoRI pUC19 vector was used for cloning: HSA 4, HSA 7, HSA 19.

Cleavage of the Intermediate pHSA Vectors With ApaI and EcoRI

20 µl of PHSA plasmid prepared as described before was made up to 100 µl reaction volume containing 6 mM Tris-HCl, pH 7.4, 6 mM NaCl, 6 mM $MgCl_2$, 1 mM DTT and 40 units of ApaI enzyme and the reaction mixture was kept at 37° C. A 2 µl sample was run on a 0.5% agarose gel in TBE buffer (89 mM Tris, 89 mM boric acid, 8 mM EDTA). When the cleavage seemed to be complete (after 1–4 hrs), 10 µl of 1M NaCl, 5 µl of 1M Tris-HCl, pH 7.5 and 20 units of EcoRI were added and the mixture was kept for further 4–16 hrs at 37° C. The linear vector DNA was precipitated with ethanol and purified on a 0.5% agarose gel as described before for linear pUC19 vector isolation.

This ApaI-EcoRI double digestion was performed with the following plasmids: pHSA 1, 2, 4, 5, 7, 8, 9, 10, 11, 13, 14, 15, 17, 19, 20, 21, 22, 23.

Cloning of HSA Oligonucleotide-Adapter Complexes Into pUC19 or Into pHSA Vectors General procedure:

Approx. 0.1 µg of double-cleaved pUC19 or pHSA vector was mixed with 5 pmol of HSA oligonucleotide-adapter complex in 10 µl reaction volume containing 50 mM Tris-HCl, pH 7.5, 10 mM $MgCl_2$, 10 mM DTT, 1 mM ATP and 80 units of T4 DNA ligase and the reaction mixture was kept at 15° C. for 4–16 hrs. The mixture was heated to 60° C. for 5 min and, after cooling to room temperature, 1 µl of 1 mM dNTP (containing all four deoxynucleoside 5'-triphosphates at 1 mM concentration) and 1 µl of 0.5 units/µl Klenow polymerase was added and the reaction mixture was left at room temperature for 15 min. It was then heated at 60° C. for 10 min and 4 µl of sterile water, 2 µl of a buffer containing 250 mM Tris-HCl, pH 7.5 and 50 mM $MgCl_2$, 1 µl of 100 mM DTT, 1 µl of 10 mM ATP and 200 units of T4 DNA ligase were added at 15° C. The reaction mixture was kept at 15° C. for 6–20 hrs and then transformed into frozen competent JM101 *E. coli* cells as referred earlier. The colonies obtained on LB plates containing 100 µg/ml ampicillin were picked onto LB-ampicillin master plate and onto nitrocellulose replica plate [Grunstein, M. and Hogness, D. (1975) Proc. Natl. Acad. Sci. USA 72, 3961]. The colonies grown up on the nitrocellulose replica plate were lysed and hybridized with the corresponding 5'-$^{32}$P-phosphate labeled HSA oligonucleotide probe [Maniatis, T., Fritsch, E. F. and Sambrook, J. Molecular Cloning (1982), Cold Spring Harbor Laboratory, pp. 314–325]. Usually 4–10 positive colonies were grown up in 3 ml of LB-ampicillin medium and plasmid DNA was prepared as described previously.

Dideoxy sequencing on plasmid template

The supercoil sequencing method [Chen, E. Y. and Seeburg, P. H. DNA 4, 165, (1985)] was performed with a few modifications. 3 µl of plasmid DNA prepared as before was mixed with 17 µl of 0.3M NaOH-0.3 mM EDTA at room temperature. After 5 min 3 µl of 2M ammonium acetate-acetic acid, pH 4.5 and 60 µl of ethanol were added and the mixture was kept at −80° C. for 15 min. The mixture was centrifuged (12 000 rpm, 5 min) and the pellet was washed with 70% EtOH, dried and dissolved in 10 µl of buffer containing 7 mM Tris-HCl, pH 7.5, 7 mM $MgCl_2$, 5 mM β-mercaptoethanol, 0.1 mM EDTA and 0.25 pmol of 5'-$^{32}$P-phosphate labeled sequencing primer (sequencing primers used during the work are shown in Scheme 10 and above. Sometimes one of the HSA oligonucleotides was also used as sequencing primer despite the fact that they contain a 3'-terminal GGCC extra sequence). The mixture was heated at 45° C. for 15 min. Then four 2 µl aliquots were pipetted into wells of a microtiter plate. 2 µl of each four dideoxy termination mixtures [Hong, G. F. Bioscience Reports, 2, 907 (1982)] and 2 µl of 0.25 units/µl Klenow polymerase were mixed with each of the four aliquoted primer-template and the mixtures were kept at room temperature for 20 min, then at 50° C. for 10 min. To each reaction mixture 3 µl of gel loading buffer containing 80% formamide, 10 mM EDTA, 0.05% bromophenol blue and 0.05% xylene cyanol was added and the mixtures were heated at 100° C. for 2 min. Gel electrophoresis was carried out on a 6% acrylamide gel containing 8M urea, 90 mM Tris, 90 mM boric acid, 2 mM EDTA, pH 8.3.

Cloning the Individual HSA Oligonucleotides
(HSA 1, 2, . . . 24)

The original plan was the following:

The whole HSA coding region was divided into five fragments, HSA I, II, III, IV and V. The latter four fragments (II, III, IV and V) were further divided into 6—6 single-stranded oligonucleotides (each ending at the 3'-terminus with G and supplied with an extra GGCC sequence by chemical synthesis), altogether 24 oligonucleotides. The HSA large fragments (II, III, IV and V) were to be obtained by consecutive clonings of the synthetic, single-stranded HSA 16 oligonucleotide could only be cloned with the help of a new adapter (adapter 2)

HSA 17 oligonucleotide could not be cloned into pHSA (13-16) so that the expected pHSA (13-17) be obtained. Although HSA 17 sequence was found in the obtained plasmids, deletions in the previously cloned regions were observed. So HSA 17 was cloned into pUC19.

HSA 18 oligonucleotide was cloned into pHSA 17 with the help of adapter 2

HSA IV large fragment was obtained from the previously cloned HSA (13-16) and HSA (17-18) DNA segments.

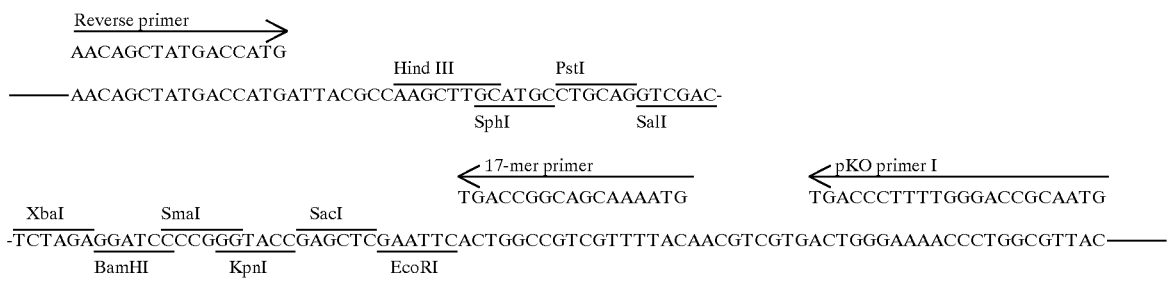

Scheme 10
Polycloning region of pUC19 (or M13 mp 19) together with the sequencing primers Primer references, Reverse primer: Hong, G.F. (1981) Biosciene Reports 1, 243–252
             17-mer primer: Duckworth, M.L., Gait, M.J., Goelet, P., Hong, G.F., Singh, M. and Titmas,
                            R.C. (1981), Nucleic Acids Res. 9, 1691–1706
             pKO primer I: Simoncsits, A., Kálmán, M. Cserpán, I. and Kari, C. (1984) Nucleic Acids
                           Res. Symp. Ser. No 14, 321–322 oligonucleotides (with the help of an adapter) into pUC19 or pUC19 derived pHSA vectors, exemplified here with pHSA II:

| | |
|---|---|
| HSA 1 is cloned into pUC19 to obtain | pHSA 1 |
| HSA 2 is cloned into pHSA 1 to obtain | pHSA (1-2) |
| HSA 3 is cloned into pHSA (1-2) to obtain | pHSA (1-3) |
| HSA 4 is cloned into pHSA (1-3) to obtain | pHSA (1-4) |
| HSA 5 is cloned into pHSA (1-4) to obtain | pHSA (1-5) |
| HSA 6 is cloned into pHSA (1-5) to obtain | pHSA (1-6), or pHSA II. |

Similarly, pHSA III was obtained from HSA 7, 8, 9, 10, 11, 12 oligonucleotides. pHSA IV was obtained from HSA 13, 14, 15, 16, 17, 18 oligonucleotides. pHSA V was obtained from HSA 19, 20, 21, 22, 23, 24 oligonucleotides.

This general strategy was usually employed for cloning HSA oligonucleotides with the help of adapter 1 (see Scheme 3), but we deviated from this in a few cases. The reasons to do so were either to speed up the assembly work by parallel cloning of more than one oligonucleotide within a large fragment (like in case of HSA II) or to solve cloning problems we encountered during the work.

These exemptions are:

HSA 1 oligonucleotide could be cloned as a whole only with the help of a partial duplex (at the 5'-terminus of HSA 1)

HSA II large fragment was obtained as pHSA II from the previously cloned HSA (1-3) and HSA (4-6) DNA segments HSA 15 oligonucleotide could only be cloned to obtain the correct sequence with the help of a complementary oligonucleotide, which covered nearly ⅔ part of the original HSA 15

Cloning HSA 1 into pUC19

When HSA 1 oligonucleotide ligated with adapter 1 (HSA 1+$A_1$) was tried to be cloned into BamHI-EcoRI cleaved pUC19 by the cloning procedure described in details before, the complete HSA 1 region was not obtained in cloned form. About 50 clones hybridizing with 5'-$^{32}$P-labeled HSA 1 oligonucleotide were sequenced, and it was found that most of the clones lacked the 5'-terminal T residue of HSA 1 (the rest of them lacked more than one residue).

A new strategy was used then to get the whole HSA 1 cloned as follows. PstI-EcoRI cleaved pUC19 was used as a cloning vector and a synthetic, partial duplex having a PstI sticky end at the 5'-terminus and a 10 nucleotide long 5'-protruding region at its 3'-terminus, which latter region is complementary to the 5'-terminal region of HSA 1, was included in the reaction mixture. The use of this "helper duplex" is shown in Scheme 11.

0.1 μg of PstI-EcoRI cleaved pUC19 vector was mixed with 5 pmol of HSA 1+$A_1$, 5 pmol of 5'-phosphorylated GTGCGATC and 5 pmol of 5'-phosphorylated TCTTCAC-CTAGATCGCACTGCA in 10 μl reaction volume and the whole cloning procedure was performed essentially as described in the general procedure.

100 colonies were checked by hybridization with 5'-$^{32}$P-labeled HSA 1 oligonucleotide as a probe. Of the 29 positive clones, 10 were used for sequencing with the help of the pKO primer I and the reverse primer. 8 of the 10 sequenced clones contained the correct sequence. Plasmid DNA of one of the proper clones was used in the next step as pHSA 1 for ApaI-EcoRI double digestion and for cloning the HSA 2 oligonucleotide.

Scheme 11

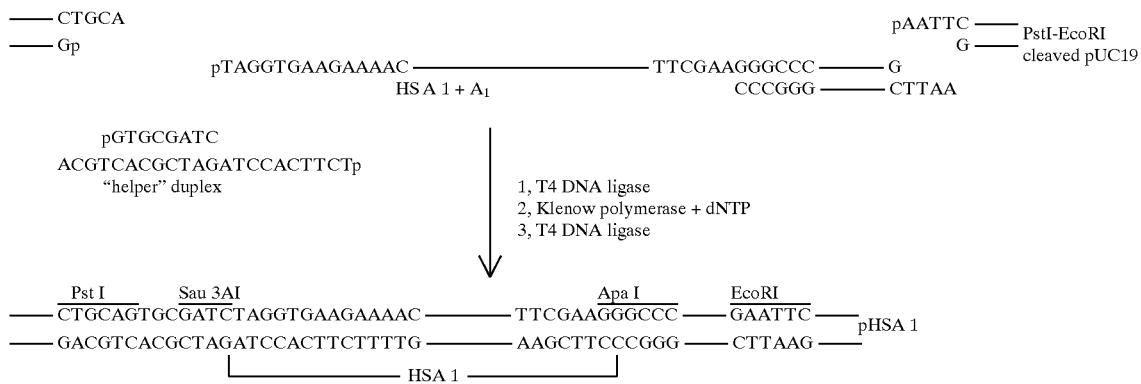

Cloning HSA 2 into pHSA 1

0.1 μg of ApaI-EcoRI cleaved pHSA 1 was mixed with 5 pmol of HSA 2+A$_1$ in 10 μl reaction volume and the cloning steps were performed as described above. (Scheme 12).

40 colonies were replica plated and hybridized with 5'-$^{32}$P-HSA 2 oligonucleotide as a probe. 9 positive colonies were obtained, plasmid DNA prepared from them and they were sequenced using pKO primer I. 5 clones contained the correct HSA 2 sequence. Plasmid DNA from one of the correct clones [PHSA (1-2)] was used in the next step to clone HSA 3 oligonucleotide.

Cloning HSA 3 into pHSA (1-2)

0.1 μg of ApaI-EcoRI cleaved pHSA (1-2) was reacted with 5 pmol of HSA 3+A$_1$ in 10 μl reaction volume as described before (Scheme 13).

187 colonies were replica plated and hybridized with 5'-$^{32}$P-HSA 3 oligonucleotide probe. Of the 42 positive clones, 10 were used for preparing plasmid DNA and they were sequenced using pKO primer I. 1 clone was correct and the plasmid prepared from it was called pHSA (1-3).

PHSA (1-3) was used later to clone HSA (4-6) DNA segment (see later).

Scheme 12-Cloning HSA 2 into pHSA 1

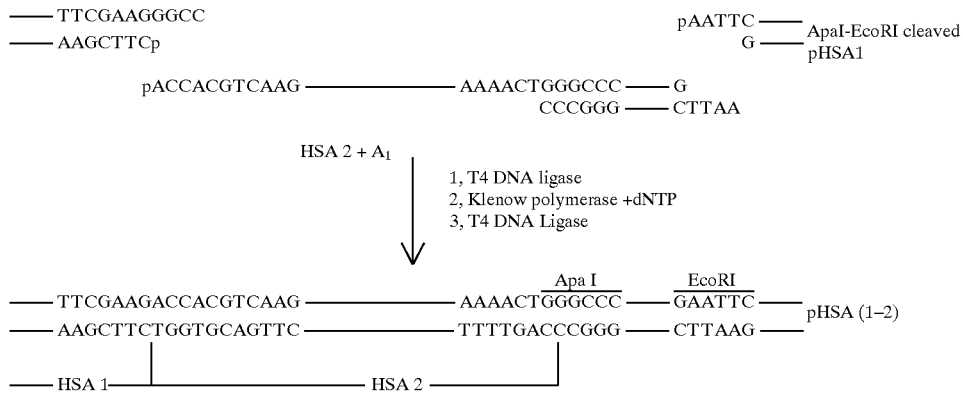

Scheme 13

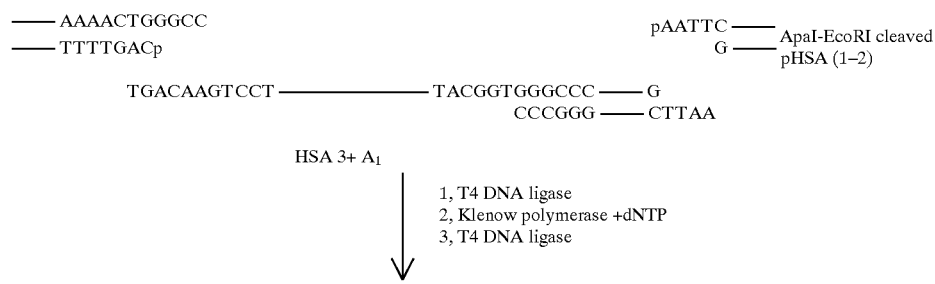

-continued
Scheme 13

Cloning HSA 4 into pUC19

0.1 μg of XbaI-EcoRI cleaved pUC19 and 5 pmol of HSA 4+$A_1$ were reacted in 10 μl reaction volume as described before (Scheme 14)

110 colonies were picked and 45 of them showed hybridization with 5'-$^{32}$P-HSA 4 oligonucleotide probe. Plasmid DNA was prepared from 4 positive clones, they were sequenced using pKO primer I, and all of them were found to contain the correct HSA 4 sequence as well as the expected flanking regions. The pHSA 4 obtained so contained the regenerated XbaI site at the 5'-terminus of HSA 4, which could later be eliminated at the junction point between HSA 3 and HSA 4 oligonucleotides.

pHSA 4 was used to clone HSA 5 in the next step.

Cloning HSA 5 into pHSA 4

0.1 μg of ApaI-EcoRI cleaved pHSA 4 and 5 pmol of HSA 5+$A_1$ were reacted according to the general procedure (Scheme 15).

65 colonies were hybridized with 5'-$^{32}$P-HSA 5 probe and 3 of them proved to be positive. Plasmid DNA was prepared from the positive clones and one of them was correct, this was called pHSA (4-5) and was used to clone HSA 6 in the next step.

Scheme 14

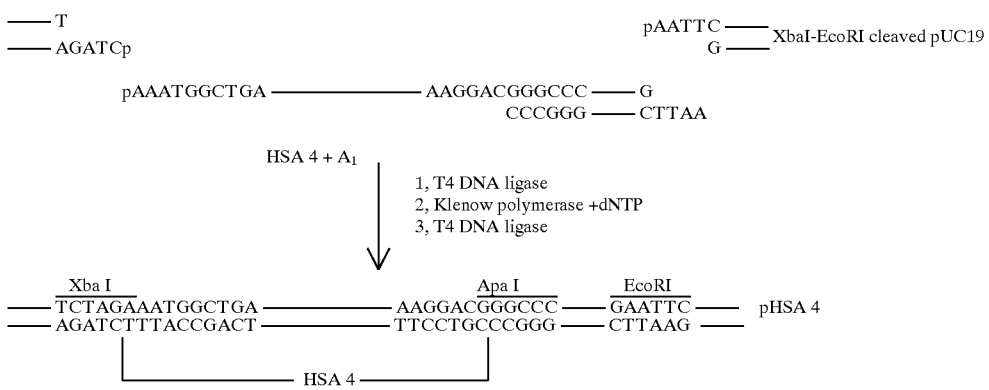

Scheme 15

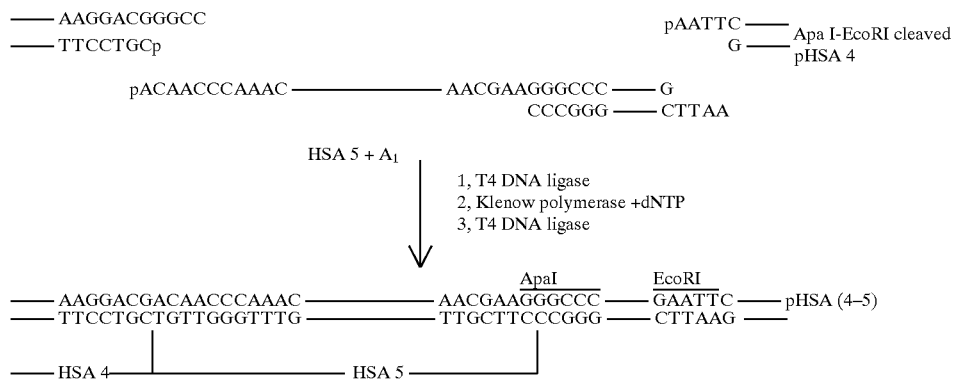

Cloning HSA 6 into pHSA (4-5)

0.1 μg of ApaI-EcoRI cleaved pHSA (4-5) and 5 pmol of HSA 6+A$_1$ were reacted according to the general procedure (Scheme 16).

225 colonies were replicated and hybridized with 5'-$^{32}$P-HSA 6 oligonucleotide probe. 72 proved to be positive and 10 of the latter were used to prepare plasmid DNA. Of the 10 sequenced (using pKO primer I) plasmids 2 contained the correct HSA 6 sequence, one of these plasmids was called pHSA (4-6).

pHSA (4-6) was used later to obtain HSA (4-6) DNA segment which was cloned into pHSA (1-3) to obtain pHSA (1-6), or pHSA II.

10 randomly picked white colonies were inoculated into LB-ampicillin medium and plasmid DNA prepared from them were sequenced using pKO primer I. 7 of them contained the correct HSA sequence, one of them was used later as pHSA 7 to clone HSA 8 in the next step.

HSA 7 oligonucleotide as the first oligonucleotide of HSA III fragment, contains an extra GGTAC 5'-terminal sequence, which was introduced in order to be able to use this sequence, forming a KpnI site together with the next C residue, to join HSA III large fragment with HSA II large fragment. This extra sequence should disappear after performing the relevant reactions, so this sequence is not

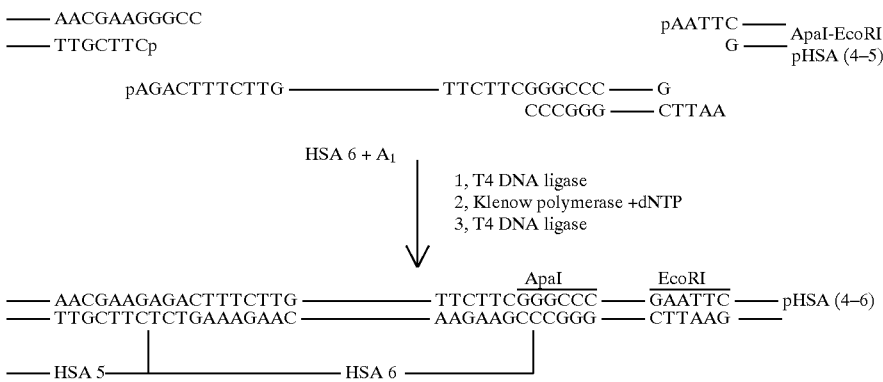

Scheme 16

Cloning HSA 7 into pUC19

0.1 μg of XbaI-EcoRI cleaved pUC19 and 5 pmol of HSA 7+A$_1$ were reacted according to the general procedure (Scheme 17).

The HSA 7 containing clones were selected according to a color reaction. After transformation, the transformed cells were plated in the presence of IPTG (IPTG: isopropyl-β-D-thiogalactopyranoside) and X-gal (X-gal: 5-bromo-4-chloro-3-indoyl-β-galactoside) [Vieira, J. and Messing, J. (1982) Gene 19, 259–268]. White colonies in blue background were expected to contain the correct HSA sequence.

included as a part of HSA 7 when it is already cloned in PHSA 7 as shown in Scheme 17.

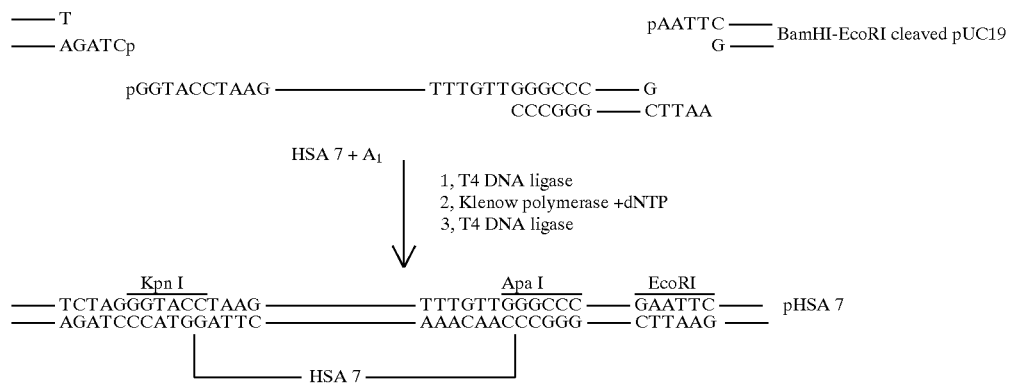

Scheme 17

Cloning HSA 8 into pHSA 7

0.1 μg of ApaI-EcoRI cleaved pHSA 7 was reacted with 5 pmol of HSA 8+A$_1$ according to the general procedure (Scheme 18).

240 colonies were tested by hybridization probe 5'-$^{32}$P-HSA 8 and 6 of them were postive. 2 of them revealed the correct HSA 8 sequence after sequencing with pKO primer I. Plasmid DNA of a correct clone was carried through the general cloning strategy as pHSA (7-8) to clone HSA 9 in the next step.

Scheme 18

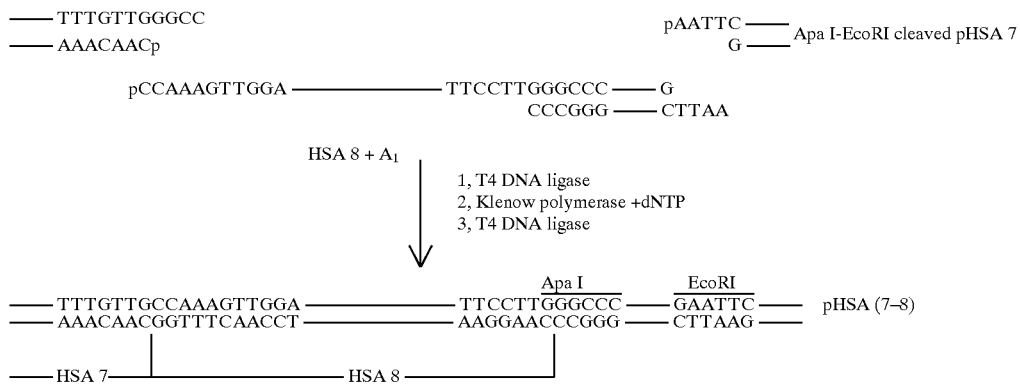

Cloning HSA 9 into pHSA (7-8)

0.1 μg of ApaI-EcoRI cleaved pHSA (7-8) and 5 pmol of HSA 9+$A_1$ were reacted according to the general procedure (Scheme 19).

240 colonies were replica plated and hybridized with 5'-$^{32}$P-HSA 9 oligonucleotide probe. Plasmid DNA was prepared of 8 of the 13 positive clones and sequenced. 3 of the 8 sequenced clones contained the correct pHSA (7-9) plasmid.

Cloning HSA 10 into pHSA (7-9)

0.1 μg of ApaI-EcoRI cleaved pHSA (7-9) and 5 pmol of HSA 10+$A_1$ were reacted in the usual way (Scheme 20).

Of 202 colonies 58 showed hybridization with 5'-$^{32}$P-HSA 10 oligonucleotide probe. 10 positive clones were used to prepare plasmid DNA for sequencing and 8 of them contained the proper PHSA (7-10).

Scheme 19

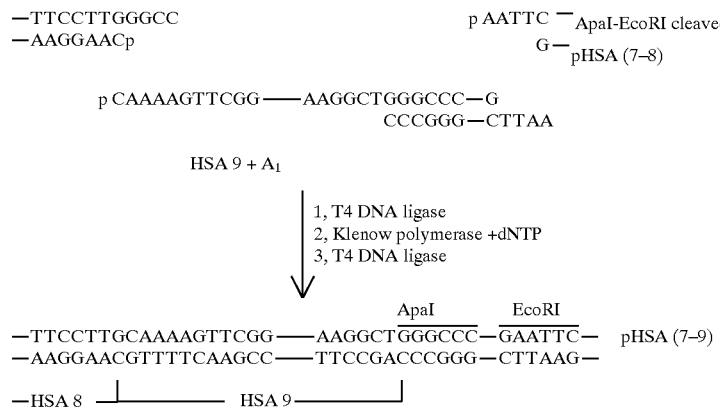

Scheme 20

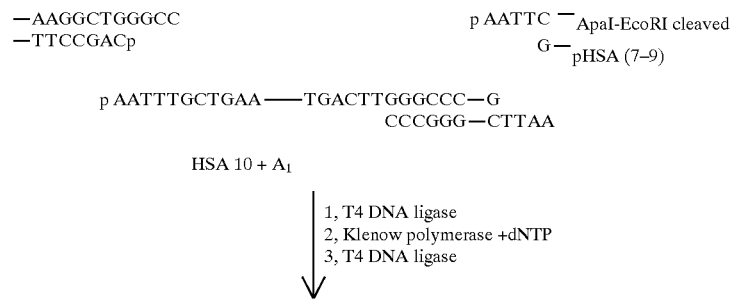

-continued
Scheme 20

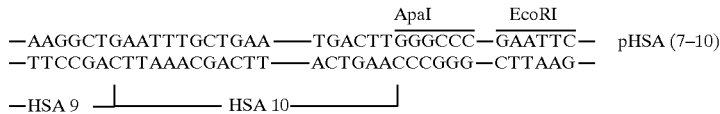

Cloning HSA 11 into pHSA (7-10)

0.1 μg of ApaI-EcoRI cleaved pHSA (7-10) and 5 pmol of HSA 11+A$_1$ were reacted in the usual way (Scheme 21).

160 colonies were replica plated and 9 of them proved to be positive after hybridization with 5'-$^{32}$P-HSA 11 oligonucleotide probe. Plasmids prepared from the positive clones were sequenced by using pKO primer I. One clone was found to contain the expected sequence and plasmid DNA prepared from this clone was used in the next step as pHSA (7-11).

240 clones were tested and 11 of them proved to be positive after hybridization with 5'-$^{32}$P-HSA 12 oligonucleotide probe. 2 of 10 sequenced (pKO primer I) plasmid DNA seemed to be correct and one of them was used later as pHSA (7-12) or pHSA III, i.e. the large HSA III fragment containing plasmid.

The sequence of the HSA (7-12), or HSA III fragment was confirmed by sequencing in M13mp19 and mp18 vectors. pHSA III was cleaved with PstI and EcoRI, the small

Scheme 21

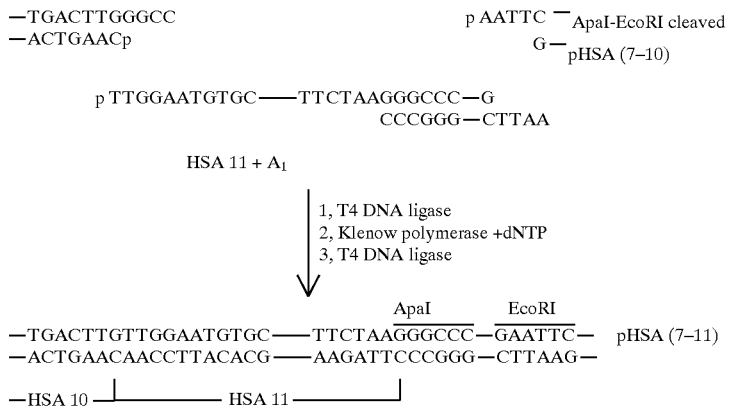

Cloning HSA 12 into pHSA (7-11)

0.1 μg of ApaI-EcoRI cleaved PHSA (7-11) were reacted with 5 pmol of HSA 12+A$_1$ according to the general procedure (Scheme 22).

fragment was isolated and cloned into PstI-EcoRI cleaved M13mp18 and mp19 vectors. Single-stranded phage DNA was prepared from the recombinants and they were sequenced using the 17-mer primer.

Scheme 22

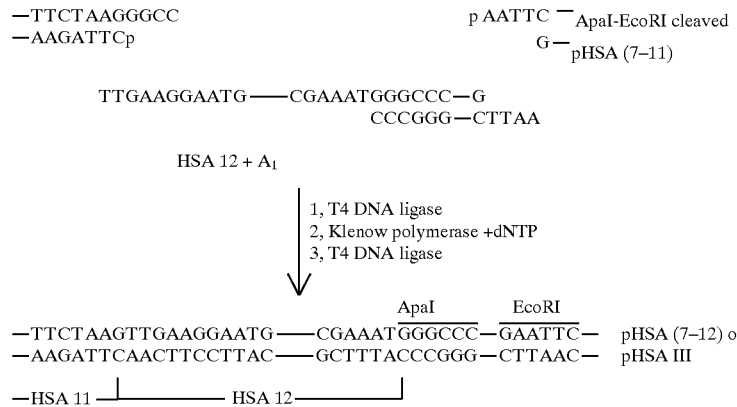

Cloning HSA 13 into pUC19

0.1 μg of BamHI-EcoRI cleaved pUC19 and 5 pmol of HSA 13+A₁ were reacted according to the general procedure (Scheme 23).

80 clones were tested by hybridization with 5'-³²P-HSA 13 probe and 14 of them were found to be positive. Plasmid DNA was prepared from 10 positive clones and sequenced using pKO primer I. 6 of them were identical with the expected pHSA 13 plasmid.

HSA 13 oligonucleotide, like HSA 7, contains the extra GGTAC 5'-terminal sequence, as this oligonuleotide is the first one in the HSA IV large fragment. In this case a KpnI site was also formed, which can be used later to join HSA III and HSA IV large fragments so that this extra sequence is eliminated at the joining point.

pHSA 13 was used to clone HSA 14 in the next step.

Cloning HSA 15 into pHSA (13-14)

When HSA 15+A₁ was tried to be cloned into ApaI-EcoRI cleaved pHSA (13-14) according to the general procedure, a large number of colonies hybridizing with 5'-³²P-HSA 15 were obtained, but after sequencing their plasmids, the expected HSA 15 sequence was never found. Instead, a double-mutated HSA 15 was obtained, in which G->T mutation took place at nucleotide positions 1072 and 1096 (nucleotide positions in mature HSA gene sequence). These G residues were surrouded by T residues. The possibility that these apparent mutations were merely due to ambiguous gel reading which occurs sometimes using plasmid DNA template, was excluded after recloning the region of interest into M13mp19 phage vector. Since these two mutations took place at the same time in all cases (19 different positive clones were tested), we had to change the general cloning

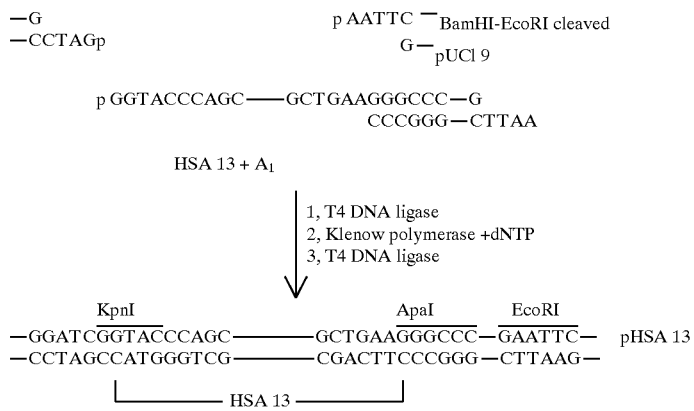

Cloning HSA 14 into pHSA 13

0.1 μg of ApaI-EcoRI cleaved pHSA 13 was reacted with 5 pmol of HSA 14+A₁ according to the general procedure (Scheme 24).

2 of 160 clones tested for by hybridization with 5'-³²P-HSA 14 were positive. After plasmid preparation and sequencing by pKO primer I, one of the two plasmid DNAs contained the expected sequence. It was called pHSA (13-14) and used in the next step.

strategy in this case so that a complementary oligonucleotide covering the sites of mutations in HSA 15 was employed.

A 42-mer complementary oligonucleotide was prepared and it was included into the ligation mixture of 5'-phosphate HSA 15 and adapter 1. 50 pmol of 5'-³²P-HSA 15 was mixed with 100 pmol of 5'-phosphate 42-mer, 100 pmol of 5'-phosphate adapter 1 upper strand and 100 pmol of 5'-hydroxyl adapter 1 lower strand oligonucleotide. The partial duplex was isolated after gel electrophoresis as

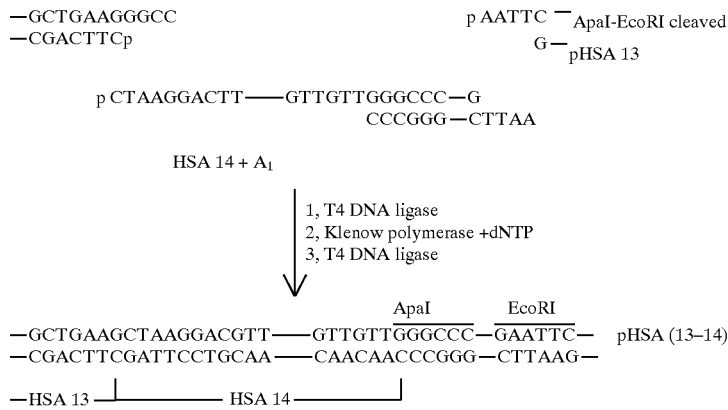

described previously in ~30% yield based on HSA 15. This partial duplex is named as HSA 15+C+A$_1$ in Scheme 25.

Next, 0.1 μg of ApaI-EcoRI cleaved pHSA (13-14) was reacted with 5 pmol of HSA 15+C+A$_1$ and the reactions were performed according to the general procedure. 340 clones were tested by 5'-$^{32}$P-HSA 15 probe and of the 17 positive clones 12 were used to prepare plasmid DNA. They were sequenced (pKO primer I) and 2 of them contained the expected HSA 15 sequence. This sequence was confirmed by recloning the HSA (13-15) region obtained so into M13mp19 phage vector and by performing the sequencing reactions on single-stranded DNA template.

One of the proper plasmids was used as pHSA (13-15) in the next step.

Reexamination of the HSA 16 sequence revealed that its 5'-terminal region and the 5'-terminal region of adapter 1 lower strand were nearly perfectly complementary. We planned to use a different ApaI-EcoRI adapter lacking this complementary region, (adapter 2, see Scheme 3). HSA oligonucleotides were ligated with adapter 2 exactly in the same way as with adapter 1.

0.1 μg of ApaI-EcoRI cleaved pHSA (13-15) was reacted with 5 pmol of HSA 16+A$_2$ according to the general procedure. Of 60 clones 24 were found to be positive after hybridization with 5'-$^{32}$P-HSA 16 probe. 10 positive clones were used to prepare plasmid DNA, they were sequenced with pKO primer I and two of them proved to be the expected pHSA (13-16).

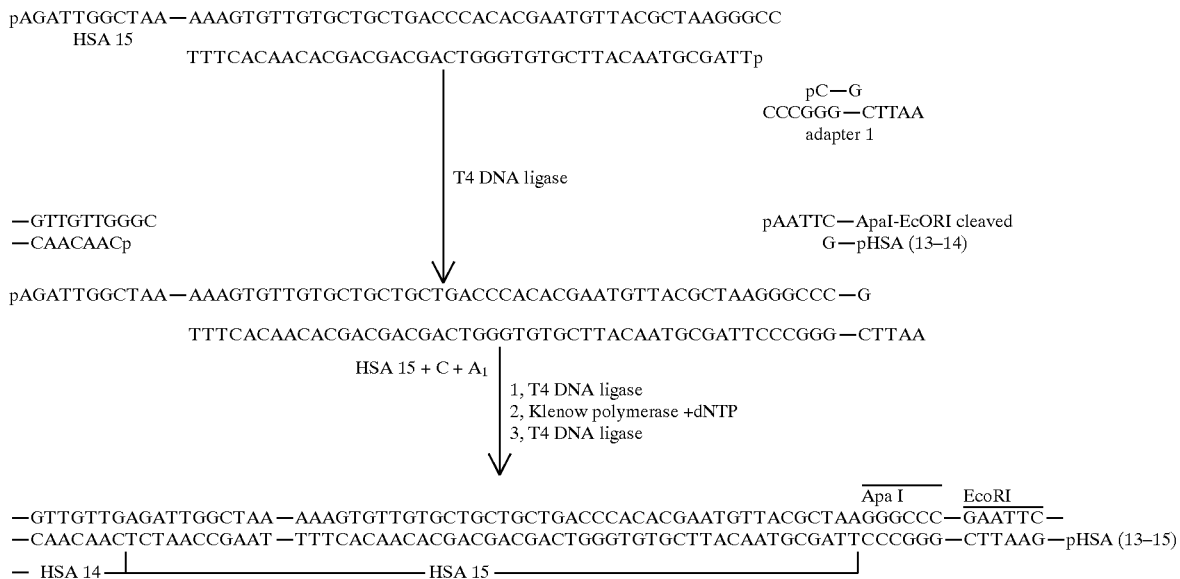

Cloning HSA 16 into pHSA (13-15)

When HSA 16+A$_1$ was cloned into ApaI-EcoRI cleaved PHSA (13-15), all the 16 sequenced positive clones had a 9 base pair deletion at the 5'-terminus of the HSA 16 region.

pHSA (13-16) was used later to prepare HSA (13-16) DNA region which was cloned into pHSA (17-18) to obtain pHSA (13-18), i.e. pHSA IV.

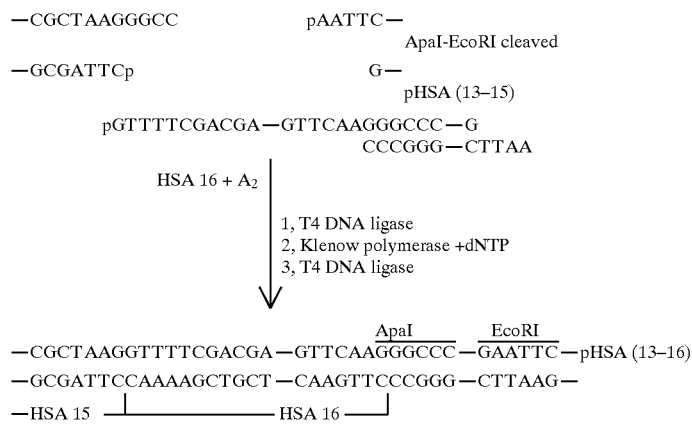

Cloning HSA 17 into pUC19

0.1 μg BamHI-EcoRI cleaved pUC19 was reacted with 5 pmol of HSA 17+A$_2$ in the usual way (Scheme 27).

160 clones were tested by hybridization with 5'-$^{32}$P-HSA 17. 30 of them were positive, and plasmids were prepared from 8 of them. 2 clones contained the expected pHSA 17 plasmid according to sequence data (pKO primer I).

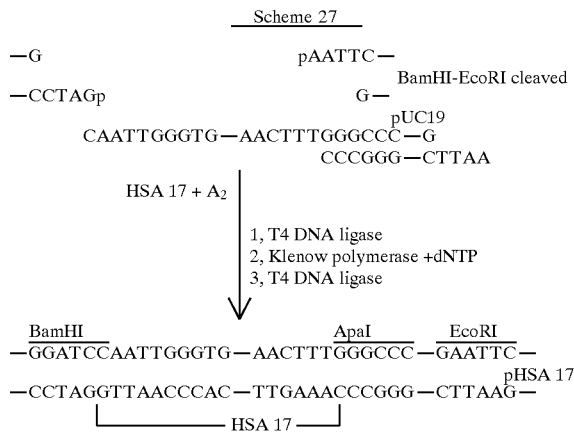

Cloning HSA 18 into pHSA 17

0.1 μg of ApaI-EcoRI cleaved pHSA 17 was reacted with 5 pmol of HSA 18+A$_2$ (Scheme 28).

Of the 160 clones tested by hybridization with 5'-$^{32}$P-HSA 18 probe, 24 were found to be positive. Plasmid DNA from 4 of the positive clones was prepared and sequenced using pKO primer I. 2 clones contained the correct PHSA (17-18) plasmid.

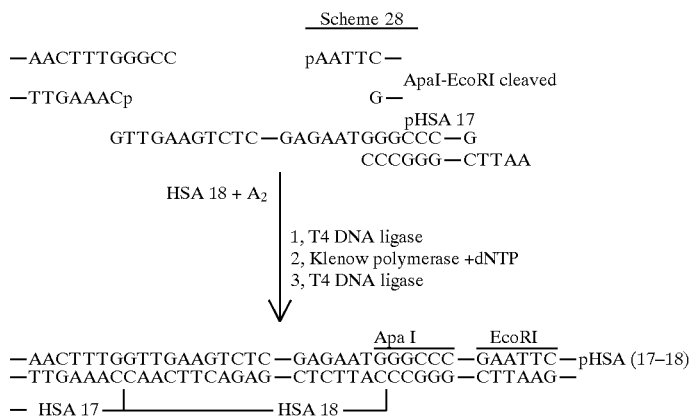

Cloning HSA 19 into pUC19

0.1 μg XbaI-EcoRI cleaved pUC19 was reacted with 5 pmol of HSA 19+A$_1$ according to the general procedure. (Scheme 29).

Transformed JM101 *E. coli* cells were plated onto LD-ampicillin plate in the presence of X-gal and IPTG as described for PHSA 7. Plasmid DNA from 6 randomly picked white colonies was prepared and sequenced using pKO primer I. 2 of them proved to be the correct pHSA 19.

HSA 19, like HSA 7 and HSA 13, contains the extra GGTAC sequence at its 5'-terminus. This sequence, as described before, will facilitate joining HSA V large fragment with HSA IV (see also later).

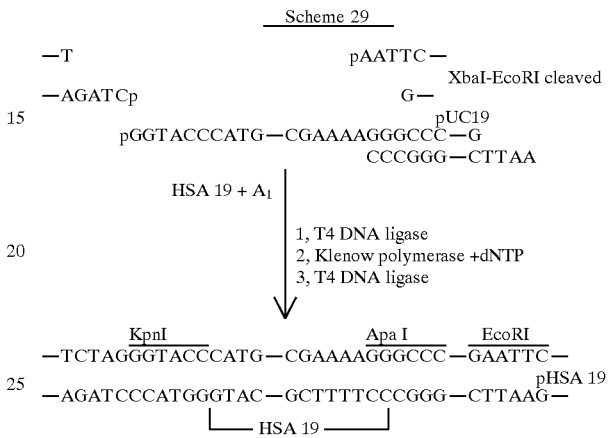

Cloning HSA 20 into pHSA 19

0.1 μg of ApaI-EcoRI cleaved pHSA19 was reacted with 5 pmol of HSA 20+A$_1$ as described in the general procedure (Scheme 30).

160 colonies were tested with 5'-$^{32}$P-HSA 20 oligonucleotide probe and 58 of them were positive. Plasmid DNA prepared from 11 positive clones were sequenced using pKO primer I, and 8 of them contained the correct pHSA (19-20) plasmid.

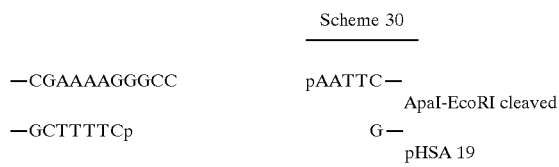

-continued

Scheme 30

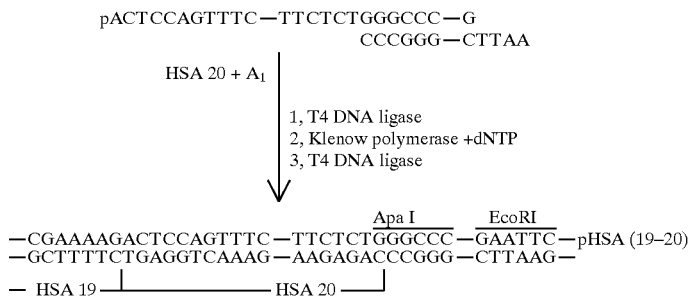

Cloning HSA 21 into pHSA (19-20)

0.1 μg of ApaI-EcoRI cleaved pHSA (19-20) and 5 pmol of HSA 21+A$_1$ were reacted in the usual way (Scheme 31).

33 of 240 clones were found to be positive after hybridization with 5'-$^{32}$P-HSA21 probe. 6 positive clones were used to prepare plasmid DNA and after sequencing with pKO primer I, 3 clones were shown to contain the expected pHSA (19-21) plasmid.

Cloning HSA 22 into pHSA (19-21)

0.1 μg of ApaI-EcoRI cleaved PHSA (19-21) and 5 pmol of HSA 22+A$_1$ were reacted in the usual way (Scheme 32).

80 clones were tested for hybridization with 5'-$^{32}$P-HSA 22 probe, and 10 were found positive. Plasmid DNA prepared from them were sequenced using pKO primer I and only one proved to be correct. This is called pHSA (19-22).

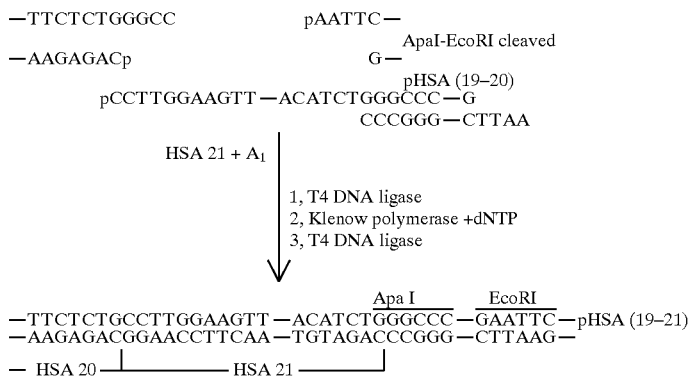

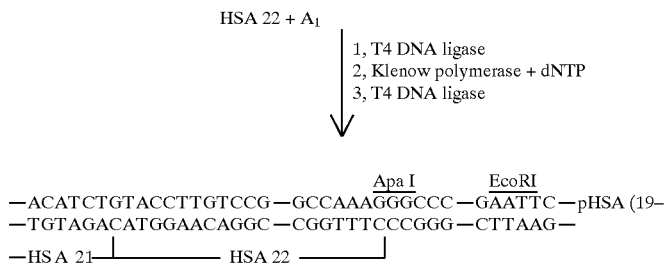

Cloning HSA 23 into pHSA (19-22)

0.1 μg of ApaI-EcoRI cleaved pHSA (19-22) and 5 pmol of HSA 23+$A_1$ were reacted according to the general procedure (Scheme 33).

160 clones were tested and 100 of them showed hybridization with 5'-$^{32}$P-HSA 23 probe. Plasmid DNA was prepared from 6 positive clones and they were sequenced with pKO primer I. 3 of them contained the correct HSA 23 sequence in the proper surroundings. One of them was used in the next step as pHSA (19-23).

Joining HSA Large Fragments

Although the HSA gene was planned to be assembled from 5 large fragments (HSA I, II, III, IV and V), up to now only HSA III and HSA V syntheses were demonstrated. HSA I is a flexible 5'-terminal region of HSA and it was chemically synthesized as a relatively short PstI-Sau3AI segment (see Scheme 4). HSA II and HSA IV were obtained from two DNA segments, i.e. HSA II or HSA (1-6) was obtained from HSA (1-3) and HSA (4-6), while HSA IV, or HSA (13-18) was obtained from HSA (13-16) and HSA (17-18). During

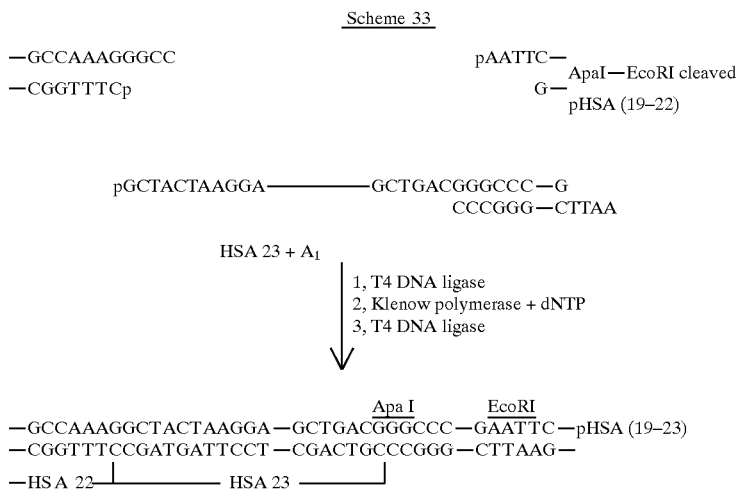

Cloning HSA 24 into pHSA (19-23)

0.1 μg of ApaI-EcoRI cleaved pHSA (19-23) was reacted with 5 pmol of HSA 24+$A_1$ in the usual way (Scheme 34).

Of 160 clones, 37 showed hybridization with 5'-$^{32}$P-HSA 24 probe. Plasmid DNA was prepared from 3 positive clones and they were sequenced with pKO primer I. 2 of the above plasmids contained the correct HSA 24 sequence, and one of them was used as pHSA (19-24) or pHSA V later.

The sequence of HSA V was confirmed after its recloning as a PstI-EcoRI fragment obtained from pHSA V into PstI-EcoRI cleaved M13mp18 and mp19 vector pair.

the assembly of HSA II and HSA IV large fragments, reaction series like restriction digestion followed either by mung bean nuclease treatment or Klenow polymerase +dNTP treatment were employed. These reaction conditions are fully described for obtaining pHSA II and pHSA IV, and similar reactions, when manipulating with HSA large fragments, will only be referred.

Mung bean nuclease and Klenow polymerase +dNTP treatment are used to remove the 5'- or 3'-overhanging single stranded DNA regions obtained after restriction enzyme cleavage to produce blunt ends. Mung bean nuclease removes 5'-protruding ends, while Klenow polymerase +dNTP treatment removes the 3'-protruding ends. The latter

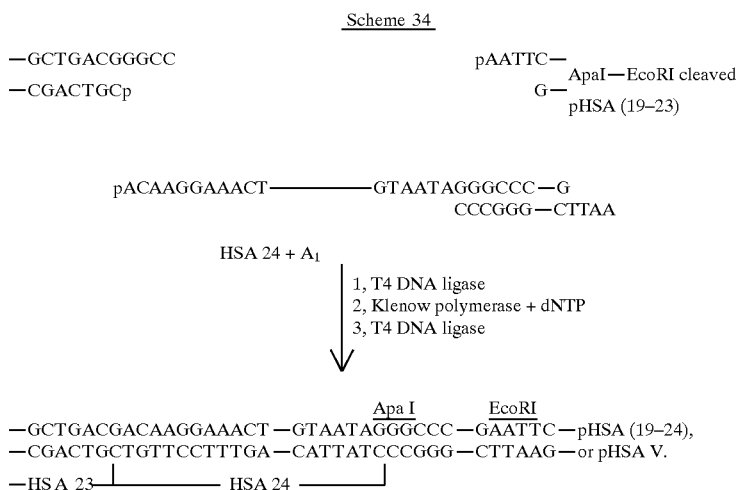

treatment, at the same time, fills in the 5'-protruding end to yield blunt end.

pHSA II

HSA II large fragment, cloned in pUC19 as pHSA II, was obtained from HSA (1-3) and HSA (4-6) DNA segments so that pHSA (1-3) was used as a vector to clone HSA (4-6).

b 1μg of pHSA (4-6) was treated with 10 units of XbaI in 50 μl of reaction volume containing 100 mM NaCl, 50 mM Tris-HCl, pH 7.5, 10 mM MgCl$_2$, 1 mM DTT (high salt buffer) at 37° C. for 1 hr. Linear vector DNA obtained so was ethanol precipitated, dried and dissolved in 50 μl of mung bean nuclease buffer (30 mM sodium acetate, pH 5.0, 100 mM NaCl, 2 mM ZnCl$_2$, 10% glycerol, 0.5 mg/ml denatured calf thymus DNA) and treated with 1 μl of 10 U/μl mung bean nuclease at 37° C. for 30 min. The reaction mixture was phenol extracted, then the DNA was ethanol precipitated. The pellet was dissolved in 50 μl of high salt buffer (see before for XbaI treatment) and 20 units of EcoRI was added to the reaction mixture which was kept at 37° C. for 1 hr. After ethanol precipitation, the small HSA (4-6) fragment was isolated by electrophoresis on a 2% agarose gel (in TAE buffer) followed by electroelution and ethanol precipitation. This fragment has a blunt end at the 5'-terminus and an EcoRI sticky end at the 3'-terminus (Scheme 35).

1 μg of pHSA (1-3) was dissolved in 50 μl of low salt buffer containing 6 mM NaCl, 6 mM Tris-HCl, pH 7.4, 6 mM MgCl$_2$ and 1 mM DTT and treated with 10 units of ApaI at 37° C. for 1 hr. After ethanol precipitation, the pellet was dissolved in 50 μl of Klenow buffer containing 7 mM Tris-HCl, pH 7.5, 7 mM MgCl$_2$, 5 mM β-mercaptoethanol, 0.1 mM EDTA and 0.1 mM dNTP and treated with 0.5 μl of 5 U/μl Klenow polymerase at room temperature for 10 min. After phenol extraction and ethanol precipitation, the pellet was dissolved in 50 μl of high salt buffer and 10 units of EcoRI was added. The reaction mixture was kept at 37° C. for 2 hrs, then the DNA was ethanol precipitated. Large vector fragment having a blunt-end and an EcoRI end was isolated by electrophoresis on 0.5% agarose gel in TAE buffer followed by electroelution and ethanol precipitation. (Scheme 35).

The cleaved pHSA (1-3) vector (0.1 μg) was ligated with HSA (4-6) fragment (approx. 0.03 μg) in 10 μl of reaction volume containing 50 mM Tris-HCl, pH 7.5, 10 mM MgCl$_2$, 10 MM DTT, 1 mM ATP (ligase buffer) and 80 units of T4 DNA ligase was added at 15° C. for 12 hrs. The reaction mixture was transformed into frozen competent JM101 cells and they were then plated onto LB-ampicillin plates. Of 110 replica-plated colonies, 55 showed hybridization with 5'-$^{32}$P-HSA 4 oligonucleotide probe. Plasmid DNA was prepared from 10 positive clones and they were sequenced by using the reverse primer. 2 of them showed the expected sequence at the junction of HSA 3 and HSA 4 oligonucleotides, and they were used later as pHSA (1-6) or pHSA II (Scheme 35).

(The sequence of HSA II was confirmed after its subcloning into PstI-EcoRI cleaved M13mp18 and mp19 phage vector, and the sequencing reactions were performed on single-stranded DNA template).

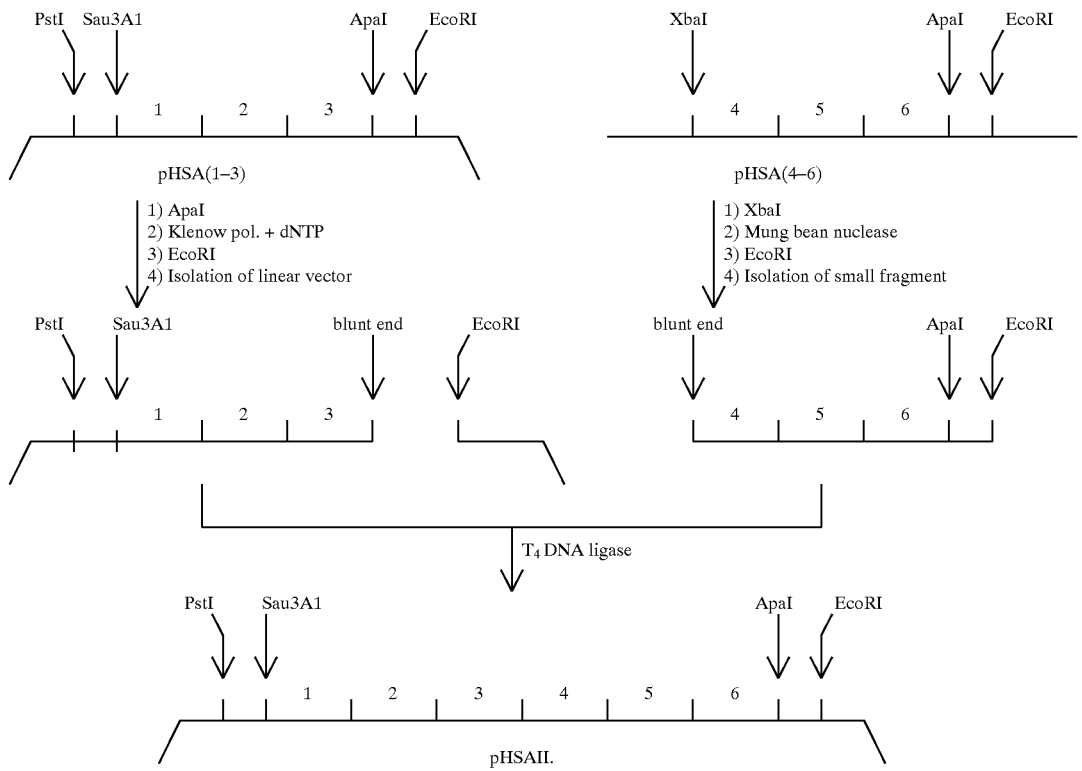

Scheme 35 pHSA IV

HSA IV large fragment was obtained from the previously cloned HSA (13-16) and HSA (17-18) DNA segments so that pHSA (17-18) vector was used to clone HSA (13-16) (Scheme 36).

1 μg of pHSA (13-16) was treated with 20 units of ApaI in 50 μl of low salt buffer for 1 hr at 37° C. The DNA was ethanol precipitated and dissolved in 50 μl of Klenow buffer containing 0.1 mM dNTP and treated with 2.5 units of cloning into phage vector M13mp18 and mp19. Sequencing was performed on single-stranded DNA template).

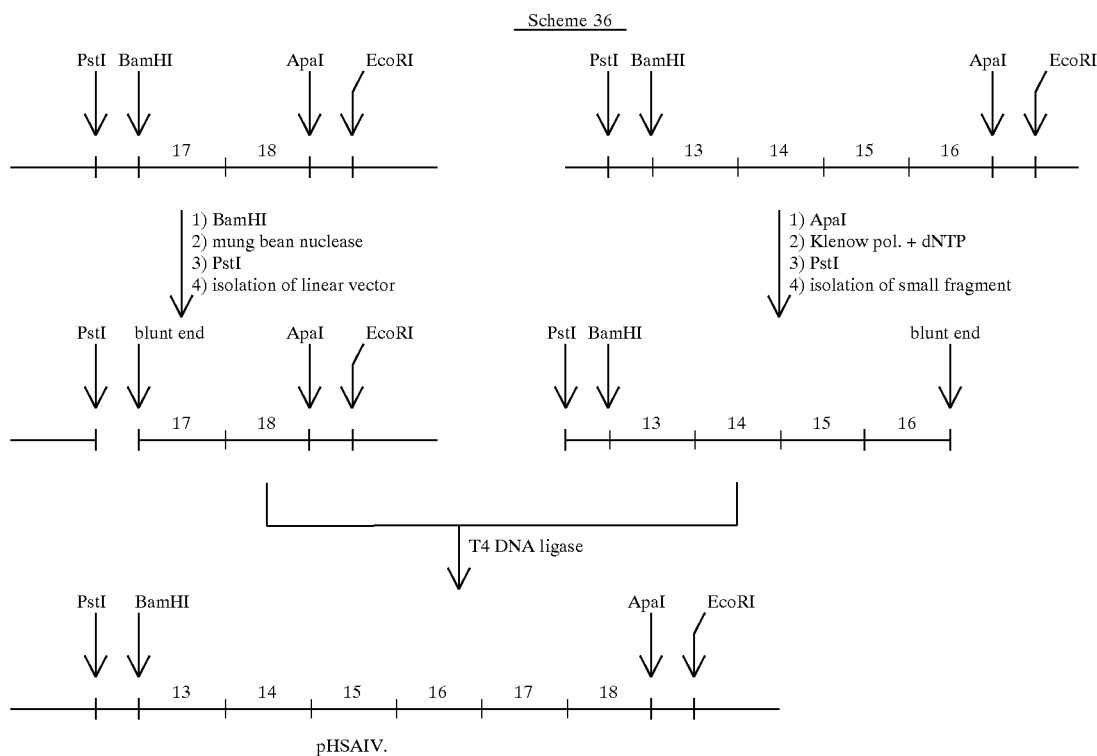

Scheme 36 pHSAIV.

Klenow polymerase at room temperature for 10 min. The reaction mixture was phenol extracted and ethanol precipitated, and the pellet was dissolved in 50 μl of high salt buffer containing 20 units of PstI at 37° C. for 1 hr. After ethanol precipitation the small fragment was isolated by electrophoresis on a 2% agarose gel followed by electroelution. This procedure yielded HSA (13-16) DNA segment having a blunt end and a PstI sticky end. (Scheme 36).

1 μg of pHSA (17-18) was cleaved with 10 units of BamHI in 50 μl reaction volume containing high salt buffer at 37° C. for 1 hr. DNA was ethanol precipitated and dissolved in 50 μl of mung bean nuclease buffer then 10 units of mung bean nuclease was added at 37° C. for 30 min. After phenol extraction and ethanol precipitation the pellet was dissolved in 50 μl of high salt buffer and 20 units of PstI was added for 1 hr at 37° C. The large linear vector fragment was ethanol precipitated, purified by electrophoresis on a 0.5% agarose gel (TAE buffer) followed by electroelution. This reaction series resulted in cleaved pHSA (17-18) vector having a blunt-end and a PstI sticky end. (Scheme 36).

The cleaved pHSA (17-18) vector (0.1 μg) was ligated with HSA (13-16) (approx. 0.05 μg) in 10 μl of ligase buffer containing 80 units of T4 DNA ligase at 15° C. for 12 hrs. The mixture was then transformed into frozen competent JM101 cells and plated onto LB-ampicillin plates. 230 colonies were tested by hybridization with 5'-$^{32}$P-HSA 16 probe and 86 were found to be positive. Plasmid DNA was prepared from 10 clones and they were sequenced by using pKO primer I. 5 plasmid DNA showed the correct junction between HSA 16 and HSA 17 oligonucleotide regions, and they were used later as pHSA (13-18), or pHSA IV (Scheme 36).

(The sequence of HSA IV was confirmed after its subpHSA (II-III)

In this case pHSA III was used as a vector to clone HSA III fragment (Scheme 37).

HSA III fragment preparation

5 μg of pHSA III was treated with 40 units of KpnI in 100 μl of low salt buffer at 37° C. for 3 hrs. The cleaved vector was ethanol precipitated and the pellet was dissolved in 50 μl of Klenow buffer containing 0.1 mM dNTP and 2.5 units of Klenow polymerase and the mixture was kept at room temperature for 10 min. After phenol extraction and ethanol precipitation, the pellet was dissolved in 50 μl of high salt buffer, 40 units of EcoRI was added and the mixture was kept at 37° C. for 2 hrs. The DNA was ethanol precipitated and the HSA III fragment was isolated by electrophoresis on a 2% agarose gel in TAE buffer followed by electroelution. The HSA III containing large fragment obtained so has a blunt-end and an EcoRI sticky end (Scheme 37).

pHSA II vector cleavage

1 μg of pHSA II was dissolved in 50 μl of low salt buffer and treated with 10 units of ApaI at 37° C. for 2 hrs. After ethanol precipitation, the pellet was dissolved in 50 μl of Klenow buffer containing 0.1 mM dNTP and treated with 2.5 units of Klenow polymerase at room temperature for 10 min. The mixture was phenol extracted, the DNA was ethanol precipitated and the pellet was dissolved in 50 μl of high salt buffer, then 20 units of EcoRI was added. The reaction mixture was kept at 37° C. for 2 hrs and the DNA was ethanol precipitated. Large vector fragment was isolated by electrophoresis on a 0.5% agarose gel in TAE buffer followed by electroelution. The linear vector obtained so has a blunt-end and an EcoRI sticky end (Scheme 37).

Ligation 0.2 μg of cleaved pHSA II vector was mixed with 0.1 μg of HSA III fragment in 10 μl of ligase buffer and 80 units of T4 DNA ligase was added. The reaction mixture was kept at 15° C. for 14 hrs and then it was transformed into JM101 *E. coli* cells. Approx. 50% of the ampicillin resistant colonies showed hybridization with 5'-$^{32}$P-HSA 11 oligonucleotide probe. Plasmid DNAs prepared from 8 positive clones were sequenced using a synthetic primer complementary with a part of HSA oligonucleotide (between nucleotide positions 508–527 of the mature HSA gene), and all 8 showed the proper sequence at the junction point of HSA II and HSA III large fragments.

pHSA V vector cleavage

2 μg of pHSA V was treated with 10 units of KpnI in 50 μl of low salt buffer at 37° C. for 4 hrs. After ethanol precipitation, the pellet was dissolved in 50 μl of Klenow buffer containing 0.1 mM dNTP and 2.5 units of Klenow polymerase and was kept at room temperature for 10 min. After phenol extraction and ethanol precipitation, the pellet was dissolved in 50 μl of high salt buffer and 40 units of PstI was added. The mixture was kept at 37° C. for 4 hrs. After

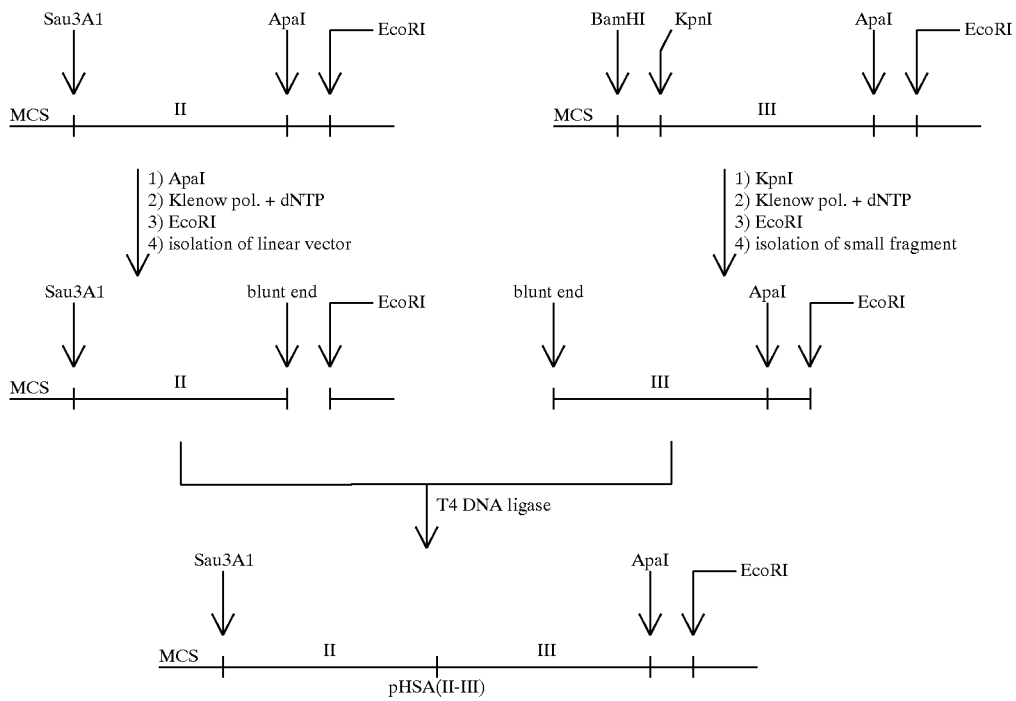

MCS: multiple cloning site derived from pUCl9, containing those sites which are upstream PstI site, including PstI site.

pHSA (IV-V)

In this case pHSA V served as a vector to clone HSA IV fragment (Scheme 38).

HSA IV fragment preparation

2 μg of pHSA IV was treated with 10 units of ApaI in 50 μl of low salt buffer at 37° C. for 2 hrs. The linear vector was ethanol precipitated and the pellet was dissolved in 50 μl of Klenow buffer containing 0.1 mM dNTP and 2.5 units of Klenow polymerase was added at room temperature for 10 min. After phenol extraction and ethanol precipitation, the pellet was dissolved in 50 μl of high salt buffer, 40 units of PstI was added and the mixture was kept at 37° C. for 2 hrs. After-ethanol precipitation, the small fragment containing HSA IV sequence was purified by electrophoresis on a 2% agarose gel in TAE buffer followed by electroelution. The small fragment has a PstI sticky end and a blunt-end. (Scheme 38).

ethanol precipitation, the linear vector was purified by electrophoresis on a 0.5% agarose gel in TAE buffer followed by electroelution. The cleaved pHSA V vector obtained so has a PstI sticky end and a blunt end (Scheme 38).

Ligation

Approx. 0.1 μg linearized pHSA V vector and 0.05 μg of HSA IV containing fragment was treated with 80 units of T4 DNA ligase in 10 μl of ligase buffer at 15° C. for 4 hrs. After transformation into JM101 *E. coli* cells, the ampicillin resistant colonies were tested with 5'-$^{32}$P-HSA 16 oligonucleotide probe and approx. 40% of them were positive. 8 colonies were used to prepare plasmid DNA, they were sequenced with a synthetic primer complementary with a part of HSA 19 oligonucleotide (nucleotide positions 1374–1393 in the mature HSA gene) and 7 of them had the correct sequence at the junction point between HSA IV and HSA V regions.

Scheme 38

Joining HSA IV and HSA V

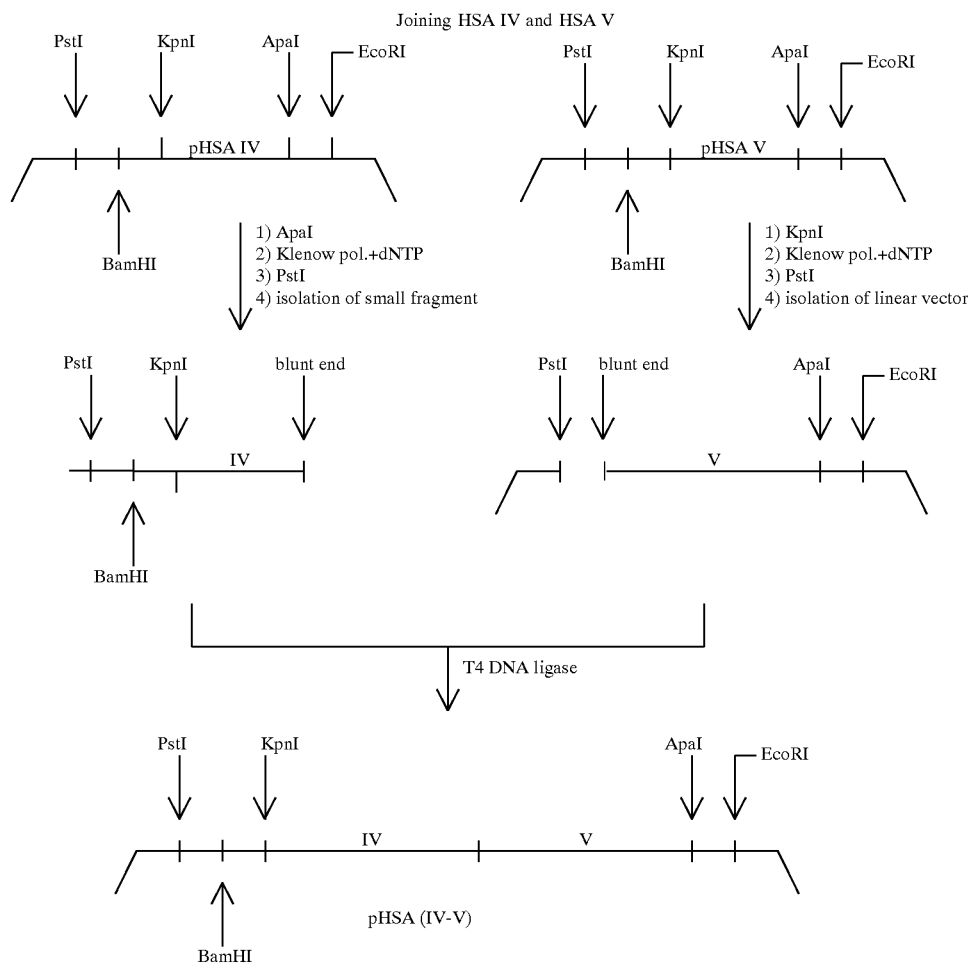

pHSA (IV-V) with ApaI-SacI-EcoRI Adapter [pHSA (IV-V) ASE]

pHSA (IV-V) obtained as before contains adapter 1 downstream of the HSA coding region. Cloning of the HSA gene into the *E. coli* part (pPT2HK$_1$) of the *E.coli*-yeast shuttle vector requires a downstream SacI site and so this site has to be introduced somehow. It seems to be advantageous to introduce it at this stage of the gene assembly. The most obvious way to have a SacI site seems to be the replacement of the ApaI-EcoRI adapter 1 with a similar adapter having an internal SacI site (adapter 3, see Scheme 3).

HSA (IV-V) region was isolated from pHSA (IV-V) as a PstI-ApaI fragment and it was cloned, together with adapter 3 (ApaI-SacI-EcoRI adapter) into PstI-EcoRI cleaved pUC19.

HSA (IV-V) fragment isolation:

2 μg of PHSA (IV-V) was treated with 20 units of ApaI in 50 μl of low salt buffer at 37° C. for 3 hrs. After ethanol precipitation, the pellet was dissolved in 50 μl of high salt buffer and 20 units of PstI was added. The reaction mixture was kept at 37° C. for 4 hrs. The HSA (IV-V) fragment was purified by gel electrophoresis on a 2% agarose gel in TAE buffer followed by electroelution.

Ligation: (Scheme 39)

0.1 μg of PstI-EcoRI cleaved pUC19 was mixed with 0.05 μg of ApaI-EcoRI HSA (IV-V) fragment and with 5—5 pmol of 5'-phosphorylated adapter 3 oligonucleotides in 20 μl of ligase buffer. 80 units of T4 DNA ligase was added and the mixture was kept at 15° C. for 14 hrs. After transformation, ampicillin resistant colonies were screened on two different replica plates with either 5'-$^{32}$P-HSA 16 oligonucleotide probe or 5'-$^{32}$P-adapter 3 lower strand oligonucleotide probe. Approx. 50% of the colonies showed hybridization with both probes. Positive colonies were used to prepare plasmid DNA and sequencing was performed by both the reverse primer and the pKO primer I. All the 10 clones checked by sequencing proved to be correct.

In the following, this pHSA (IV-V), which is supplied with a downstream SacI site by introducing adapter 3, is used for the further steps of the HSA gene assembly.

Scheme 39

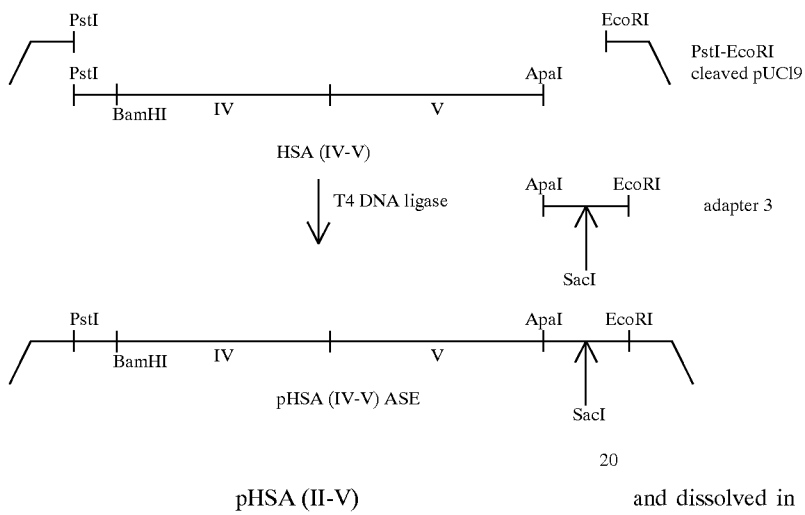

pHSA (II-V)

In this case, pHSA (II-III) served as a vector to clone HSA (IV-V) fragment (Scheme 40).

pHSA (II-III) vector cleavage:

2 μg of pHSA (II-III) was treated with 40 units of ApaI in 50 μl of low salt buffer at 37° C. for 5 hrs. After ethanol precipitation, the pellet was dissolved in 50 μl of Klenow buffer containing 0.1 mM dNTP and 2.5 units of Klenow polymerase was added. The mixture was kept at room temperature for 10 min, then it was phenol extracted and ethanol precipitated. The pellet was dissolved in 50 μl of high salt buffer and 20 units of EcoRI was added. The mixture was kept at 37° C. for 5 hrs then the linear vector was isolated by electrophoresis on a 0.5% agarose gel in TAE buffer followed by electroelution.

HSA (IV-V) fragment isolation:

2 μg of pHSA (IV-V) was dissolved in 50 μl of low salt buffer and treated with 20 units of KpnI at 37° C. for 5 hrs. After ethanol precipitation the pellet was dissolved in Klenow buffer containing 0.1 mM dNTP and 2.5 units of Klenow polymerase. The mixture was kept at room temperature for 10 min, then the DNA was ethanol precipitated and dissolved in 50 μl of high salt buffer and 20 units of EcoRI was added. The reaction mixture was kept at 37° C. for 5 hrs, then the small fragment containing HSA (IV-V) region was isolated by electrophoresis on a 2% agarose gel in TAE buffer followed by electroelution.

Litigation:

Approx. 0.1 μg of linearized pHSA (II-III) vector and 0.05 μg of HSA (IV-V) containing fragment were mixed in 10 μl of ligase buffer containing 80 units of T4 DNA ligase and the mixture was kept at 15° C. for 7 hrs. After transformation into JM101 E. coli cells, ampicillin resistant colonies were tested by hybridization with 5'-$^{32}$P-HSA 21 oligonucleotide probe and approx. 40% of the colonies proved to be positive. 8 colonies were used to prepare plasmid DNA, they were sequenced using 5'-$^{32}$P-HSA 11 oligonucleotide as a sequencing primer. All 8 had the proper joining point between HSA III and HSA IV regions.

The whole HSA (II-V) containing region of pHSA (II-V) was checked by sequencing on plasmid template (pKO primer I and HSA 1-8 primers were used) and no mistake was found.

Scheme 40

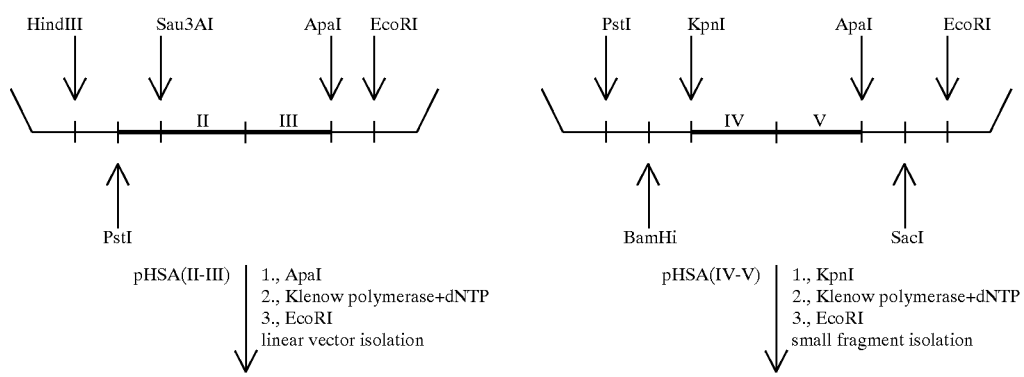

-continued
Scheme 40

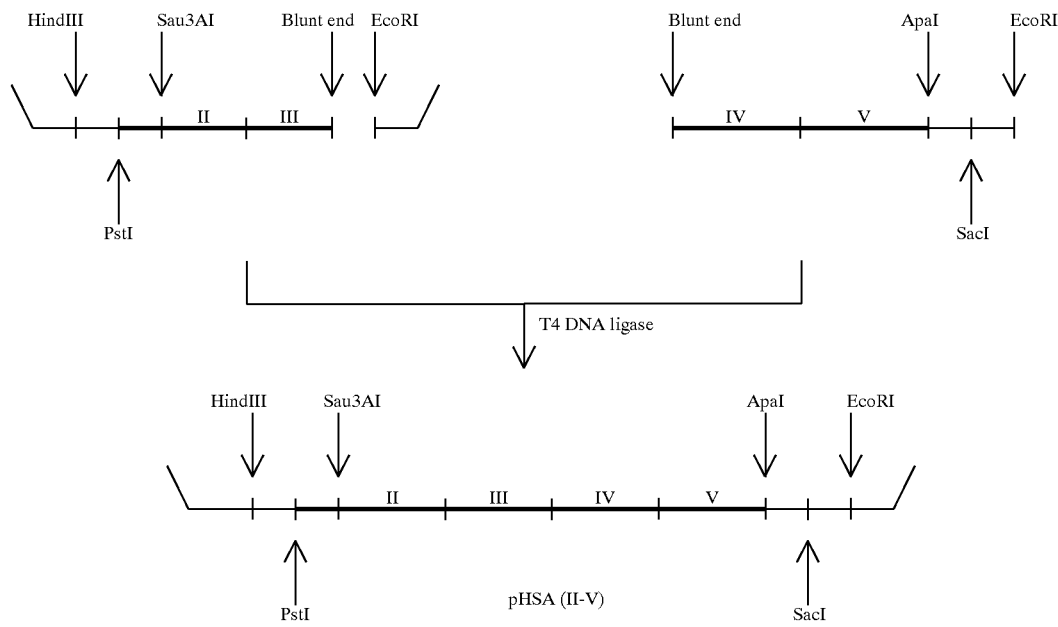

pHSA Vectors (No 1, No 2)

HSA (II-V) fragment was supplemented with HSA I fragment by cloning these two fragments into pUC19 vector. (Scheme 41).

HSA (II-V) could have been isolated as Sau3AI-EcoRI fragment directly as there is a unique Sau3AI site in the gene. The pUC19 vector part, however, contains many Sau3AI sites, complicating the restriction digestion and fragment separation. First, HSA (II-V) was isolated in a HindIII-EcoRI fragment, which was shortened further by Sau3AI treatment.

5 μg of HSA (II-V) was treated in 100 μl of high salt buffer with 40 units of HindIII and 40 units of EcoRI at 37° C. for 3 hrs. The mixture was applied onto a 0.5% agarose gel (TAE buffer) and after electrophoresis, two fragments were obtained. The smaller fragment was electroeluted and ethanol precipitated.

The pellet was dissolved in 50 μl of high salt buffer and treated with 7.5 units of Sau3AI at 37° C. for 14 hrs. The reaction mixture was phenol extracted (2x), ethanol precipitated, so the large Sau3AI-EcoRI fragment was not purified by gel electrophoresis in this case.

Two separate ligations were set up, each containing the PstI-EcoRI cleaved pUC19 cloning vector and the Sau3AI-EcoRI HSA (II-V) fragment, and one of the two HSA I fragments (as a mixture of two oligonucleotides forming a PstI-Sau3AI adapter).

0.2 μg of PstI-EcoRI cleaved pUC19 and 0.1 μg of Sau3AI-EcoRI HSA (II-V) fragment were mixed with 5–5 pmoles of 5'-phosphorylated HSA I No 1, or HSA I No 2, (Scheme 4) in two separate reaction mixtures containing 10 μl of ligase buffer. 80 units of T4 DNA ligase was added to both reaction mixtures, they were kept at 15° C. for 6 hrs, then transformed into JM101 E. coli cells. The transformed mixtures were plated onto LB-ampicillin plates. Colonies were double-replicated onto 2 nitrocellulose filters and they were hybridized with 5'-$^{32}$P-HSA 5 oligonucleotide probe (first filter) and with the corresponding 5'-$^{32}$P-HSA I oligonucleotide probe (second filter). Approx. 80% of the colonies showed hybridization with both probes in both cases. Plasmid DNA was prepared from 4—4 clones of the two constructions and they were sequenced using the reverse primer to check the proper insertion of HSA I versions into pHSA vectors. All sequenced constructions were correct.

The whole HSA coding regions from pHSA No 1 and No 2 were subcloned as PstI-EcoRI fragments into M13mp18 and mp19 phage vectors and the whole sequence was checked in mp19 using the 17-mer primer and HSA 1-9 primer. The mp18 constructions were checked only with the 17-mer primer.

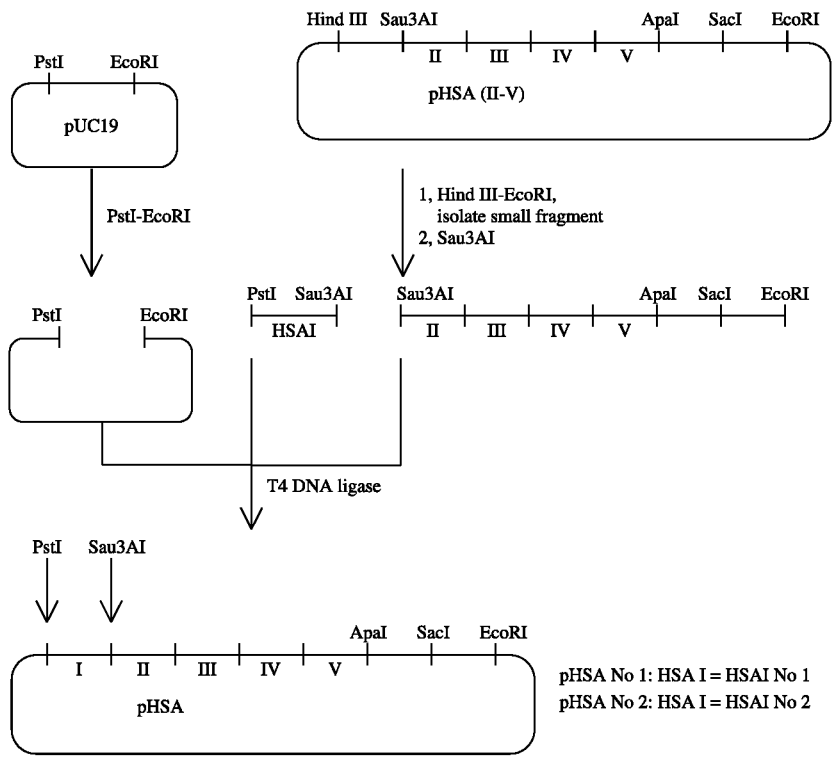

Scheme 41

The Construction of the E. Coli Plasmid Carrying the Yeast Promoter and Terminator Sequences 1. The starting cloning vector (pGB1, FIG. 1) was obtained by modification of pBR327 plasmid (Soberón, X., Covarrubias, L. and Bolivar, F. (1980): Gene 9, 287–305.) from which the PstI and HindII sites from the $Ap^R$ region were eliminated by EMS and HA mutagenesis and repeated restriction enzyme digestion. Conditions of the mutagenesis were the same as described in Miller, J. H.: Experiments in Molecular Genetics. Cold Spring Harbor Laboratory, Cold Spring Harbor, N.Y.

The XhoI site was introduced as a CCTCGAGG linker inserted at the unique (filled-in) AvaI site.

Figure 2:
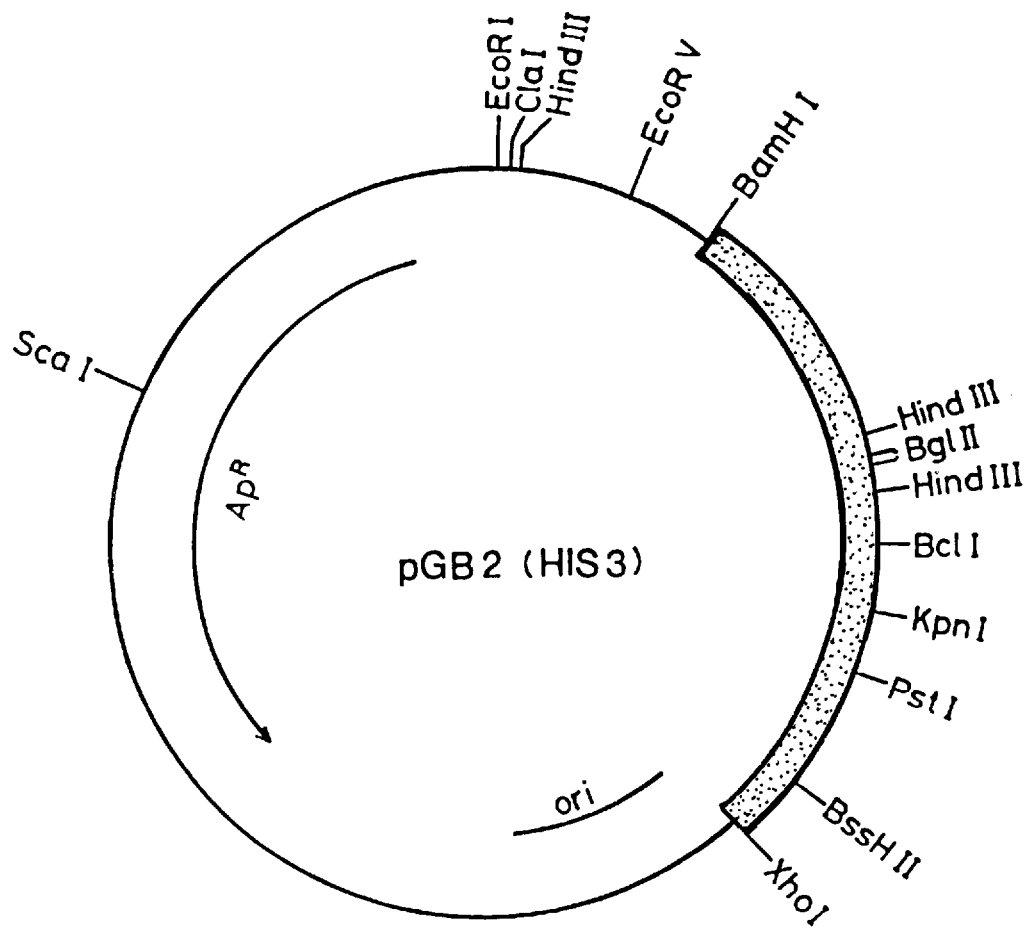
FIG. 2 shows the map of plasmid pGB2 containing a yeast HIS3 gene.

2. The plasmid pGB2 (HIS3):

The 1327 bp BamHI-XhoI fragment containing the entire cloned HIS3 gene of Saccharomyces cerevisiae (Storms, R. K., McNeil, J. B., Khandekar, P. S., An, G., Parker, J., and Friesen, J. D. (1979) J. Bacteriol. 140, 73–82; and Struhl, K. (1985): Nucleic Acids Res. 13, 8587–8601) was excised from pYF 92 (Storms, et al. ibid) (obtained from Gyorgy B. Kiss, Institute of Genetics, Biological Research Center of the Hungarian Academy of Sciences, Szeged, Hungary) and inserted at the unique BamHI and XhoI sites of pGB1, resulting in pGB2 (HIS3) (FIG. 2).

Figure 3A:
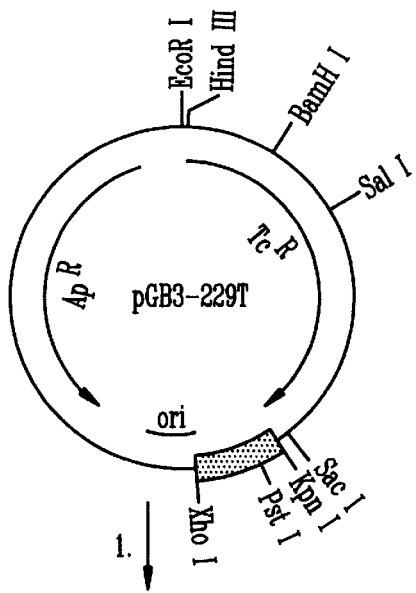
FIG. 3 shows the map of the plasmid pGB3-229T (a.) and the construction by steps 1 and 2 of the basic expression vector pPT2HK$_1$ (c.) through an intermediate construction pGB3-229TK° (b.).
Figure 3B:
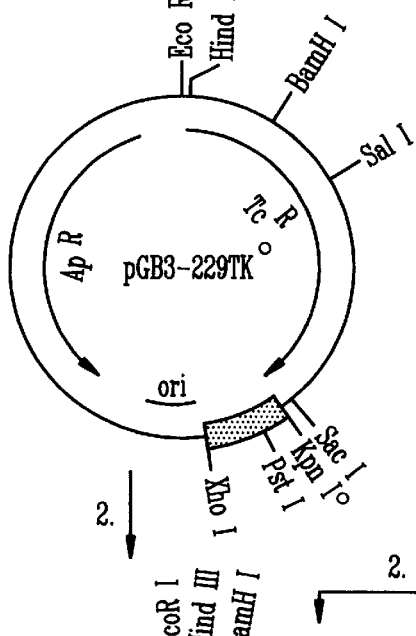
Figure 3C:
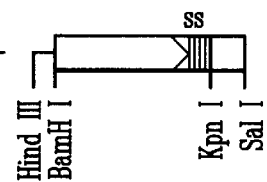
Figure 3C:
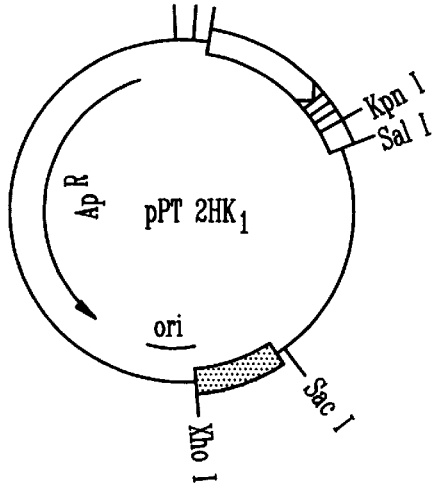

3. The plasmid pGB3-229T containing the transcriptional terminator region of the yeast His3 gene:

The EcoRI-KpnI fragment of pGB2 (HIS3) was replaced by the 1327 bp $Tc^R$ cartridge (EcoRI-KpnI) from the plasmid pJRD 158 (Davison, J., Heustersprute, M., Merchez, M., and Brunel, E (1984): Gene 28, 311–318) [obtained from John Davison (Unit of Molecular Biology, International Institute of Cellular and Molecular Pathology, 75, Avenue Hippocrate, B-1200, Brussels, Belgium)]. The pGB3-229T—besides the $Ap^R$+ori cartridge—carries the entire $Tc^R$ gene (with an additional SacI site at its 3'-end) and the transcriptional terminator region of the HIS3 gene. (FIG. 3a). The pGB-229T was further modified by 1) deletion of KpnI site in pGB-229T to obtain pGB3-229TK° (FIG. 3b) and 2) insertion of the HindIII-SalI promoter fragment from pUC18$^x$/622PH (of FIG. 5) resulting in pPT2HK$_1$ (FIG. 3c).

4. Cloning of the promoter region of the PHO5 gene of *Saccharomyces cerevisiae*.

The PHO5 gene encodes a repressible acid phosphatase exoenzyme (orthophosphoric—monoester phosphahydrolase (acid optimum), EC 3.1.3.2.). It is a part of a 8 kb. EcoRI genomic DNA fragment (Kramer, R. A., Andersen, N. (1980): Proc. Natl. Acad. Sci. USA 77, 6541–6545; and Rogers, D. T., Lemire, J. M., and Bostian, K. A. (1982): Proc. Natl. Acad. Sci. USA, 79, 2157–2161).

Figure 4:
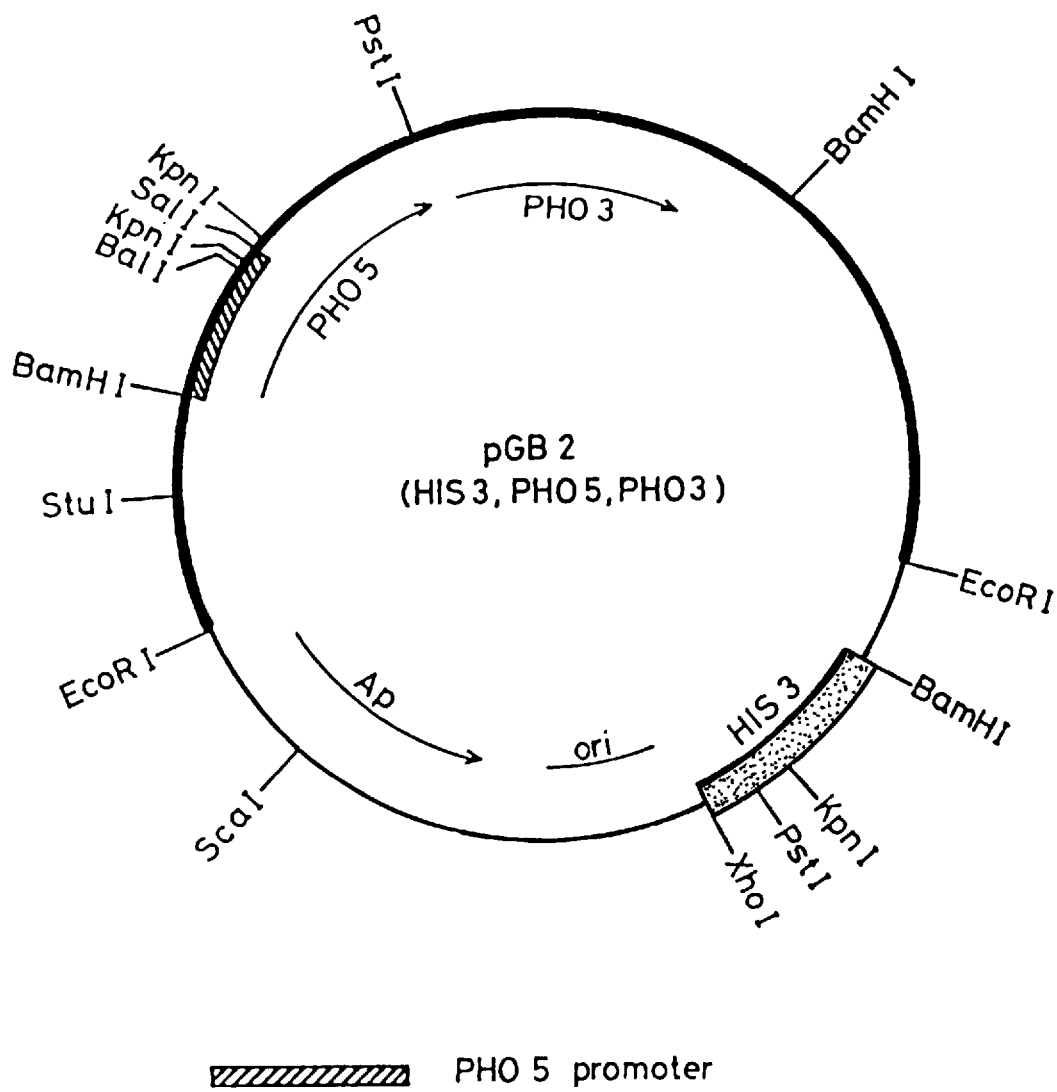
FIG. 4 shows the map of pGB2 (HIS3, PHO5, PHO3).

To obtain the plasmid carrying the PHO5 gene (Davison et. al. ibid) a yeast gene bank (a cosmid library constructed from the genomic DNA of *S. cerevisiae*, obtained from Z. Feher, Debrecen Medical University, Debrecen, Hungary) was screened as follows: a mixture of the recombinant cosmid DNA was digested with EcoRI. 8 kb EcoRI fragments were isolated from agarose gels, and recloned at the EcoRI site of the plasmid pGB2 (HIS3). The PHO5-gene containing plasmid (pGB2 (HIS3, PHO5, PHO3) (FIG. 4) was then selected on the basis of the complemetation of the pho5 mutation in the yeast strains DB-4 (Rogers et. al. ibid.) and AH220 (a, trp1, leu2-3, 2-112, his3-11, 3-15, pho5, pho3) provided by A. Hinnen, CIBA-GEIGY, Basel; see Tait-Kamradt, A. G., Turner, K. J., Kramer, R. A., Elliott, Q. D., Bostian, S. J., Thill, G. P., Rogers, D. T., and Bostian. K. (1986): Molec. and Cell. Biol. 6, 1855–1865).

5. Subcloning of the PHO5 gene promoter region.

The promoter of the repressible acidic phosphatase gene (PHO5) can be excised from the plasmid pGB2 (HIS3, PHO5, PHO3) by BamHI+SalI restriction enzyme digestion as a 623 bp fragment (Meyhack, B., Bajwa, W., Rudolph, H., and Hinnen, A. (1982): EMBO J. 1, 675–680). The latter was recloned in pUC18 at BamHI-SalI sites resulting in the plasmid pUC18/623P (FIG. 5a) in which the insert's sequence was verified by sequencing and compared to that from published literature (Meyhack, et. al. ibid; and Arima, K., Oshima, T., Kubota, I., Nakamura, N., Mizunaga, T., and Toh-e, A (1983): Nucleic Acids Res. 11, 1657–1672).

The BamHI-SalI (623 bp) fragment in pUC18/623P plasmid contains the PHO5 upstream activating sequences and part of the coding sequence (encoding the N-terminal 17-amino-acid secretion signal peptide and 10 more amino acids from the N-end of the mature gene product).

The primary structure of the secretion-signal coding region of the PHO5 gene:

```
                Met  Phe  Lys  Ser  Val  Val  Tyr  Ser  Ile  Leu
↑ PROMOTER – ATG TTT  AAA  TCT  GTT  GTT  TAT  TCA  ATT  TTA
                     DraI
↑
BamHI

Ala  Ala  Ser  Leu  Ala  Asn  Ala  Gly  Thr
        GCC  GCT  TCT  TTG  GCC  AAT  GCA  GGT  ACC
                         BalI            ↑ KpnI
                                         |
                                     Signal end
```

In this structure the KpnI site located downstream from the "signal end" codon Ala could be used as a cloning site (made blunt end by KpnI followed by trimming the 3'-protruding sequence) for the HSA coding gene if it were shifted by one base into the 5'-direction.

In pUC18/623P the above mentioned KpnI site could not be manipulated unless the upstream KpnI site (x, FIG. 5a) had been deleted from the plasmid. The plasmid therefore was cleaved with SacI and BamHI, followed by creating blunt ends by removing the protruding 3'-terminal nucleotides from the SacI end and filling-in the BamHI end with DNA polymerase I Klenow fragment and nucleoside triphosphates (step 1. in FIG. 5). Following religation and transformation, resulting in the plasmid puC18$^x$/623P (FIG. 5b), the BamHI site was restored and the KpnI site downstream from the "signal end" codon became unique, thus suitable for further manipulations and in vitro mutagenesis (see below).

6. In vitro mutagenesis of the "signal end" site: a one-base shift of the KpnI site in order to create a splice site being "in-phase" with the "signal end" codon (Ala).

To be able to ligate the 5'-blunt end of the HSA gene with the PHO5 signal coding sequence in the correct phase, the KpnI site has to be shifted by one base into the 5'-direction. It was noticed that the deletion of the adenosine residue (A) upstream from the KpnI site did not result in any changes in the nature of the encoded amino acids within the signal sequence

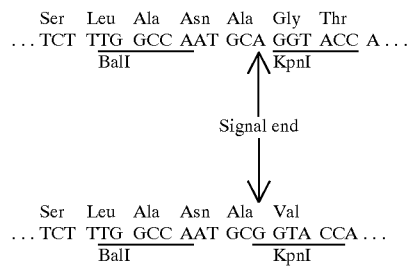

Cleaving the modified sequence with KpnI and then removing the protruding GTAC-3' nucleotides with DNA polymerase I Klenow fragment +dNTP generates a blunt end at which the KpnI site becomes in an exact coincidence with the position of the "signal end" codon (GCG).

To achieve the above mentioned structural change,

| the | CCAATGCAGGTAC | fragment of the pUC18*/623P |
|     | GGTTACGTC     | located between             |

BalI and KpnI sites was replaced by a synthetic linker

| CCAATGCGGTAC | resulting in plasmid |
| GGTTACGC     | pUC18*/622P. The replacement | was verified by sequencing (step 2. in FIG. 5).

Figure 5:
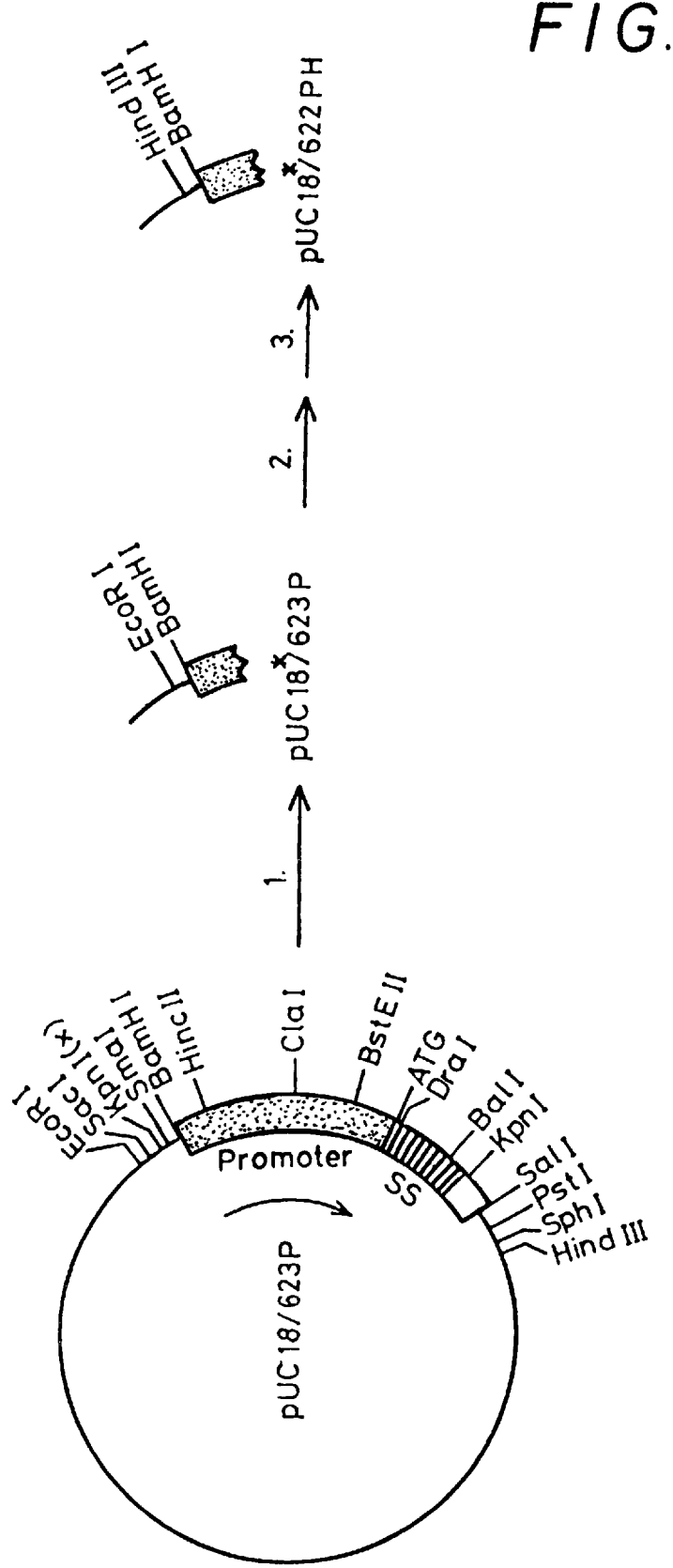
FIG. 5 shows the map of plasmid pUC18/623P (a.) containing the promoter of the yeast PHO5 gene and the modifications (1., 2. and 3.) leading to the construction of plasmids pUC18$^x$/623P (b.) and pUC18$^x$/622PH (c.).

For further cloning purposes the EcoRI site (upstream from the PHO5 promoter) was also replaced by a new HindIII site by inserting a HindIII linker (CAAGCTTG) at the filled-in EcoRI site (step 3. in FIG. 5). This new construction was called pUC18$^x$/622PH (FIG. 5c).

7. Construction of the plasmid pPT2HK1 containing the yeast expression cassette:

The plasmid pGB3-229T (FIG. 3) contains a SacI (SstI) and a KpnI site downstream from the Tc$^R$-gene. By inserting the PHO5 promoter region (at the unique HindIII and SalI sites from pUC18$^x$/622PH) the KpnI site from pGB3-229T would become superfluous, thus the KpnI site was deleted from pGB3-229T by KpnI digestion and removal of the protruding 3' end by the Klenow polymerase +dNTP, religation of the blunt ends and transformation. The new plasmid (pGB3-229TK°) (FIG. 3), lacking the KpnI site) was cleaved with HindIII and SalI and the HindIII-SalI fragment of pUC18$^x$/622PH (containing the modified PHO5 promoter and signal sequence) was cloned in, thus creating a tetracycline sensitive plasmid pPT2HK1 (FIGS. 3 and 6) which carries a functional yeast expression casette consisting of the in vitro mutagenized PHO5 promoter and signal-coding region and the transcriptional terminator of the HIS3 gene.

8. The construction of the E. coli-yeast shuttle vector plasmid pBY200.

The major points of consideration are:
to utilize the useful properties of the "classical" E. coli-S. cerevisiae shuttle vector plasmid pJDB207 (Beggs, J. D. (1981): Multiple-copy yeast plasmid vectors. Von Wettstein, D., Friis, J., Kielland-Bradt, M., and Stenderup, A. (eds) Molecular genetics in Yeast. Alfred Benzon Symposium Vol. 16, 383–390), i.e. 1) relatively small size in comparison with many other yeast cloning vectors; 2) high-copy-number replication of the plasmid in yeast host cells; 3) stable selection of the plasmid-containing yeast cells (of leu 2 phenotype) due to the presence of the LEU2 selective marker gene, giving 4) also possibility of direct selection in leub E. coli hosts;

to contain suitable restriction enzyme recognition sites that make it compatible with the E. coli plasmid pPT2HK1 carrying the yeast expression cassette (see above) and its recombinant derivatives.

Figure 7:
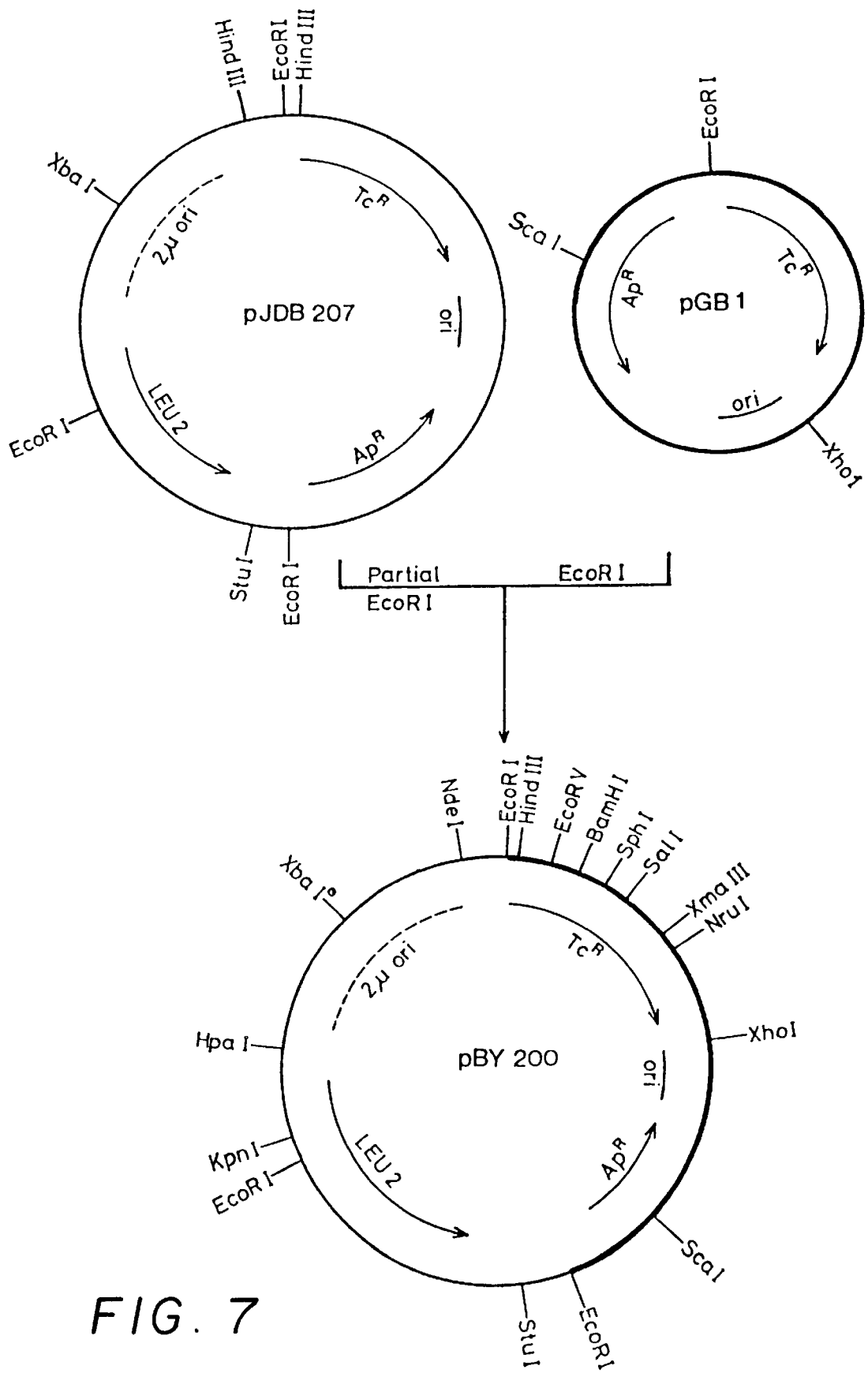
FIG. 7 shows the construction of the yeast-*E. coli* shuttle vector plasmid pBY200.

The plasmid pBY 200 was constructed by two steps of cloning (FIG. 7):
1. Insertion of the "LEU2+2µ ori" cartridge (a 3.4 kb EcoRI fragment obtained by partial EcoRI digestion of pJDB 207 (Beggs et. al., ibid). into the EcoRI site of pGB1;
2. Filling-in with DNA polymerase Klenow fragment (followed by religation of the blunt ends) of the Xba I site in the "2µ ori" region. This modification had no effect on the ability of the plasmid to replicate in S. cerevisiae.

Figure 6:
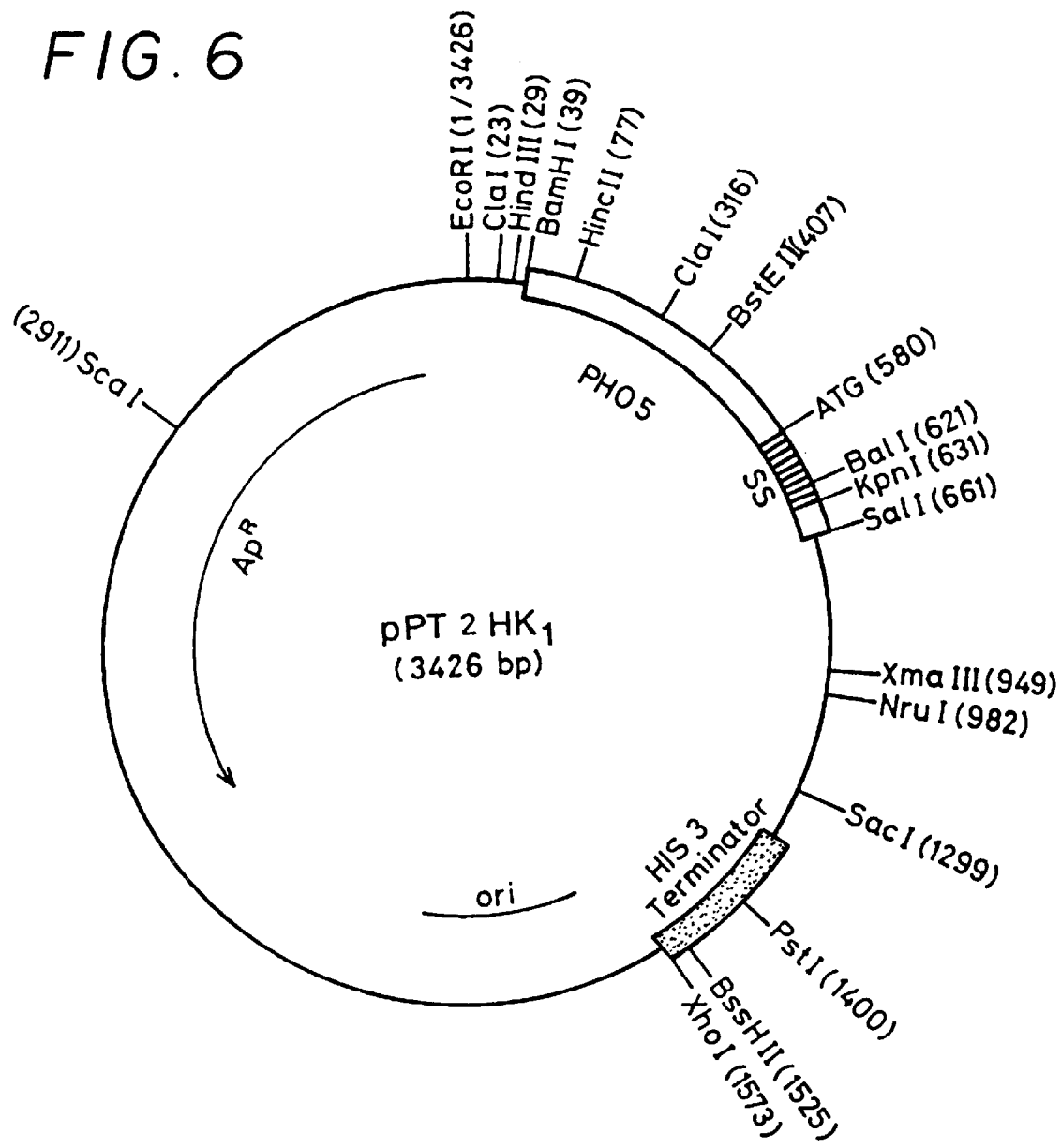
FIG. 6 shows the physical map of the basic expression vector plasmid pPT2HK$_1$.

Cloning the HSA Genes (No 1, No 2) Into pPT2HK$_1$ E. coli Vector pPT2HK$_1$ E. coli vector is shown in FIG. 3 and 6 and its modified signal sequence region is described above.

Its main features from the point of view of HSA gene cloning are that it contains the yeast PHO5 promoter and the PHO5 signal sequence as well as a yeast transcription terminator (HIS3). The promoter-signal sequence and the terminator regions are separated by unique restriction sites so that the HSA coding gene segment (structural HSA gene) can be inserted between these two regions.

In the pPT2HK$_1$ vector the restriction sites used to insert the HSA gene are KpnI and SacI sites. The KpnI site at the end of the signal sequence (leader peptide coding region) was previously shifted by us so that after KpnI cleavage followed by trimming of the resulting 3'-protruding region a blunt end was formed and this blunt end coincides exactly with the end of the leader peptide coding region (Scheme 42). The Sac I site is located upstream of the HIS3 termination region and the Sac I cleavage is performed after the Kpn I cleavage and blunt end formation.

pPT2HK$_1$ cleavage:
2 µg of pPT2HK$_1$ was treated with 20 units of Kpn I in 50 µl of low salt buffer at 37° C. for 2 hrs. After ethanol precipitation, the pellet was dissolved in 50 µl of Klenow buffer containing 0.1 mM dNTP and 2.5 units of Klenow polymerase and the reaction mixture was kept at room temperature for 10 min. The reaction mixture was phenol extracted and ethanol precipitated. The pellet was dissolved in 50 µl of low salt buffer and 20 units of SacI was added followed by incubation at 37° C. for 5 hrs. After ethanol precipitation, the large vector fragment was isolated by electrophoresis on a 0.5% agarose gel in TAE buffer followed by electroelution.

pHSA No 1 cleavage to obtain HSA No 1 fragment:
2 µg of pHSA No 1 dissolved in 50 µl of high salt buffer was treated with 20 units of PstI at 37° C. for 2 hrs. After ethanol precipitation, the pellet was dissolved in 50 µl of Klenow buffer containing 0.1 mM dNTP and 2.5 units of Klenow polymerase and the reaction mixture was kept at room temperature for 10 min. The reaction mixture was phenol extracted and ethanol precipitated. The pellet was dissolved in 50 µl of low salt buffer and 20 units of SacI was added. The mixture was kept at 37° C. for 5 hrs, then applied onto a 0.5% agarose gel (TAE buffer). The smaller fragment was isolated after electrophoresis followed by electroelution.

pHSA No 2 cleavage to obtain HSA No 2 fragment:
pHSA No 2 was reisolated from a dam$^{(-)}$ E. coli strain in order to be able to work with BclI enzyme, which is sensitive to adenine methylation.

2 µg of pHSA No 2 dissolved in 50 µl of buffer containing 75 mM KCl, 6 mM Tris-HCl, pH 7.4, 10 mM MgCl$_2$ and 1 mM DTT was treated with 20 units of BclI at 50° C. for 5 hrs. After ethanol precipitation, the pellet was dissolved in 50 µl of mung bean nuclease buffer and 10 units of mung bean nuclease was added at 37° C. for 30 min. After phenol extraction and ethanol precipitation, the pellet was dissolved in 50 µl of low salt buffer and 20 units of Sac I was added.

The mixture was kept at 37° C. for 5 hrs. The smaller fragment containing the HSA No 2 was isolated as it was described for HSA No 1.

Ligations:
0.1 µg of cleaved pPT2HK$_1$ and 0.2 µg of HSA No 1 or HSA No 2 fragment was mixed in 10 µl of ligase buffer and 80 units of T4 DNA ligase was added. The reaction mixtures were kept at 15° C. for 15 hrs, then they were transformed into JM 101 E. coli cells followed by plating onto LB-ampicillin plates. Colonies were tested by hybridization with 5'-$^{32}$P-HSA 5 oligonucleotide probe and approx. 10% of them were found to be positive. Plasmid DNA was prepared from 5—5 recombinants and they were sequenced by using HSA primer 9. Proper junction of PH05 leader sequence and HSA coding sequence was obtained in 2 cases for HSA No 1 and in 3 cases for HSA No 2. These plasmids are called pPT2/HSA No 1 and pPT2/HSA No 2, respectively.

In these constructions, the HSA gene is cloned in an E. coli plasmid between a yeast promoter+signal sequence and a yeast transscriptional terminator. In the next step, this "HSA expression cartridge" should be transfered into an E. coli-yeast shuttle vector.

Scheme 42

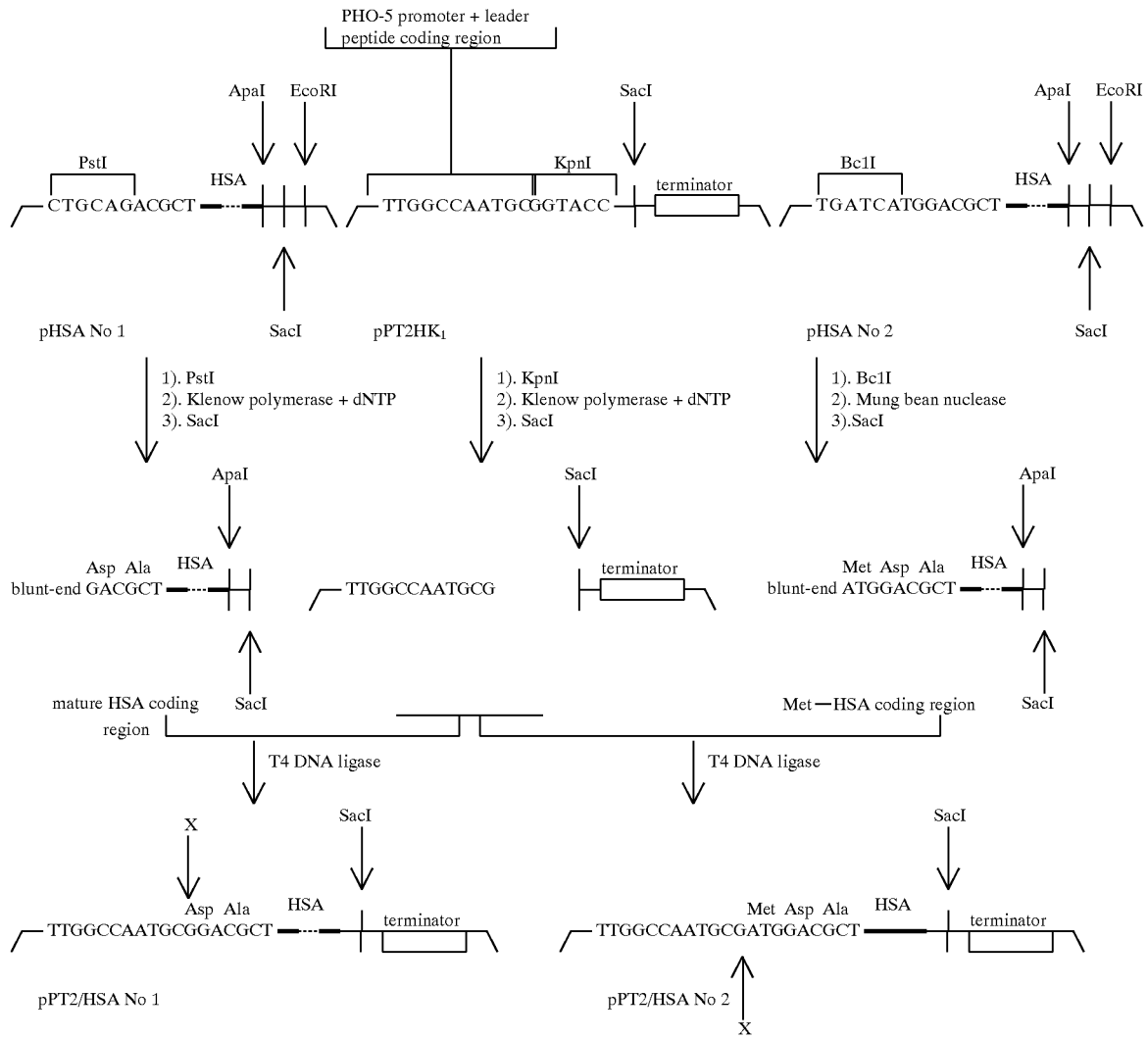

X shows the putative peptide processing site

Cloning the HSA Expression Cartridge Into pBY200 and pJDB 207

Figure 8:
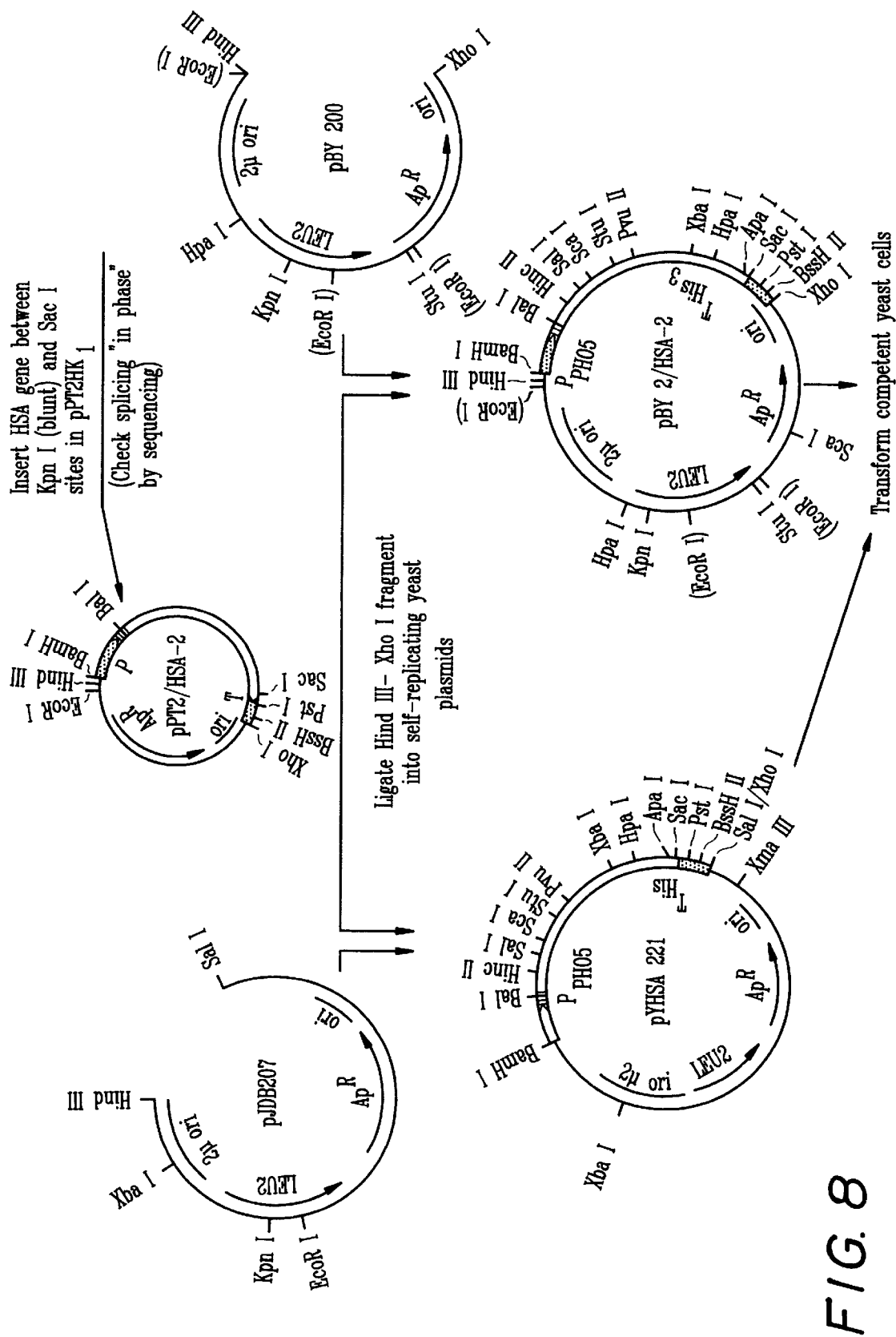
FIG. 8 shows the construction of two expression vector plasmids pYHSA 221 and pBY2/HSA containing the entire "HSA-expression cartridge" from pPT2/HSA.

The yeast-E. coli shuttle vector pBY200 contains both the yeast and E. coli replication origin, an $Ap^R$ region and a Leu2 marker. This plasmid can be cleaved with HindIII and XhoI enzymes so that the resulting large fragment keeps all the above mentioned region, and can serve as a vector to clone the HSA expression cartridge obtained from pPT2/HSA by HindIII and XhoI cleavages (FIG. 8).

pBY 200 cleavage:

5 μg of pBY 200 was dissolved in 100 μl of buffer containing 50 mM NaCl, 10 mM Tris-HCl pH 7.5, 10 mM $MgCl_2$ and 2 mM DTT (medium salt buffer) and was treated with 40 units of HindIII and 60 units of XhoI at 37° C. for 6 hrs. The large fragment was isolated by gel electrophoresis on a 0.5% agarose gel in TAE buffer followed by electroelution.

pJDB 207 cleavage:

Similarly, the yeast-E. coli shuttle vector plasmid was cleaved with HindIII and SalI restriction enzymes under conditions described above for the pBY200 except that 45 units of SalI was used instead of XhoI. The large vector fragment (FIG. 8) was isolated by electrophoresis and purified from agarose gel by electroelution.

pPT2/HSA cleavage:

5 μg of pPT2/HSA No 1 or pPT2/HSA No 2 was treated as above in 100 μl of medium buffer with HindIII and XhoI enzymes. The larger fragment was isolated in both cases by electrophoresis on a 0.5% agarose gel followed by electroelution.

Ligation:

0.2 μg of XhoI-HindIII cleaved pBY 200 was mixed separately with either 0.2 μg of XhoI-HindIII fragment of pPT2/HSA No 1 or 0.2 μg of XhoI-Hind III fragment of pPT2/HSA No 2 in 10 μl of ligase buffer and 80 units of T4 DNA ligase was added to both mixtures which were kept at 15° C. for 15 hrs. The reaction mixtures were transformed into frozen competent E. coli cells (JF 1754) followed by plating on LB-ampicillin plates. Similar condition were used for ligation of the XhoI-HindIII fragment of pPT2/HSA No 1 into pJDB 207 cleaved with HindIII and SalI.

Selection and Analysis of pBY2/HSA No 1 and pBY 2/HSA No 2 Recombinants

Colonies grown upon LB-ampicillin plates were picked onto 1.) M9 minimal plate containing 20 μg/ml methionine and 20 μg/ml histidine (but lacking leucine), 2.) LB-tetracycline plate and 3.) a nitrocellulose filter placed onto an ampicillin-LB plate. Colonies grown up on the nitrocellulose filter were lysed and hybridized with $^{32}$P-labeled HSA 6 oligonucleotide probe. Positive colonies which were tetracycline sensitive on plate 2 and showed leu complementation on plate 1 (i.e. did not grow on plate 2 but grew up on plate 1) were selected and plasmid DNA was prepared from them (approx. 20% of the total colonies obtained on LB-ampicillin plate showed the expected phenotype on plates 1–3). Recombinant plasmid DNAs were cleaved with the mixture of XhoI and HindIII and the cleavage was checked by electrophoresis on a 0.5% of agarose gel in TBE buffer. Upon this double-cleavage, both pBY2/HSA No 1 and pBY2/HSA No 2 gave two fragments with sizes corresponding to the size of the starting pBY 200, pPT2/HSA No 1 and pPT2/HSA No 2 fragments, respectively. At the same time, KpnI cleavage resulted in a linearized vector in both cases. In order to control the structure of pYHSA 221 the recombinant plasmid was cleaved with XbaI resulting in two fragments with sizes expected from the physical map (FIG. 8).

Figure 9:
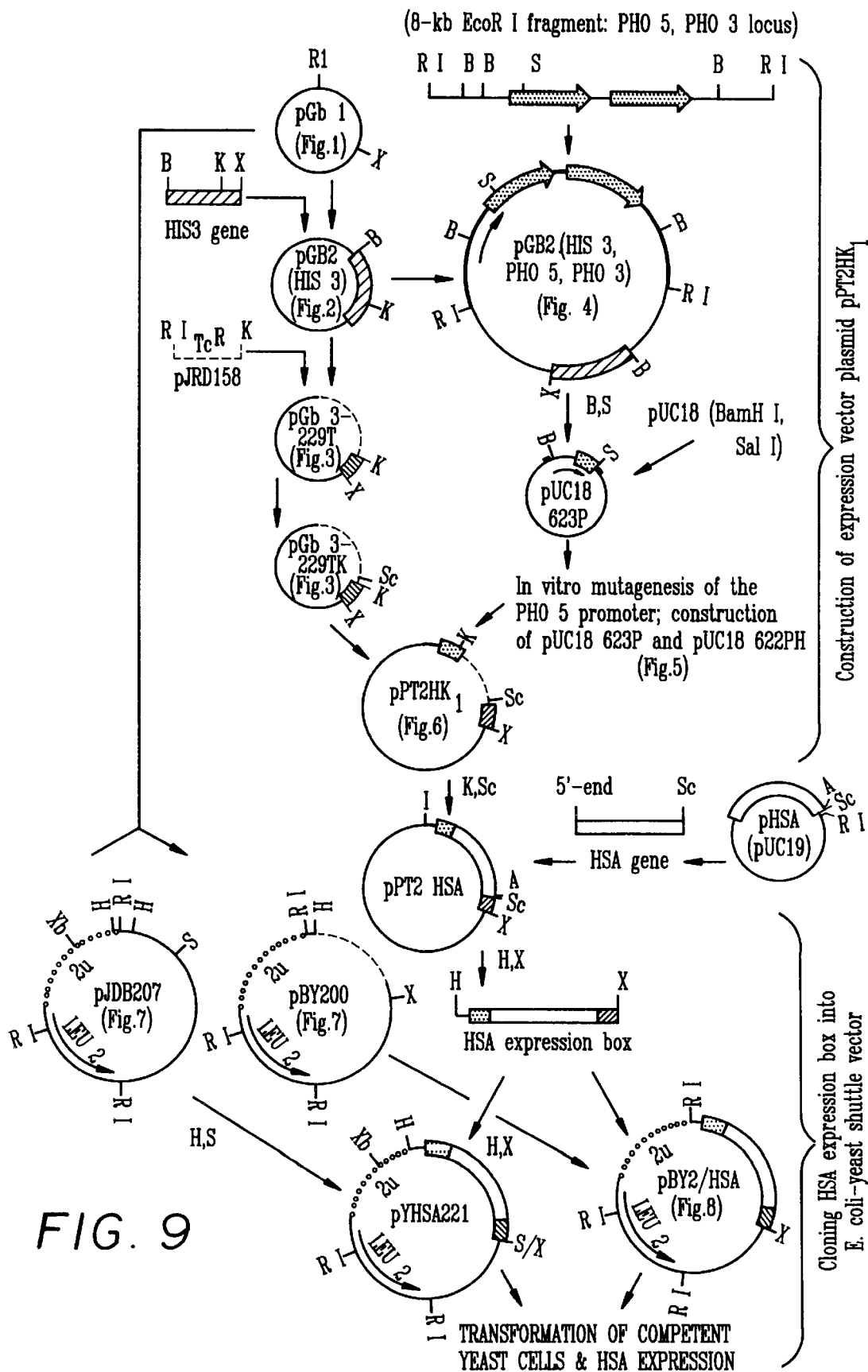
FIG. 9 shows the flow diagram of the construction of yeast vectors to express a synthetic HSA gene.

All the plasmid constructions and cloning steps leading to the yeast expression vectors containing the HSA gene are summarized in FIG. 9.

Expression of the Synthetic HSA Gene in Recombinant Yeast Cells

Transformation of yeast cells and culture conditions for the induction of the PHO 5 promoter:

The synthetic HSA gene was placed under control of the yeast PHO 5 promoter in a series of manipulations described in details above leading to the construction of the yeast-E. coli shuttle plasmid pBY2/HSA No 1 and pBY2/HSA No 2, and pYHSA 221 (FIG. 8). Yeast cells (LL 20; Leu 2-3, 112, His 3-11, 15: Storm, et. al., ibid) were transformed either by the spheroplast-PEG method of Beggs, J. D. (Nature 275, 104, (1978)) or Ito, H. et. al. (J. Bacteriol. 153, 163 (1983)).

The recombinant yeast cells were selected on the basis of their His$^-$, Leu$^+$ phenotype and tested for the presence of the transforming plasmids by reisolating said plasmids from 10-ml cultures by the method of Holm et al. (Gene 12, 169 (1986)) and analysing their structure by restriction enzyme cleavage and electrophoresis on 1% agarose gel. The recombinant yeast cells in each case contained transforming expression vector plasmids of the proper size and structure. These cells were grown in YNB medium (Difco) containing 2% glucose and 0.15% KH$_2$PO$_4$ to OD$_{600}$ of 2.0, harvested and diluted into a low-phosphate YNB medium (containing 30 mg KH$_2$PO$_4$ per liter, to activate the PHO 5 promoter), and were regrown for 60 hrs before harvesting (OD$_{600}$~2.0). The cells were then washed with 0.1M Na-phosphate buffer, resuspended in one hundredth volume of the same buffer containing 1% Triton X-100, 0.1 mM phenylmethyl-sulphonyl fluoride (PMSF) and broken by vortexing with glass beads (Sigma, type IV, 250–300 microns). Alternatively, the cells were washed and resuspended in 1M sorbitol and incubated with β-glucuronidase (Boehringer; 1% solution) in 100 mM β-mercaptoethanol at 30° C. to produce protoplasts which were then lysed with 1% Triton X-100. Cell extracts were clarified by centrifugation at 10 000 rpm for 15 min resulting in the so called "periplasmic fraction" in which HSA was assayed by the following immunological and electrophoretic methods.

Micro-ELISA test:

The ELISA plates were coated with anti-HSA-Ab (purified from horse serum—a product of HUMAN, Hungary—on Protein A-Sepharose 4B columns) and saturated with 0.5% Gelatine (Sigma). 100 μl of clarified yeast cell extract was layered in appropriate dilutions onto the coated wells and incubated for 1 hour at 37° C. The HSA-anti-HSA-Ab binding was monitored by a conventional color reaction by using biotinylated horseradish peroxidase-streptavidine complex, H$_2$O$_2$ as substrate and ortho-phenylene diamine as developer.

Serial dilutions ranging from 2 μg to 15 μg of purified HSA (Reanal, Hungary) per well were used as reference for calibration. A thousand-fold dilution of human serum was used as a positive control, gelatine-coated wells as well as extracts from non-recombinant yeast cells (LL 20, processed as for the HSA assay) served as negative controls in micro-ELISA tests. The color reactions were evaluated in a microplate reader of Cambridge Life Sciences Ltd., UK.

Immunoprecipitation of $^{35}$S-Methionine-labeled-proteins:

The whole-cell proteins of the recombinant yeast cells were labeled for 16 hours at 30° C. with $^{35}$S-methionine by culturing the yeast cells in "low-methionine, low-phosphate" YNB medium containing 40 μCi of $^{35}$S-methionine per milliliter.

20 μl of horse anti-HSA serum was added to 10$^8$ cell equivalents of clarified cell lysates (0.5 ml) for 90 minutes at 4° C. in 0.1M phosphate buffer, pH 8.0. The immunoprecipitates were adsorbed onto 1-ml protein A-Sepharose (Pharmacia) for 90 minutes at 4° C. and washed. Immunoprecipitated proteins were eluted from the protein A-Sepharose beads (Conner, G. E. et. al., J. Exp. Med. 156, 1475, 1982) and resolved on a 15 percent SDS-polyacrylamide gel and fluorographed. Clarified extracts obtained from $^{35}$S-methionine-labeled non-recombinant LL 20 cells and that of a recombinant yeast strain expressing the hepatitis B surface antigen (HBsAg) were used as controls.

Results:

The yeast cells transformed with the plasmids pBY2/HSA No 1 and pYHSA221 exhibited active production of the HSA protein which could be readily detected by ELISA as well as precipitated with specific antiserum directed against HSA.

According to the micro-ELISA test the proportion of the of HSA ranged between 3–8% of total cell protein.

Figure 10:
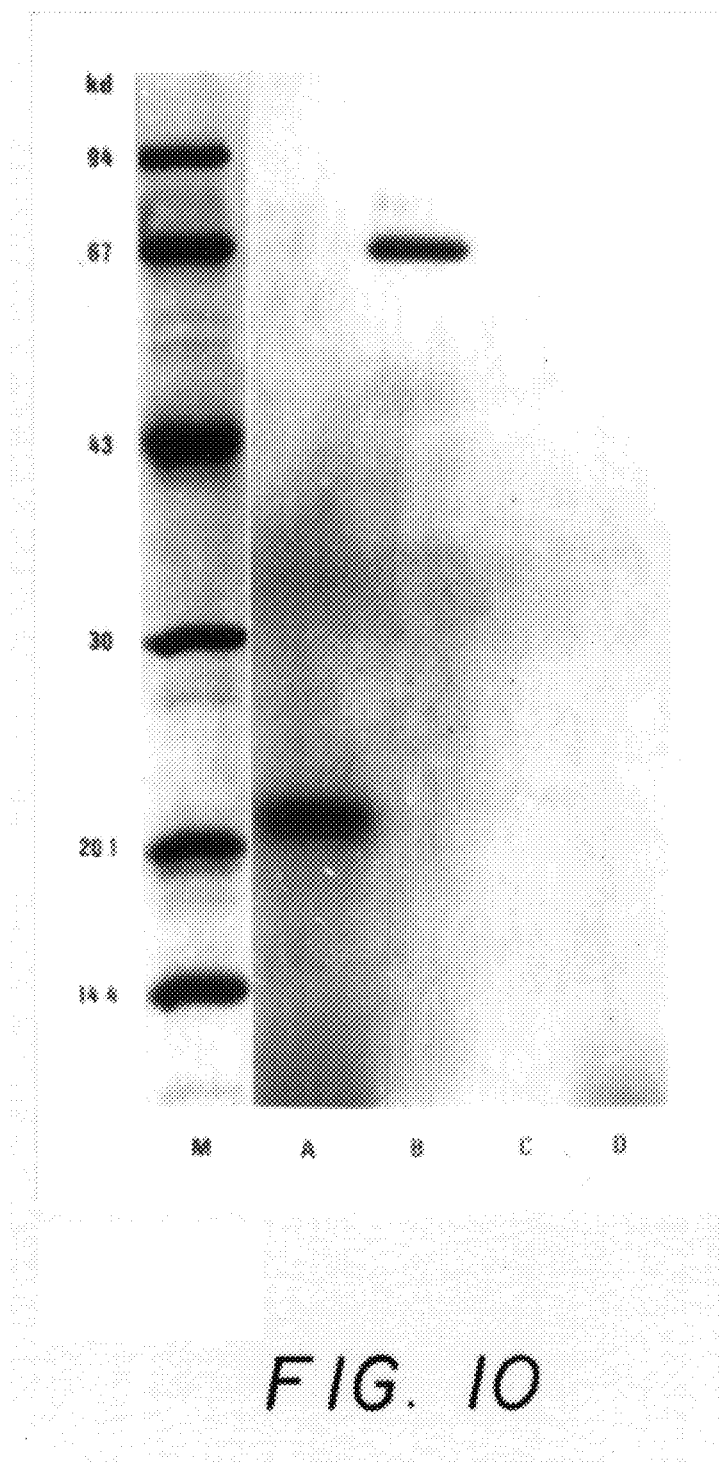
FIG. 10 shows the fluorograph of the $^{35}$S-methionine-labeled proteins immunoprecipitated with horse anti-HSA serum and resolved in SDS-polyacrylamide gel.

FIG. 10 shows the fluorograph of the $^{35}$S-methionine-labeled proteins obtained from the periplasmic fraction and immunoprecipitated with goat anti-HSA serum and resolved in SDS-polyacrylamide gel.

Track M—$^{14}$C-protein molecular weight marker mix (BRL); track A—recombinant $^{35}$S-HBsAg precipitated with anti HBsAg antibodies; track B—labeled HSA produced in the recombinant yeast precipitated with anti-HSA serum; tracks C and D demonstrate the lack of cross-immunreactions of anti-HSA serum with HBsAg-containing yeast lysate and that of anti-HBsAg serum with the HSA lysate, respectively.

The electrophoretic mobility of the immunoprecipitated HSA was approximately the same as that of the 67 kd labeled protein marker. This result indicates that the majority of the HSA protein secreted into the periplasmic space by the expression vector construction involving the entire signal peptide of the PHO 5 gene is correctly processed yielding a protein product with the size of the mature (natural) HSA.

Two independent immunoblotting experiments (western blots) revealed a protein of the same molecular mass.

Laboratory-Scale Purification of Expressed HSA From Yeast Cultures 500-ml culture of yeast cells transformed with either pBY2/HSA or pYHSA 221 was grown at 30° C. to OD$_{600}$=

2.0 (usually 24–28 hours) in 0.67% YNB medium (DIFCO) containing 0.15% (w/v) $KH_2PO_2$ 20 mg/liter L-histidine and 2% (w/v) glucose. The cells were collected by centrifugation at 2000×g for 5 min and resuspended in 10 liters of 0.67% (w/v) YNB medium containing 30 mg/liter $KH_2PO_4$, 0.1% (w/v) KCl, 20 mg/liter L-histidine and 2% (w/v) glucose. Following 60 hours of culture growth (to $OD_{600}$ 1.8–2.0) the cells were harvested by centrifugation (4000×g, 5 min) washed twice with ice-cold distilled water and resuspended in 200 ml 0.1% Triton X-100, 0.5M NaCl, 20 mM Tris/HCl, pH 7.5, 100 mM β-mercaptoethanol and 1 mM PMSF. The cells were homogenized for 60 sec. in pre-cooled glass-bead cell homogenizer (Model: Braun MSK). The cell extract was clarified by high-speed centrifugation (at 20 000×g, 4° C., for 30 min). The pH of the clarified lysate was adjusted (by dropwise addition of 1M HCl) to 4.8–5.0, then saturated solution of $(NH_4)_2SO_4$ was added to a final concentration of 60% of saturation. The mixture was stirred for 2 hrs in ice-water bath, then centrifuged in Sorvall RC-5C centrifuge for 30 min at 18 000 rpm (2° C.). The pellet was dissolved in 100 ml of 50 mM Bis-Tris buffer, pH 6.5, followed by dialysis overnight against 20 volumes of the same buffer. The dialysed lysate was centrifuged for 30 min, (18,000 rpm, 2° C.) and the clear supernatant was applied onto a Superose MONO Q HR 5/5 FPLC column (Pharmacia) equilibrated with the same buffer.

The anion exchange chromatography as well as all successive chromatographic purification steps were performed on a Pharmacia FPLC system.

After a short linear gradient of NaCl (0.0–0.1M) proteins eluting with 0.1M NaCl (isocratic elution:) were collected and dialysed against 0.05M Na-phosphate buffer, pH 7.5. This fraction was subjected to hydrophobic interaction chromatography on Alkyl-Superose HR 5/5 column.

Solid ammonium sulfate was added to the above dialysed fraction, the final concentration to be adjusted to 2.0M, and the sample was loaded onto Alkyl-Superose HR 5/5 column equilibrated with 2M $(NH_4)_2SO_4$ in 50 mM Na-phosphate buffer. Bound proteins were eluted with linear descending-concentration gradient of $(NH_4)_2SO_4$. The HSA-containing fraction was eluted at about 1.2M $(NH_4)_2SO_4$ which was monitored by SDS-PAGE of the eluted fractions.
Gel-filtration.

The "HSA" fraction from the previous step was concentrated by ultrafiltration in an Amicon stirred cell (filter: PM-30), then loaded onto Superose 12 HR 10/30 column equilibrated with 50 mM Na-phosphate buffer, pH 7.5 containing 0.15M NaCl. The first large peak upon gel-filtration contained highly purified monomeric HSA as was tested by SDS-PAGE, according to Laemmli U.K., Nature 227, 680 (1970). Additional molecular analyses included PAGE at "native" conditions, IEF and limited CNBr-cleavage (Barsh, G. S., and Byers, P. H., 1981. Proc. Natl. Acad. Sci. USA 78:5142–5146).

Molecular Properties of HSA Purified From Recombinant Yeast

The HSA purified from yeast cells was shown to run as a single 68-kilodalton protein band in SDS-polyacrylamide gels indicating that it has the same molecular mass as the mature natural HSA.

Electrophoresis in native conditions (carried out on PHARMACIA's 10–15% PHAST GELS according to the manufacturer's instructions) indicated that the behaviour of HSA produced by yeast was similar to that of natural mature HSA and had also similar tendency to form double, triple and multimer complexes probably by random formation of intermolecular —S—S— bridges.

The absence of glycosylation in HSA produced in yeast was proven by Con A-Sepharose chromatography:

500 μg of a partially purified protein extract obtained from HSA-producing yeast cells was allowed to bind to 750 μl of swollen Con-A-Sepharose (Pharmacia) in 1.5 ml of buffer containing 20 mM Tris-HCl, pH 7.4, and 0.5M NaCl. The suspension was slowly shaken overnight at 4° C. and the Con A-Sepharose was separated from the buffer (containing the unbound proteins:) by centrifugation at 12 000×g for 10 min. The Con A-Sepharose gel was then washed with 100 ml of same buffer by filtration through a 25-mm circle of Whatman GF/A filter.

The bound proteins were eluted by a buffer containing 20 mM Tris-HCl, pH 6.8, 0.25M α-D-methyl-mannoside (Serva) and 0.25M NaCl.

Both the unbound and bound (to Con A-Sepharose) protein fractions were dialysed against 10 mM Tris-HCl (pH 6.8) and subjected to 1) SDS-PAGE according to Laemmli, U.K. (Nature 227, 680 (1970)), and 2) ELISA-test in order to control the presence of HSA.

A similar approach was applied for a fraction of purified HSA.

In each case, the SDS-PAGE and ELISA tests revealed the absence in the fraction of Con A-binding proteins of any 68 kd protein as well as any proteins showing immunological reactions with anti-HSA-Ab. The HSA was quantitatively recovered from the protein fraction which did not bind to Con A-Sepharose upon application of the sample.

The results strongly indicate the absence of glycosylation in the molecules of HSA produced in yeast.

Prior to peptide mapping by limited proteolysis the samples were heat-denatured in the presence of 0.5% (w/v) SDS without addition of a reducing agent, and subjected to enzymatic digestions for 10 to 20 minutes. Subtilisin, thermolysin, trypsin and papain were used. The cleavage by CNBr was carried out as described by Barsh et al. (ibid).

Figure 12:
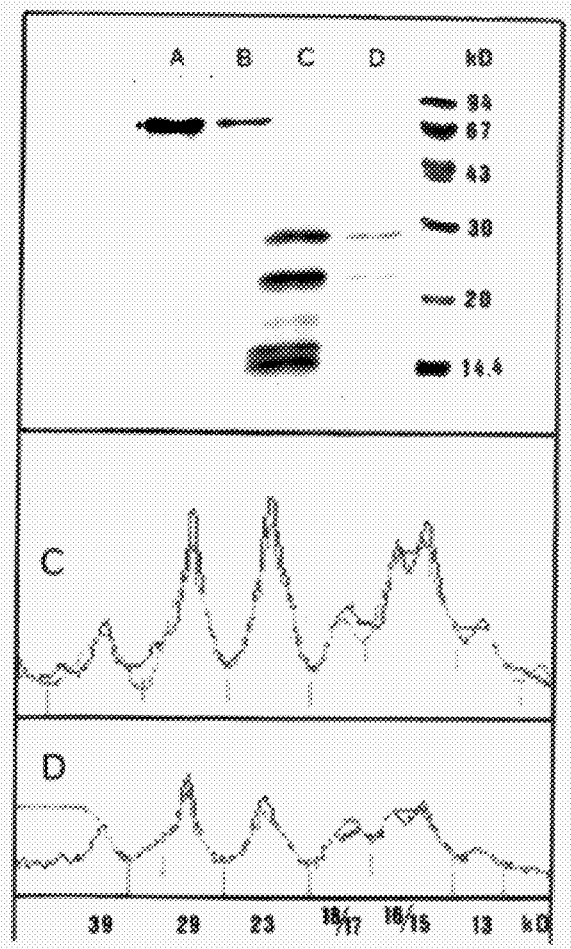
FIG. 12 shows the products of CNBr-cleavage of purified natural HSA (A and C) and of yeast-produced HSA (B and D) resolved by SDS-polyacrylamide gelelectrophoresis. The Commassie-stained gel was also subjected to laser-scanning (using LKB-Ultro-Scan).

FIG. 12 shows the CNBr cleavage pattern of natural HSA (A and C) (purified as described above from commercial sources) and yeast-produced HSA (B and D), as demonstrated by SDS-PAGE separation of the cleaved polypeptides. After digestion, SDS and β-mercaptoethanol were added to concentrations (w/v) 2.5% and 10%, respectively. The samples were loaded onto 8–25% gradient PHAST GEL (PHARMACIA) and the electrophoresis was carried out in a PHARMACIA PHAST SYSTEM according to the manufacturer's instructions.

The results obtained indicate that the HSA purified from recombinant yeast showed cleavage patterns by proteolytic enzymes and cyanogen bromide similar to those of natural HSA (with a note that the yeast-produced HSA was less accessible to papain digestion under the conditions used than the natural HSA).

A sample of the HSA purified from yeast was subjected to N-terminal sequencing on an Applied Biosystems Model 470 A gas phase sequencer. The result of the sequencing did not reveal any other amino acid residues than those expected.

Construction of Plasmid Vectors Promoting the Secretion of the HSA Into the Culture Medium The experimental strategy for the construction of new expression-secretion vectors was based on the finding that prepro HSA was correctly processed in vitro by the yeast KEX2 endopeptidase yielding mature Asp-Ala-HSA (Bathurst, I.C. et al., 1987, Science 235, 348–350). The natural N-terminal HSA prepro-leader peptide was evaluated as a sequence capable of promoting the secretion of HSA from the recombinant yeast.

The sequence of a 103-mer synthetic DNA fragment coding for the HSA prepro$^x$-leader peptide was designed as follows:

```
                                    M    K    W    V    T    F
                                    Met  Lys  Trp  Val  Thr  Phe
GATCAAAAACACTAAAATATAATCAAA         ATG  AAG  TGG  GTT  ACT  TTC

I    S    L    L    F    L    F    S    S    A    Y    S    R
Ile  Ser  Leu  Leu  Phe  Leu  Phe  Ser  Ser  Ala  Tyr  Ser  Arg
ATC  TCT  TTG  TTG  TTC  TTG  TTC  TCT  TCT  GCT  TAC  TCT  AGA

G    V    F    K$^x$  R
Gly  Val  Phe  Lys    Arg
GGT  GTT  TTC  AAG    AGG  CCT  G
                           ‾‾‾‾‾‾‾‾
                           Stu 1
```

The sequence (27 nucleotides) upstream of the ATG codon was designed to be closely homologous to the downstream end of a strong constitutive yeast promoter, i.e. that of the gene coding for glyceraldehyde-3-phosphate dehydrogenase (GAPDH; Holland, J. P. and Holland, M. J., 1979, J. Biol. Chem. 254, 9839–9845). Other characteristic features of the above DNA sequence include the usage of the most frequent yeast codons, as well as an "ideal" KEX2 cleavage site (K-R; Kurjan, J., Hershkovitz I., 1982. Cell 30, 933–943) coded by the AAG AGG codons which—according to this design—coincides with a Stu I restriction endonuclease digestion site.

1. Construction of pHSA-T plasmid containing the gene for HSA No 1 and the yeast His3 transcriptional terminator The 1.8 Kb Hind III-SacI fragment from pHSA No. 1 (i.e. the gene coding for HSA) was cloned into pGB3-229TK° (FIG. 3b) at the Hind III and SacI sites. Prior to this cloning step the PstI site (located in the His3 terminator region) was deleted, since it would become double after the insertion of the HSA gene.

0.5 μg of pGB3-229TK° was treated with 10 units of PstI in 20 μl of medium salt buffer at 37° C. for 2 hrs. After phenol extraction and ethanol precipitation the pellet was dissolved in 50 μl of Klenow buffer containing 0.1 mM dNTP and 2.5 units of Klenow polymerase, and the reaction mixture was kept at room temperature for 40 min. The reaction mixture was then phenol extracted and ethanol precipitated. The DNA pellet was dissolved in 100 μl of ligase buffer and 50 units of T$_4$ DNA ligase was added. The ligase reaction was carried out at 15° C. for 15 hours, followed by transformation of E. coli JM 109. Plasmids (from about 30% of all transformants) containing no PstI site (designated as pGB3T) were selected and used for the insertion of the HSA gene as follows:

a) 2 μg of pGB3T was digested with 10 units of SacI in low salt buffer, at 37° C. for 4 hrs, in a final volume of 20 μl. The buffer was then adjusted to be optimal for Hind III digestion, 10 units of Hind III was added (final volume 40 μl) and the treatment was carried out for additionally 4 hrs at 37° C. The 2.06 Kb vector was separated in 0.8% agarose gel.

b) 5 μg of pHSA No. 1 was digested by SacI and Hind-III as described above. The 1.8 Kb HSA fragment was isolated from 0.8% agarose gel.

c) The ligation of the 2.06 Kb pGB3T vector and the 1.8 Kb HSA insert was carried out in 20 μl ligation mix (containing 80 units of T$_4$ DNA ligase) at 15° C. for 16 hrs. E. coli JM109 cells (Yanisch-Perron, C., et. al., ibid) were transformed. Plasmids isolated from tetracycline sensitive transformants were tested for restriction enzyme digestion pattern, viz. by double-digestion with SalI and XhoI.

Figure 11:
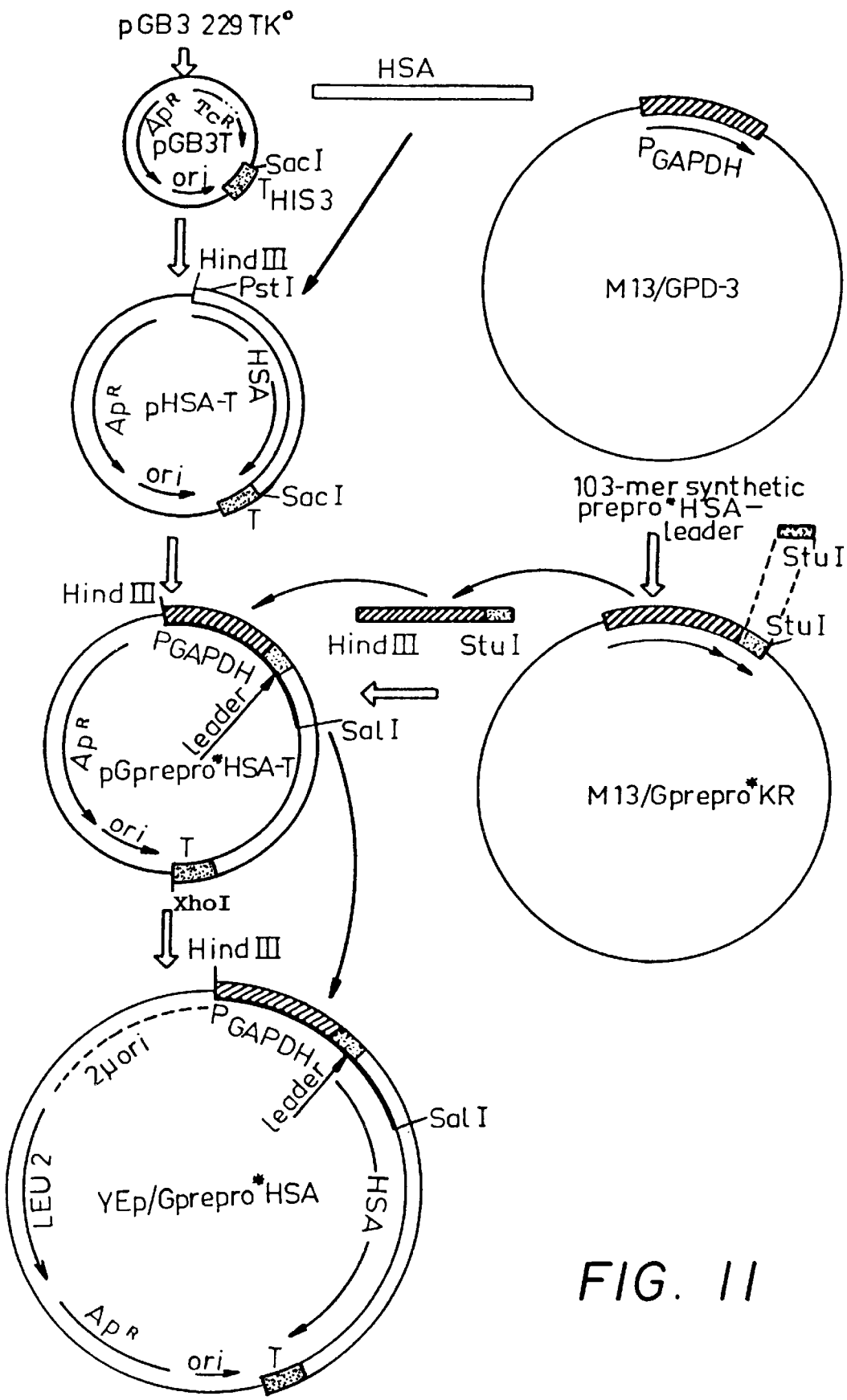
FIG. 11 shows the construction of a yeast expression plasmid containing an artificial prepro-leader coding sequence and an artificial gene coding for HSA (No 1).

The resulting plasmid was designated as pHSA-T (FIG. 11).

2. Insertion of a strong constitutive promoter and the artificial prepro-leader sequence into pHSA-T; construction of the plasmid pGprepro$^x$HSA-T (FIG. 11).

a) Cloning of the artificial prepro$^x$-leader-coding sequence downstream of the GAPDH promoter.

0.5 μg of M13/GPD-3 (RF) DNA (Bitter, G. A. and Egan, K. M. (1984): Gene 32, 263–274) was treated with 5 U of EcoRI in medium salt buffer for 2 hrs at 37° C. followed by digestion by 5 U of BamHI for additional 2 hrs at 37° C. in high salt buffer. The digestions were terminated by phenol extraction and ethanol precipitation. The DNA pellet was washed with 70% ethanol, dried under vacuum and dissolved in 5 μl H$_2$O for ligase reaction with the artificial HSA prepro$^x$-leader.

The ligation mixture contained the EcoRI-BamHI-treated M13/GPD-3 DNA, 1 pmole of the synthetic double-stranded 103-mer DNA fragment (coding for prepro$^x$-leader) and 80 U of T$_4$ DNA ligase, in 20 μl ligase buffer. The ligase reaction was carried out at 15° C. for 16 hrs, after which E. coli JM 109 was transformed.

The phage transformants were screened for the insertion of the 103-mer BamHI°-EcoRI prepro$^x$-leader-coding fragment by the dideoxynucleotide sequencing method.

The transformants containing the HSA prepro$^x$-leader-coding sequence placed behind the GAPDH promoter were named M13/G prepro$^x$KR (FIG. 11.) ("KR" indicates Lys-Arg and G denotes the GAPDH promoter).

Cloning the HSA gene behind the GAPDH promoter-preprox$_x$ sequence fusion: construction of pGprepro$^x$HSA-T a) pHSA-T was digested with PstI (0.5 μg DNA, 5 U PstI, 4 hrs at 37° C.) and the cleaved 3'-protruding end was made blunt by treatment with the Klenow polymerase. The linearized plasmid was then further cleaved with 5 U of Hind III (4 hrs at 37° C.), followed by phenol extraction and ethanol precipitation.

b) The GAPDH promoter+artificial prepro$^x$-leader-coding sequence was isolated from M13/G prepro$^x$KR by simultaneous digestion of 5 μg plasmid DNA with 20 U of Hind III and 20 U of Stu 1 (5 hrs at 37° C. in medium-salt buffer). The 0.75 Kb promoter+prepro$^x$ fragment was isolated by electrophoresis in 1% agarose gel, electroeluted, phenol extracted and ethanol precipitated.

c) The purified promoter+prepro$^x$ fragment was ligated into the PstI (blunt)-Hind III-treated vector pHSA-T (in 20 μl mix, at 15° C. for 16 hrs) followed by transformation of E. coli JM 101. The resulting plasmid, pGprepro$^x$HSA-T (FIG. 11) was tested by mapping restriciton endonuclease cleavage sites.

Construction of the Yeast—E. coli Shuttle Vector Containing the Prepro$^x$-HSA-Expression—Secretion Cassette The prepro$^x$-HSA expression cassette was isolated from pGprepro$^x$HSA-T (by HindIII+XhoI digestion; 2 μg DNA, in 20 μl high-salt buffer, 10 U of HindIII and XhoI each at 37° C. for 10 hrs followed by electrophoretic separation on a 0.8% agarose gel, electroelution, phenol extraction and ethanol precipitation). The HindIII—XhoI fragment was then ligated into pJDB207 (between HindIII and SalI sites) resulting in YEp/Gprepro$^x$ HSA (FIG. 11) which was used to transform yeast LL20. Yeast transformants were selected on YNB-agar plates (lacking leucine). The expression and secretion of HSA was tested in shake-flask cultures as described below.
Expression and secretion of HSA by the recombinant yeast transformed with pYEprepro$^x$HSA (YEprepro$^x$-HSA).

A single colony of the yeast YEprepro$^x$HSA was inoculated into 10 ml of YNB medium containing 2% glucose and 200 μg/ml histidine and the cells were grown overnight at 30° C. with continuous shaking. 1 ml of the overnight culture was diluted into 200 ml of the above medium and further grown to OD$_{600}$=2.0. The cells were precipitated by centrifugation (6000 r.p.m.; 4° C.; 15 min), the supernatant was saved and concentrated 10 times by using an Amicon stirred ultrafiltration cell with PM-30 filter. The concentrated cell medium was then dialysed overnight against 20 mM Tris/glycine, pH 8.3, 1 mM EDTA, 5 mM β-mercaptoethanol and 0.01% SDS. Secreted HSA was assessed by quantitative micro-ELISA as described above.

It was found that at least 3000 μg HSA per 100 ml culture medium was produced by the yeast cells YEprepro$^x$HSA.

The secreted HSA was subjected to SDS-polyacrylamide gel-electrophoresis followed by immunoblotting and staining by conventional methods.

Figure 13:
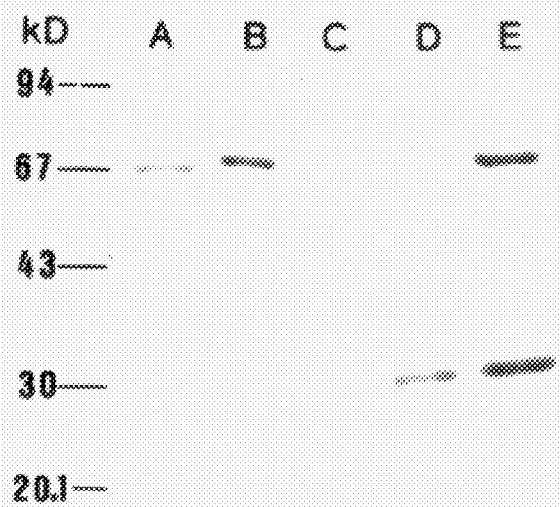
FIG. 13 shows a Western-blot of HSA expressed and secreted by the yeast "YEprepro$^x$-HSA" (tracks B and C) compared to proteins expressed by YHSA-221 (tracks D and E). Track A shows a purified HSA sample.

It was shown (FIG. 13) that, although mature HSA (68 Kd) was the major product observed in the culture medium, a fragment of HSA with a molecular mass of . 46–48 Kd was also detected representing approximately ⅓ of the total HSA produced. The 68 Kd mature HSA could be readily purified by a series of chromatographic steps and gelfiltration (on Superose 12 HR$^{10}$/30) as previously described in connection with Laboratory-scale purification of expressed HSA from yeast cultures.

We claim:

1. A structural gene coding for authentic human serum albumin, which comprises a nucleotide sequence wherein the codons have been selected with regard to a yeast host which has known codon use and which has been chosen for expression of authentic human serum albumin, whereby the selection of the codons has been effected so that, in the first instance, the codons most frequently used by the yeast host were selected, and in the second instance, the codons used by the yeast host in the second or third place were selected, to avoid the appearance of such restriction sites which are to be used during the assembly of the gene, to create one unique cleavage site for a specific enzyme, and to eliminate 8-base-pairs long or longer palindromes within such parts of the gene which are to be chemically synthesized and cloned.

2. A structural gene according to claim 1, wherein the nucleotide sequence is

```
GAC GCT CAC AAG TCT GAA GTC GCT CAC AGA TTC AAG GAT

CTA GGT GAA GAA AAC TTC AAG GCT TTG GTT TTG ATT GCT

TTC GCT CAA TAC TTG CAA CAA TGT CCA TTC GAA GAC CAC

GTC AAG TTG GTC AAC GAA GTT ACT GAA TTT GCT AAG ACC

TGT GTT GCT GAC GAA TCT GCT GAA AAC TGT GAC AAG TCC

TTG CAC ACT TTG TTC GGT GAC AAG TTG TGT ACT GTT GCT

ACT TTG AGA GAA ACT TAC GGT GAA ATG GCT GAC TGT TGT

GCT AAA CAG GAA CCA GAA AGA AAC GAA TGT TTC TTA CAA

CAC AAG GAC GAC AAC CCA AAC TTG CCA AGA TTG GTT AGA

CCA GAA GTC GAC GTT ATG TGT ACT GCT TTC CAC GAC AAC

GAA GAG ACT TTC TTG AAG AAG TAC TTG TAC GAA ATC GCC

AGA AGA CAC CCA TAC TTC TAC GCT CCA GAA TTG TTG TTC

TTC GCT AAG AGA TAC AAG GCT GCT TTC ACT GAA TGT TGT
```

-continued

CAA GCT GCC GAC AAG GCT GCT TGT TTG TTG CCA AAG TTG

GAC GAA TTG AGA GAC GAA GGT AAG GCT TCT TCC GCT AAG

CAA AGA TTG AAG TGT GCT TCC TTG CAA AAG TTC GGT GAA

AGA GCC TTC AAG GCC TGG GCT GTT GCT AGA TTG TCT CAA

AGA TTC CCA AAG GCT GAA TTT GCT GAA GTT TCT AAG TTG

GTT ACT GAC TTG ACT AAG GTT CAC ACT GAA TGT TGT CAC

GGT GAC TTG TTG GAA TGT GCT GAC GAC AGA GCT GAC TTG

GCT AAG TAT ATC TGT GAA AAC CAA GAC TCT ATC TCT TCT

AAG TTG AAG GAA TGT TGT GAA AAG CCA TTG TTG GAA AAG

TCT CAC TGT ATC GCT GAA GTT GAA AAC GAC GAA ATG CCA

GCT GAC TTG CCA TCT TTG GCT GCT GAC TTC GTT GAA TCT

AAG GAC GTT TGT AAG AAC TAC GCT GAA GCT AAG GAC GTT

TTC TTG GGT ATG TTC TTG TAC GAA TAC GCT AGA AGA CAC

CCA GAC TAC TCC GTT GTT TTG TTG TTG AGA TTG GCT AAG

ACT TAC GAA ACT ACT TTG GAA AAG TGT TGT GCT GCT GCT

GAC CCA CAC GAA TGT TAC GCT AAG GTT TTC GAC GAA TTT

AAG CCA TTG GTT GAA GAA CCA CAA AAC TTG ATT AAG CAA

AAC TGT GAA TTG TTC AAG CAA TTG GGT GAA TAC AAG TTC

CAA AAC GCT TTG TTG GTT AGA TAC ACT AAG AAG GTT CCA

CAA GTC TCC ACT CCA ACT TTG GTT GAA GTC TCT AGA AAC

TTG GGT AAG GTT GGT TCT AAG TGT TGT AAG CAC CCA GAA

GCT AAG AGA ATG CCA TGT GCT GAA GAC TAC TTG TCT GTT

GTT TTG AAC CAA TTA TGT GTT TTG CAC GAA AAG ACT CCA

GTT TCT GAC AGA GTT ACT AAG TGT TGT ACT GAA TCT TTG

GTT AAC AGA AGA CCA TGT TTC TCT GCC TTG GAA GTT GAC

GAA ACT TAC GTC CCA AAG GAA TTT AAC GCT GAA ACT TTC

ACT TTC CAC GCC GAC ATC TGT ACC TTG TCC GAA AAG GAA

AGA CAA ATC AAG AAG CAA ACT GCT TTG GTT GAA TTG GTT

-continued

```
AAG CAC AAG CCA AAG GCT ACT AAG GAA CAA TTG AAG GCT

GTT ATG GAC GAC TTC GCT GCT TTC GTT GAA AAG TGT TGT

AAG GCT GAC GAC AAG GAA ACT TGT TTC GCT GAA GAA GGT

AAG AAG TTG GTT GCT GCT TCT CAA GCT GCT TTG GGT TTG

TAA TAG.
```

3. A structural gene according to claim 1, supplemented by an upstream nucleotide sequence coding for methionine.

4. A structural gene according to claim 1, extended by an upstream nucleotide sequence which codes for the amino acid sequence Met–Lys–Trp–Val–Thr–Phe–Ile–Ser–Leu–Leu–Phe–Leu–Phe–

–Ser–Ser–Ala–Tyr–Ser–Arg–Gly–Val–Phe–Lys–Arg wherein the codons have been selected with regard to a yeast host which has known codon usage.

5. A structural gene according to claim 4 wherein the nucleotide sequence which codes for the amino acid sequence is

```
ATG AAG TGG GTT ACT TTC ATC TCT TTG TTG TTC TTG TTC

TCT TCT GCT TAC TCT AGA GGT GTT TTC AAG AGG
```

6. A recombinant DNA molecule comprising a gene according to claim 1, inserted into a vector.

7. A host transformed with a recombinant DNA molecule according to claim 6.

8. A method of producing a structural gene coding for authentic human serum albumin, said method comprising the following steps,
   a) designing the nucleotide sequence coding for authentic human serum albumin by selecting codons with regard to a yeast host which has known codon usage and which is chosen for expression of authentic human serum albumin, whereby the selection of the codons is effected so that
      in the first instance, codons most frequently used by the yeast host are selected, and
      in the second instance, codons used by the yeast host in the second or third place are selected,
      to avoid the appearance of such restriction sites which are used during the assembly of a gene,
      to create one unique cleavage site between a 5'-fragment and the rest of the whole gene, and
      to eliminate 8-base-pairs long or longer palindromes within oligonucleotide subunits of fragments to be cloned,
   b) dividing the designed nucleotide sequence into a 5'-fragment to be chemically synthesized and a selected number of fragments to be cloned so that the joining points between said fragments to be cloned will be at G-C dinucleotide sites in the designed nucleotide sequence,
   c) modifying said designed fragments of b) which are to be cloned by supplementing each of them with an extra nucleotide sequence GGTAC at the 5'-terminus, except for the one fragment to be joined to the 5'-fragment of b), and further dividing said modified fragments into subunits having a 3'-nucleotide G, which subunits in turn are individually supplemented with an extra 3' nucleotide sequence GGCC;
   d) individually chemically synthesizing the modified supplemented subunits of c) in single-stranded form in per se known manner, and chemically synthesizing the 5' fragment of b) in double-stranded form in per se known manner;
   e) consecutively cloning the synthesized subunits of d) starting from the 5'-terminus of the modified supplemented fragments of c) into individual recombinant vectors in per se known manner, with the aid of adapters and enzymatical filling-in reaction, to form cloned double-stranded fragments of the gene, which correspond to the modified supplemented fragments of c),
   f) assembling the cloned double-stranded fragments of e) by cleaving said recombinant vectors of e), in pairs, with the enzyme KpnI and the enzyme ApaI, respectively, —one at the created 5'-terminal KpnI restriction site, and other at the created 3' terminal ApaI restriction site, —to form sticky ends which are made blunt ends by a single-strand-specific enzyme in per se known manner—leaving an end-nucleotide C and an end-nucleotide G, respectively—followed by cleavage with another restriction enzyme having a cleavage site which is unique in both of the recombinant vectors of the pair in question,
      to form on the one hand a linear vector containing a cloned fragment of the gene and, on the other hand, a cleaved-off fragment of the gene, which two last-mentioned fragments are, in per se known manner, enzymatically joined at the blunt ends—a dinucleotide G-C which is included in the nucleotide sequence of the gene, being formed at the joining point
      to obtain a recombinant vector which finally includes said number of designed fragments of b) in double-stranded form, and
   g) supplementing the recombinant vector obtained in f) with the chemically synthesized 5' fragment of d) to form the whole structural gene coding for authentic human serum albumin.

9. A method of producing a structural gene according to claim 8, wherein in b), the designed nucleotide sequence is

GAC GCT CAC AAG TCT GAA GTC GCT CAC AGA TTC AAG GAT

C TA GGT GAA GAA AAC TTC AAG GCT TTG GTT TTG ATT GCT
↑

TTC GCT CAA TAC TTG CAA CAA TGT CCA TTC GAA GAC CAC

GTC AAG TTG GTC AAC GAA GTT ACT GAA TTT GCT AAG ACC

TGT GTT GCT GAC GAA TCT GCT GAA AAC TGT GAC AAG TCC

TTG CAC ACT TTG TTC GGT GAC AAG TTG TGT ACT GTT GCT

ACT TTG AGA GAA ACT TAC GGT GAA ATG GCT GAC TGT TGT

GCT AAA CAG GAA CCA GAA AGA AAC GAA TGT TTC TTA CAA

CAC AAG GAC GAC AAC CCA AAC TTG CCA AGA TTG GTT AGA

CCA GAA GTC GAC GTT ATG TGT ACT GCT TTC CAC GAC AAC

GAA GAG ACT TTC TTG AAG AAG TAC TTG TAC GAA ATC GCC

AGA AGA CAC CCA TAC TTC TAC GCT CCA GAA TTG TTG TTC

TTC G CT AAG AGA TAC AAG GCT GCT TTC ACT GAA TGT TGT
  ↑

CAA GCT GCC GAC AAG GCT GCT TGT TTG TTG CCA AAG TTG

GAC GAA TTG AGA GAC GAA GGT AAG GCT TCT TCC GCT AAG

CAA AGA TTG AAG TGT GCT TCC TTG CAA AAG TTC GGT GAA

AGA GCC TTC AAG GCC TGG GCT GTT GCT AGA TTG TCT CAA

AGA TTC CCA AAG GCT GAA TTT GCT GAA GTT TCT AAG TTG

GTT ACT GAC TTG ACT AAG GTT CAC ACT GAA TGT TGT CAC

GGT GAC TTG TTG GAA TGT GCT GAC GAC AGA GCG GAC TTG

GCT AAG TAT ATC TGT GAA AAC CAA GAC TCT ATC TCT TCT

AAG TTG AAG GAA TGT TGT GAA AAG CCA TTG TTG GAA AAG

TCT CAC TGT ATC GCT GAA GTT GAA AAC GAC GAA ATG  CCA
                                                ↑

GCT GAC TTG CCA TCT TTG GCT GCT GAC TTC GTT GAA TCT

AAG GAC GTT TGT AAG AAC TAC GCT GAA GCT AAG GAC GTT

TTC TTG GGT ATG TTC TTG TAC GAA TAC GCT AGA AGA CAC

CCA GAC TAC TCC GTT GTT TTG TTG TTG AGA TTG GCT AAG

-continued

ACT TAC GAA ACT ACT TTG GAA AAG TGT TGT GCT GCT GCT

GAC CCA CAC GAA TGT TAC GCT AAG GTT TTC GAC GAA TTT

AAG CCA TTG GTT GAA GAA CCA CAA AAC TTG ATT AAG CAA

AAC TGT GAA TTG TTC AAG CAA TTG GGT GAA TAC AAG TTC

CAA AAC GCT TTG TTG GTT AGA TAC ACT AAG AAG GTT CCA

CAA GTC TCC ACT CCA ACT TTG GTT GAA GTC TCT AGA AAC

TTG GGT AAG GTT GGT TCT AAG TGT TGT AAG CAC CCA GAA

GCT AAG AGA ATG ↑ CCA TGT GCT GAA GAC TAC TTG TCT GTT

GTT TTG AAC CAA TTA TGT GTT TTG CAC GAA AAG ACT CCA

GTT TCT GAC AGA GTT ACT AAG TGT TGT ACT GAA TCT TTG

GTT AAC AGA AGA CCA TGT TTC TCT GCC TTG GAA GTT GAC

GAA ACT TAC GTC CCA AAG GAA TTT AAC GCT GAA ACT TTC

ACT TTC CAC GCC GAC ATC TGT ACC TTG TCC GAA AAG GAA

AGA CAA ATC AAG AAG CAA ACT GCT TTG GTT GAA TTG GTT

AAG CAC AAG CCA AAG GCT ACT AAG GAA CAA TTG AAG GCT

GTT ATG GAC GAC TTC GCT GCT TTC GTT GAA AAG TGT TGT

AAG GCT GAC GAC AAG GAA ACT TGT TTC GCT GAA GAA GGT

AAG AAG TTG GTT GCT GCT TCT CAA GCT GCT TTG GGT TTG

TAA TAG in which the arrows show the dividing points between the first 5' fragment to be chemically synthesized and four fragments to be cloned, in c), the supplemented single-stranded subunits of the modified rents of b) are

TAGGTGAAGAAAACTTCAAGGCTTTGGTTTTGATTGCTTTCGCTCAATACT—
TGCAACAATGTCCATTCGAAGGGCC

ACCACGTCAAGTTGGTCAACGAAGTTACTGAATTTGCTAAGACCTGTGTT—
GCTGACGAATCTGCTGAAAACTGGGCC

TGACAAGTCCTTGCACACTTTGTTCGGTGACAAGTTGTGTACTGTTGCT—
ACTTTGAGAGAAACTTACGGTGGGCC

AAATGGCTGACTGTTGTGCTAAACAGGAACCAGAAAGAAACGAATGTTTCT—
TACAACACAAGGACGGGCC

ACAACCCAAACTTGCCAAGATTGGTTAGACCAGAAGTCGACGTTATGTG—
TACTGCTTTCCACGACAACGAAGGGCC

AGACTTTCTTGAAGAAGTACTTGTACGAAATCGCCAGAAGACACCCATAC—
TTCTACGCTCCAGAATTGTTGTTCTTCGGGCC

-continued
```
GGTACCTAAGAGATACAAGGCTGCTTTCACTGAATGTTGTCAAGCTGCCGAC—
AAGGCTGCTTGTTTGTTGGGCC

CCAAAGTTGGACGAATTGAGAGACGAAGGTAAGGCTTCTTCCGCTAAGCA—
AAGATTGAAGTGTGCTTCCTTGGGCC

CAAAAGTTCGGTGAAAGAGCCTTCAAGGCCTGGGCTGTTGCTAGATTGTC—
TCAAAGATTCCCAAAGGCTGGGCC

AATTTGCTGAAGTTTTCTAAGTTGGTTACTGACTTGACTAAGGTTCACACTGA—
ATGTTGTCACGGTGACTTGGGCC

TTGGAATGTGCTGACGACAGAGCTGACTTGGCTAAGTATATCTGTGAAAACCA—
AGACTCTATCTCTTCTAAGGGCC

TTGAAGGAATGTTGTGAAAAGCCATTGTTGGAAAAGTCTCACTGTATCGCT—
GAAGTTGAAAACGACGAAATGGGCC

GGTACCCAGCTGACTTGCCATCTTTGGCTGCTGACTTCGTTGAATCTAAG—
GACGTTTGTAAGAACTACGCTGAAGGGCC

CTAAGGACGTTTTCTTGGGTATGTTCTTGTACGAATACGCTAGAAGACACC—
CAGACTACTCCGTTGTTTTGTTGTTGGGCC

AGATTGGCTAAGACTTACGAAACTACTTTGGAAAAGTGTTGTGCTGCTGCT—
GACCCACACGAATGTTACGCTAAGGGCC

GTTTTCGACGAATTTAAGCCATTGGTTGAAGAACCACAAAACTTGATTAAG—
CAAAACTGTGAATTGTTCAAGGGCC

CAATTGGGTGAATACAAGTTCCAAAACGCTTTGTTGGTTAGATACACTAA—
GAAGGTTCCACAAGTCTCCACTCCAACTTTGGGCC

GTTGAAGTCTCTAGAAACTTGGGTAAGGTTGGTTCTAAGTGTTGTAAGCAC—
CCAGAAGCTAAGAGAATGGGCC

GGTACCCATGTGCTGAAGACTACTTGTCTGTTGTTTTGAACCAATTATGTGT—
TTTGCACGAAAAGGGCC

ACTCCAGTTTCTGACAGAGTTACTAAGTGTTGTACTGAATCTTTGGTTAACA—
GAAGACCATGTTTCTCTGGGCC

CCTTGGAAGTTGACGAAACTTACGTCCCAAAGGAATTTAACGCTGAAACTT—
TCACTTTCCACGCCGACATCTGGGCC

TACCCTTGTCCGAAAAGGAAAGACAAATCAAGAAGCAAACTGCTTTGGTTGAA—
TTGGTTAAGCACAAGCCAAAGGGCC

GCTACTAAGGAACAATTGAAGGCTGTTATGGACGACTTCGCTGCTTTCGTT—
GAAAAGTGTTGTAAGGCTGACGGGCC

ACAAGGAAACTTGTTTCGCTGAAGAAGGTAAGAAGTTGGTTGCTGCTTCTCAA—
GCTGCTTTGGGTTTGTAATAGGGCC
``` in e), the synthesized subunits of d) are consecutively cloned into four individual *E. coli* vectors with the aid of the adapters

```
ApaI              EcoRI
      CGGACGGCGACGGCGACGGCGACCG
CCCGGGCCTGCCGCTGCCGCTGCCGCTGGCTTAA

ApaI              EcoRI
         CGAGTATGCGACAGCTGG
CCCGGGCTCATACGCTGTCGACCTTAA
``` in f), the single-strand-specific enzyme is Klenow polymerase.

10. A method of producing authentic human serum albumin which comprises propagating under expression of a yeast host transformed with a vector wherein said vector comprises a recombinant DNA sequence, followed by isolating authentic human serum albumin, wherein said recombinant DNA sequence includes the structural gene according to claim 1.

\* \* \* \* \*